(12) United States Patent
De Maria et al.

(10) Patent No.: US 8,772,011 B2
(45) Date of Patent: *Jul. 8, 2014

(54) PROTEASE VARIANTS

(71) Applicant: Novozymes A/S, Bagsvaerd (DK)

(72) Inventors: Leonardo De Maria, Frederiksberg (DK); Carsten Andersen, Vaerloese (DK); Lars Lehmann Hylling Christensen, Allerod (DK); Soren Flensted Lassen, Farum (DK); Peter Rahbek Ostergaard, Virum (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/738,490

(22) Filed: Jan. 10, 2013

(65) Prior Publication Data

US 2013/0189732 A1 Jul. 25, 2013

Related U.S. Application Data

(62) Division of application No. 12/984,826, filed on Jan. 5, 2011, now Pat. No. 8,377,677, which is a division of application No. 10/574,554, filed as application No. PCT/DK2004/000688 on Oct. 8, 2004, now Pat. No. 7,892,808.

(60) Provisional application No. 60/510,450, filed on Oct. 10, 2003, provisional application No. 60/549,347, filed on Mar. 2, 2004.

(30) Foreign Application Priority Data

Oct. 10, 2003 (DK) .................................. 2003 01494
Mar. 1, 2004 (DK) .................................. 2004 00333

(51) Int. Cl.
*C12N 9/52* (2006.01)
*A23K 1/165* (2006.01)

(52) U.S. Cl.
USPC .......................................... 435/221; 426/53

(58) Field of Classification Search
None
See application file for complete search history.

(56) References Cited

U.S. PATENT DOCUMENTS

| | | | |
|---|---|---|---|
| 3,683,069 A | 8/1972 | Hooreman |
| 3,723,250 A | 3/1973 | Aunstrup et al. |
| 3,823,072 A | 7/1974 | Hooreman |
| 3,868,448 A | 2/1975 | Hahn et al. |
| 3,966,971 A | 6/1976 | Morehouse et al. |
| 4,073,884 A | 2/1978 | Hartegen |
| 4,473,644 A | 9/1984 | Schindler et al. |
| 4,518,697 A | 5/1985 | Bartnik et al. |
| 5,047,240 A | 9/1991 | Hooreman |
| 5,312,748 A | 5/1994 | Liu et al. |
| 5,646,028 A | 7/1997 | Leigh |
| 5,705,379 A | 1/1998 | Wilson et al. |
| 5,811,382 A | 9/1998 | Damhius et al. |
| 5,877,403 A | 3/1999 | McMaster et al. |
| 6,855,548 B2 | 2/2005 | Sjoeholm |
| 6,960,462 B2 | 11/2005 | Sjoeholm et al. |
| 7,179,630 B2 | 2/2007 | Lassen et al. |
| 7,208,310 B2 | 4/2007 | Lassen et al. |
| 7,485,447 B2 | 2/2009 | Lassen |
| 7,588,926 B2 | 9/2009 | Oestergaard et al. |
| 7,608,444 B2 | 10/2009 | Oestergaard et al. |
| 7,618,801 B2 | 11/2009 | Jones et al. |
| 7,630,836 B2 | 12/2009 | Omura et al. |
| 7,658,965 B2 | 2/2010 | Sjoeholm et al. |
| 7,892,808 B2 | 2/2011 | De Maria et al. |
| 7,906,310 B2 | 3/2011 | Oestergaard et al. |
| 8,067,238 B2 | 11/2011 | Sjoeholm |
| 8,153,396 B2 | 4/2012 | Lynglev |
| 8,357,408 B2 * | 1/2013 | Lassen et al. .................... 426/63 |
| 8,377,677 B2 * | 2/2013 | De Maria et al. ............. 435/220 |
| 2001/0026797 A1 | 10/2001 | Sjoeholm |
| 2006/0143738 A1 | 6/2006 | Lassen |
| 2006/0147499 A1 | 7/2006 | Oestergaard |
| 2006/0236414 A1 | 10/2006 | Lassen |
| 2007/0104764 A1 | 5/2007 | Jensen et al. |
| 2007/0259404 A1 | 11/2007 | Jorgensen |
| 2008/0286415 A1 | 11/2008 | Lassen |
| 2008/0293104 A1 | 11/2008 | Lassen |
| 2009/0047387 A1 | 2/2009 | De Maria et al. |
| 2010/0081168 A1 | 4/2010 | Sjoeholm |
| 2010/0093025 A1 | 4/2010 | Kalum |

(Continued)

FOREIGN PATENT DOCUMENTS

DE 2004328 5/1983
DK PA 2003 00013 1/2003

(Continued)

OTHER PUBLICATIONS

Altschul et al., GenPept Database, Accession No. PQ0104 (1997).

(Continued)

*Primary Examiner* — Manjunath Rao
*Assistant Examiner* — William W Moore
(74) *Attorney, Agent, or Firm* — Elias Lambiris

(57) ABSTRACT

The invention relates to a novel 3D structure encoding a *Nocardiopsis protease*, as well as to variants of parent protease homologous to *Nocardiopsis* proteases, preferably of improved thermostability and/or with an amended temperature activity profile. The invention also relates to DNA sequences encoding such variants, their production in a recombinant host cell, as well as methods of using the variants, in particular within the field of animal feed and detergents. The invention furthermore relates to methods of generating and preparing protease variants of amended properties.

20 Claims, 26 Drawing Sheets

(56) References Cited

U.S. PATENT DOCUMENTS

| | | | |
|---|---|---|---|
| 2010/0093633 A1 | 4/2010 | De Maria | |
| 2010/0255153 A1 | 10/2010 | Oestergaard | |
| 2010/0322915 A1 | 12/2010 | Svendsen | |
| 2011/0081450 A1 | 4/2011 | Lynglev | |
| 2011/0097448 A1 | 4/2011 | Wong | |
| 2011/0097760 A1 | 4/2011 | Lynglev | |
| 2012/0321746 A1* | 12/2012 | Lassen et al. | 426/63 |
| 2012/0321747 A1* | 12/2012 | Lassen et al. | 426/63 |

FOREIGN PATENT DOCUMENTS

| | | |
|---|---|---|
| EP | 0 130 756 A1 | 1/1985 |
| EP | 0 300 466 B1 | 1/1989 |
| EP | 0 506 448 A1 | 9/1992 |
| EP | 0 516 200 B1 | 12/1992 |
| EP | 0 647 710 B1 | 4/1995 |
| EP | 0 897 985 A2 | 2/1999 |
| JP | 02255081 | 10/1990 |
| JP | 2003 284571 | 10/2003 |
| JP | 2004 043660 | 2/2004 |
| WO | WO 88/03947 A1 | 6/1988 |
| WO | WO 91/00345 A1 | 1/1991 |
| WO | WO 91/10723 A1 | 7/1991 |
| WO | WO 92/19729 A1 | 11/1992 |
| WO | WO 95/02044 A1 | 1/1995 |
| WO | WO 95/21540 A1 | 8/1995 |
| WO | WO 95/28850 A1 | 11/1995 |
| WO | WO 96/05739 A1 | 2/1996 |
| WO | WO 98/56260 A2 | 12/1998 |
| WO | WO 99/53038 A2 | 10/1999 |
| WO | WO 01/58276 A2 | 8/2001 |
| WO | WO 2004/070106 A1 | 8/2004 |
| WO | WO 2004/072221 A1 | 8/2004 |
| WO | WO 2004/072279 A2 | 8/2004 |
| WO | WO 2004/111219 A1 | 12/2004 |
| WO | WO 2004/111220 A1 | 12/2004 |
| WO | WO 2004/111221 A1 | 12/2004 |
| WO | WO 2004/111222 A1 | 12/2004 |
| WO | WO 2004/111223 A1 | 12/2004 |
| WO | WO 2004/111224 A1 | 12/2004 |
| WO | WO 2005-115445 A1 | 12/2005 |

OTHER PUBLICATIONS

Anderson et al., Database GeneSeq, Accession No. AAQ29011-Seq0001 (1992).
Anderson et al., Database GeneSeq, Accession No. AAQ29011-Seq0011 (1992).
Barrett et al., Handbook of Proteolytic Enzymes, pp. 2-3 (1998).
Caine et al., Animal Feed Sci. Technology, vol. 71, pp. 177-183 (1998).
Derwent Abstract: XP-002310338 (Aug. 19, 2004).
Derwent Abstract: XP-002308395 submitted to the EMBL/GenBankDDBJ databases (Sep. 18, 2002).
Dixit et al., Biochim. Biophys. Acta, vol. 1523, No. 2-3, pp. 261-268 (2000).
FASTA sequence Alignments (1993, 1994, and 2002).
Fernandez-Abalos et al., Microbiology, vol. 149, pp. 1623-1632 (2003).
Gayle et al., J. Biol. Chem., vol. 268, No. 29, pp. 22105-22111 (1993).
Gill et al., Analytical Biochem., vol. 182, pp. 319-326 (1989).
Goodenough et al. Molecular Biotechnology, vol. 4, No. 1, pp. 151-166 (1995).
Henderson et al., J. Bacteriol., vol. 169, No. 8, pp. 3778-3784 (1987).
Heringa et al., Protein Engineering, vol. 8, No. 1, pp. 21-30 (1995).
Higgins et al., Gene, vol. 73, pp. 237-244 (1988).
Kaneda et al., J. Biochem., vol. 78, pp. 1287-1296 (1975).
Kim et al., Korean Biotech. J., vol. 26, No. 1, pp. 81-85 (1993).
Lao et al., Appl. Environ. Microbiol., vol. 62, No. 11, pp. 4256-4259 (1996).
Merops Database, Alignment of Subfamily S1E Peptidases (2004).
Michalik et al., Ukr. Biokhim. Zh., vol. 69, No. 3, pp. 28-35 (1997).
Mitsuiki et al., Biosci. Biotechnol. Biochem., vol. 66, No. 1, pp. 164-167 (2002).
Mitsuiki et al., Database EMBL, Accession No. AY151208 (2004).
Mitsuiki et al., Enzyme and Microbiol Technology, vol. 34, No. 5, pp. 482-489 (2004).
Moreira et al., World Journal of Microbiology and Biotechnology, vol. 18, No. 4, pp. 307-312 (2002).
Needleman et al., J. Mol. Biology, vol. 48, pp. 443-453 (1970).
Novozymes, Database A_Geneseq, Accession No. AAW92997 (1999).
Novozymes, Database N_Geneseq, Accession No. AAX22316 (1999).
O'Fagain, Enzyme and Microbial Technology, vol. 33, pp. 137-149 (2003).
Ostergaard et al., Database A_Geneseq, Accession No. AAU07125 (2003).
Refstie et al., Aquaculture, vol. 162, pp. 301-312 (1998).
Sambrook et al., Molecular Cloning $3^{rd}$ Edition, vol. 2, pp. 10.47-1048 (2001).
Screen et al., J. Biol. Chem., vol. 275, No. 9, pp. 6689-6694 (2000).
Sidhu et al., J. Biol. Chem., vol. 269, No. 31, pp. 20167-20171 (1994).
Smith et al., Analytical Biochem., vol. 150, pp. 76-85 (1985).
Tsuijibo et al., Agric. Biol. Chem., vol. 54, No. 8, pp. 2177-2179 (1990).
Tsuijibo et al., J. Appl. Bacteriol., vol. 69, pp. 520-529 (1990).
Tsuijibo et al, Appl. Environ. Microbiol., vol. 69, No. 2, pp. 894-900 (2003).
Vielle et al., Microbiology and Molecular Biology Reviews, vol. 65, No. 1, pp. 1-43 (2001).
Whisstock et al, Quart. Rev. Biophysic., vol. 36, No. 3, pp. 307-340 (2003).
Seffernick et al., Journal of Bacteriology, vol. 183, No. 8, pp. 2405-2410 (2001).
Witkowski et al., Biochemistry, vol. 38, pp. 11643-11650 (1999).
Guo et al., Proc. Natl. Acad. Sci., vol. 101, No. 25, pp. 9205-9210 (2004).

* cited by examiner

```
                         1                                                 50
            Protease 10  ADIIGGLAYTMGGRCSVGFAATNAAGQPGFVTAGHCGRVGTQVTIGNGRG
            Protease 18  ADIIGGLAYYMGGRCSVGFAATNSAGQPGFVTAGHCGTVGTGVTIGNGTG
            Protease 11  ADIIGGLAYTMGGRCSVGFAATNAAGQPGFVTAGHCGRVGTQVSIGNGQG
            Protease 35  ADIIGGLAYTMGGRCSVGFAATNAAGQPGFVTAGHCGRVGTQVTIGNGRG
            Protease 08  ADIIGGLAYTMGGRCSVGFAATNASGQPGFVTAGHCGTVGTPVSIGNGQG
            Protease 22  ADIIGGLAYYMGGRCSVGFAATNASGQPGFVTAGHCGTVGTPVSIGNGKG 51                                                100
            Protease 10  VFEQSVFPGNDAAFVRGTSNFTLTNLVSRYNTGGYATVAGHNQAPIGSSV
            Protease 18  TFQNSVFPGNDAAFVRGTSNFTLTNLVSRYNSGGYQSVTGTSQAPAGSAV
            Protease 11  VFEQSIFPGNDAAFVRGTSNFTLTNLVSRYNTGGYATVAGHNQAPIGSSV
            Protease 35  VFEQSIFPGNDAAFVRGTSNFTLTNLVSRYNTGGYATVAGHNQAPIGSSV
            Protease 08  VFERSVFPGNDSAFVRGTSNFTLTNLVSRYNTGGYATVSGSSQAAIGSQI
            Protease 22  VFERSIFPGNDSAFVRGTSNFTLTNLVSRYNSGGYATVAGHNQAPIGSAV 101                                               150
            Protease 10  CRSGSTTGWHCGTIQARGQSVSYPEGTVTNMTRTTVCAEPGDSGGSYISG
            Protease 18  CRSGSTTGWHCGTIQARNQTVRYPQGTVYSLTRTNVCAEPGDSGGSFISG
            Protease 11  CRSGSTTGWHCGTIQARGQSVSYPEGTVTNMTRTTVCAEPGDSGGSYISG
            Protease 35  CRSGSTTGWHCGTIQARGQSVSYPEGTVTNMTRTTVCAEPGDSGGSYISG
            Protease 08  CRSGSTTGWHCGTVQARGQTVSYPQGTVQNLTRTNVCAEPGDSGGSFISG
            Protease 22  CRSGSTTGWHCGTIQARNQTVRYPQGTVYSLTRTTVCAEPGDSGGSYISG 151                            188
            Protease 10  TQAQGVTSGGSGNCRTGGTTFYQEVTPMVNSWGVRLRT
            Protease 18  SQAQGVTSGGSGNCSVGGTTYYQEVTPMINSWGVRIRT
            Protease 11  NQAQGVTSGGSGNCRTGGTTFYQEVTPMVNSWGVRLRT
            Protease 35  NQAQGVTSGGSGNCRTGGTTFYQEVTPMVNSWGVRLRT
            Protease 08  SQAQGVTSGGSGNCSFGGTTYYQEVNPMLSSWGLTLRT
            Protease 22  TQAQGVTSGGSGNCSAGGTTYYQEVNPMLSSWGLTLRT
```

Fig. 1

```
ATOM      1  N    ALA     1     -18.517  32.531  28.661  1.00   8.90
ATOM      2  CB   ALA     1     -18.802  30.741  30.290  1.00  12.24
ATOM      3  CA   ALA     1     -19.308  31.313  28.965  1.00  10.86
ATOM      4  C    ALA     1     -20.783  31.666  29.080  1.00  12.18
ATOM      5  O    ALA     1     -21.113  32.695  29.712  1.00  12.73
ATOM      6  N    ASP     2     -21.722  30.930  28.510  1.00  12.01
ATOM      7  CA   ASP     2     -23.176  31.225  28.612  1.00  12.07
ATOM      8  C    ASP     2     -23.667  30.604  29.929  1.00  10.24
ATOM      9  O    ASP     2     -23.359  29.410  30.109  1.00  11.30
ATOM     10  CB   ASP     2     -23.995  30.629  27.422  1.00  12.43
ATOM     11  CG   ASP     2     -23.545  31.314  26.129  1.00  16.23
ATOM     12  OD1  ASP     2     -23.300  30.668  25.134  1.00  21.68
ATOM     13  OD2  ASP     2     -23.346  32.527  26.168  1.00  17.64
ATOM     14  N    ILE     3     -24.387  31.321  30.757  1.00   9.80
ATOM     15  CA   ILE     3     -24.850  30.687  32.027  1.00   8.80
ATOM     16  C    ILE     3     -26.252  30.135  31.768  1.00   7.97
ATOM     17  O    ILE     3     -27.160  30.953  31.648  1.00   8.91
ATOM     18  CB   ILE     3     -24.789  31.723  33.207  1.00   7.85
ATOM     19  CG1  ILE     3     -23.378  32.342  33.312  1.00   5.63
ATOM     20  CG2  ILE     3     -25.284  31.096  34.549  1.00   4.75
ATOM     21  CD1  ILE     3     -22.221  31.320  33.579  1.00   5.82
ATOM     22  N    ILE     4     -26.319  28.814  31.563  1.00   7.21
ATOM     23  CD1  ILE     4     -26.578  27.854  27.424  1.00   8.61
ATOM     24  CG1  ILE     4     -27.102  28.463  28.794  1.00   8.70
ATOM     25  CB   ILE     4     -27.272  27.363  29.888  1.00   7.20
ATOM     26  CG2  ILE     4     -28.446  26.419  29.544  1.00   6.35
ATOM     27  CA   ILE     4     -27.569  28.083  31.259  1.00   7.04
ATOM     28  C    ILE     4     -27.799  27.046  32.350  1.00   7.12
ATOM     29  O    ILE     4     -26.841  26.414  32.764  1.00   5.80
ATOM     30  N    GLY     5     -29.017  26.894  32.834  1.00   8.40
ATOM     31  CA   GLY     5     -29.415  25.958  33.863  1.00   5.51
ATOM     32  C    GLY     5     -29.031  24.550  33.483  1.00   6.74
ATOM     33  O    GLY     5     -29.222  24.181  32.306  1.00   8.02
ATOM     34  N    GLY     6     -28.492  23.787  34.436  1.00   5.32
ATOM     35  CA   GLY     6     -28.113  22.385  34.125  1.00   6.51
ATOM     36  C    GLY     6     -26.697  22.143  33.678  1.00   7.67
ATOM     37  O    GLY     6     -26.264  20.957  33.687  1.00   8.08
ATOM     38  N    LEU     7     -25.941  23.127  33.235  1.00   7.02
ATOM     39  CD2  LEU     7     -25.075  23.250  29.859  1.00  15.01
ATOM     40  CD1  LEU     7     -24.009  25.544  29.892  1.00  12.10
ATOM     41  CG   LEU     7     -24.823  24.494  30.662  1.00  11.57
ATOM     42  CB   LEU     7     -24.100  24.149  31.987  1.00   7.81
ATOM     43  CA   LEU     7     -24.543  22.889  32.774  1.00   7.23
ATOM     44  C    LEU     7     -23.543  22.624  33.891  1.00   8.17
ATOM     45  O    LEU     7     -23.779  23.055  35.054  1.00   8.83
ATOM     46  N    ALA     8     -22.450  21.931  33.560  1.00   7.85
ATOM     47  CB   ALA     8     -20.568  20.517  33.998  1.00   7.20
ATOM     48  CA   ALA     8     -21.436  21.658  34.583  1.00   6.67
ATOM     49  C    ALA     8     -20.554  22.867  34.856  1.00   8.14
ATOM     50  O    ALA     8     -20.241  23.793  34.058  1.00   7.62
ATOM     51  N    TYR     9     -20.078  22.906  36.110  1.00   6.90
ATOM     52  CA   TYR     9     -19.074  23.854  36.602  1.00   7.03
ATOM     53  C    TYR     9     -18.138  22.960  37.480  1.00   8.21
ATOM     54  O    TYR     9     -18.560  21.945  38.048  1.00   7.61
```

```
ATOM     55  CB  TYR     9     -19.474  25.108  37.320  1.00   7.45
ATOM     56  CG  TYR     9     -20.138  24.925  38.664  1.00   9.14
ATOM     57  CD1 TYR     9     -19.401  24.898  39.853  1.00   8.86
ATOM     58  CD2 TYR     9     -21.559  24.818  38.673  1.00   8.66
ATOM     59  CE1 TYR     9     -20.044  24.756  41.062  1.00   7.11
ATOM     60  CE2 TYR     9     -22.214  24.696  39.930  1.00   8.78
ATOM     61  CZ  TYR     9     -21.438  24.673  41.072  1.00   7.41
ATOM     62  OH  TYR     9     -22.115  24.537  42.248  1.00   8.28
ATOM     63  N   THR    10     -16.867  23.367  37.552  1.00   8.23
ATOM     64  CG2 THR    10     -15.380  21.144  36.171  1.00  21.51
ATOM     65  OG1 THR    10     -14.022  22.954  36.816  1.00  17.27
ATOM     66  CB  THR    10     -14.816  21.869  37.398  1.00  15.54
ATOM     67  CA  THR    10     -15.881  22.592  38.334  1.00  12.22
ATOM     68  C   THR    10     -15.190  23.495  39.381  1.00  12.59
ATOM     69  O   THR    10     -15.040  24.724  39.295  1.00  11.83
ATOM     70  N   MET    11     -14.719  22.854  40.422  1.00  13.86
ATOM     71  CE  MET    11     -18.117  21.521  42.992  0.70  10.20
ATOM     72  SD  MET    11     -16.364  21.817  43.260  0.70  13.92
ATOM     73  CG  MET    11     -16.351  23.607  42.742  0.70   8.87
ATOM     74  CB  MET    11     -14.945  24.074  42.557  0.70  13.60
ATOM     79  CA  MET    11     -14.003  23.423  41.576  1.00  14.74
ATOM     80  C   MET    11     -13.204  22.219  42.141  1.00  16.84
ATOM     81  O   MET    11     -13.132  22.126  43.360  1.00  18.29
ATOM     82  N   GLY    12     -12.650  21.380  41.252  1.00  17.41
ATOM     83  CA  GLY    12     -11.931  20.160  41.721  1.00  20.30
ATOM     84  C   GLY    12     -12.961  19.034  41.377  1.00  22.00
ATOM     85  O   GLY    12     -12.730  18.252  40.444  1.00  25.04
ATOM     86  N   GLY    13     -14.079  19.064  42.126  1.00  17.68
ATOM     87  CA  GLY    13     -15.219  18.171  41.900  1.00  15.21
ATOM     88  C   GLY    13     -16.127  18.873  40.846  1.00  15.26
ATOM     89  O   GLY    13     -15.681  19.862  40.228  1.00  14.61
ATOM     90  N   ARG    14     -17.370  18.410  40.657  1.00  12.77
ATOM     91  NH2 ARG    14     -20.479  14.276  37.036  1.00  17.15
ATOM     92  NH1 ARG    14     -21.587  16.075  36.340  1.00  13.21
ATOM     93  CZ  ARG    14     -20.415  15.529  36.584  1.00  16.51
ATOM     94  NE  ARG    14     -19.265  16.236  36.423  1.00  15.10
ATOM     95  CD  ARG    14     -19.240  17.643  36.031  1.00  15.25
ATOM     96  CG  ARG    14     -19.255  18.517  37.291  1.00  14.76
ATOM     97  CB  ARG    14     -18.333  18.056  38.435  1.00  11.53
ATOM     98  CA  ARG    14     -18.269  19.018  39.659  1.00  11.00
ATOM     99  C   ARG    14     -19.665  19.162  40.278  1.00   9.52
ATOM    100  O   ARG    14     -20.027  18.274  41.091  1.00   8.13
ATOM    101  N   CYS    15     -20.368  20.221  39.853  1.00   8.85
ATOM    102  CA  CYS    15     -21.782  20.417  40.285  1.00   6.14
ATOM    103  C   CYS    15     -22.455  21.027  39.084  1.00   6.53
ATOM    104  O   CYS    15     -21.754  21.176  38.036  1.00   8.10
ATOM    105  CB  CYS    15     -21.897  21.271  41.568  1.00   7.27
ATOM    106  SG  CYS    15     -21.795  20.241  43.088  1.00   8.70
ATOM    107  N   SER    16     -23.746  21.368  39.154  1.00   5.13
ATOM    108  CA  SER    16     -24.402  21.936  37.975  1.00   4.73
ATOM    109  C   SER    16     -24.969  23.294  38.269  1.00   6.73
ATOM    110  O   SER    16     -25.331  23.536  39.470  1.00   7.15
ATOM    111  CB  SER    16     -25.540  20.930  37.602  1.00   5.02
ATOM    112  OG  SER    16     -25.031  19.670  37.228  1.00   7.01
```

```
ATOM    113  N    VAL   17     -25.177   24.129   37.276   1.00   5.71
ATOM    114  CA   VAL   17     -25.780   25.469   37.450   1.00   6.30
ATOM    115  C    VAL   17     -27.274   25.365   37.742   1.00   6.27
ATOM    116  O    VAL   17     -27.904   24.514   37.084   1.00   6.87
ATOM    117  CB   VAL   17     -25.589   26.211   36.113   1.00   4.80
ATOM    118  CG1  VAL   17     -26.252   27.572   36.079   1.00   2.00
ATOM    119  CG2  VAL   17     -24.108   26.435   35.892   1.00   5.56
ATOM    120  N    GLY   18     -27.836   26.136   38.622   1.00   5.84
ATOM    121  CA   GLY   18     -29.277   26.067   38.899   1.00   4.89
ATOM    122  C    GLY   18     -29.898   27.072   37.958   1.00   7.79
ATOM    123  O    GLY   18     -30.578   26.683   36.960   1.00   8.56
ATOM    124  N    PHE   19     -29.783   28.366   38.175   1.00   6.84
ATOM    125  CA   PHE   19     -30.368   29.391   37.291   1.00   8.35
ATOM    126  C    PHE   19     -29.457   30.625   37.254   1.00   8.67
ATOM    127  O    PHE   19     -28.889   30.984   38.285   1.00   7.20
ATOM    128  CB   PHE   19     -31.761   29.873   37.827   1.00   6.74
ATOM    129  CG   PHE   19     -32.786   28.779   38.033   1.00   8.40
ATOM    130  CD1  PHE   19     -33.490   28.300   36.918   1.00   9.81
ATOM    131  CD2  PHE   19     -32.921   28.194   39.301   1.00   8.27
ATOM    132  CE1  PHE   19     -34.414   27.241   37.060   1.00   7.45
ATOM    133  CE2  PHE   19     -33.804   27.129   39.460   1.00   7.36
ATOM    134  CZ   PHE   19     -34.541   26.662   38.347   1.00   8.66
ATOM    135  N    ALA   20     -29.375   31.284   36.114   1.00   8.32
ATOM    136  CB   ALA   20     -28.552   32.954   34.501   1.00   7.08
ATOM    137  CA   ALA   20     -28.577   32.514   35.976   1.00   6.99
ATOM    138  C    ALA   20     -29.347   33.558   36.793   1.00   8.39
ATOM    139  O    ALA   20     -30.614   33.548   36.744   1.00   6.62
ATOM    140  N    ALA   21     -28.653   34.461   37.453   1.00   6.45
ATOM    141  CB   ALA   21     -29.774   34.943   39.600   1.00   6.04
ATOM    142  CA   ALA   21     -29.305   35.514   38.244   1.00   9.09
ATOM    143  C    ALA   21     -28.267   36.598   38.599   1.00  10.25
ATOM    144  O    ALA   21     -27.048   36.412   38.434   1.00  10.39
ATOM    145  N    THR   22     -28.734   37.704   39.154   1.00  10.87
ATOM    146  CA   THR   22     -27.795   38.747   39.633   1.00   9.81
ATOM    147  C    THR   22     -28.044   38.773   41.139   1.00  12.70
ATOM    148  O    THR   22     -29.153   38.378   41.607   1.00  13.28
ATOM    149  CB   THR   22     -28.009   40.191   39.000   1.00  12.32
ATOM    150  OG1  THR   22     -29.443   40.520   39.201   1.00  17.96
ATOM    151  CG2  THR   22     -27.730   40.314   37.512   1.00  10.22
ATOM    152  N    ASN   23     -27.067   39.261   41.919   1.00  12.56
ATOM    153  ND2  ASN   23     -23.651   39.789   44.187   1.00  14.15
ATOM    154  OD1  ASN   23     -25.034   41.090   43.182   1.00  11.99
ATOM    155  CG   ASN   23     -24.917   40.044   43.825   1.00  13.60
ATOM    156  CB   ASN   23     -26.025   39.065   44.153   1.00  12.41
ATOM    157  CA   ASN   23     -27.308   39.367   43.381   1.00  14.31
ATOM    158  C    ASN   23     -27.947   40.754   43.600   1.00  15.71
ATOM    159  O    ASN   23     -28.252   41.558   42.664   1.00  13.68
ATOM    160  N    ALA   24     -28.043   41.088   44.883   1.00  16.68
ATOM    161  CB   ALA   24     -28.899   42.370   46.862   1.00  19.20
ATOM    162  CA   ALA   24     -28.626   42.344   45.371   1.00  20.06
ATOM    163  C    ALA   24     -27.831   43.543   44.936   1.00  22.43
ATOM    164  O    ALA   24     -28.408   44.658   44.795   1.00  24.93
ATOM    165  N    ALA   25     -26.556   43.412   44.648   1.00  23.59
ATOM    166  CA   ALA   25     -25.727   44.513   44.128   1.00  20.79
```

```
ATOM    167   C    ALA   25    -25.765  44.542  42.613  1.00  21.34
ATOM    168   O    ALA   25    -25.018  45.388  42.040  1.00  24.26
ATOM    169   CB   ALA   25    -24.278  44.379  44.584  1.00  24.28'
ATOM    170   N    GLY   26    -26.508  43.687  41.910  1.00  16.97
ATOM    171   CA   GLY   26    -26.453  43.763  40.456  1.00  15.31
ATOM    172   C    GLY   26    -25.320  43.024  39.803  1.00  13.98
ATOM    173   O    GLY   26    -25.158  43.168  38.560  1.00  15.90
ATOM    174   N    GLN   27    -24.594  42.196  40.523  1.00  13.26
ATOM    175   NE2  GLN   27    -19.688  42.607  42.319  1.00  23.84
ATOM    176   OE1  GLN   27    -21.306  41.674  43.669  1.00  19.08
ATOM    177   CD   GLN   27    -20.952  42.234  42.626  1.00  20.42
ATOM    178   CG   GLN   27    -21.934  42.487  41.519  1.00  16.87
ATOM    179   CB   GLN   27    -22.364  41.130  40.909  1.00  13.66
ATOM    180   CA   GLN   27    -23.488  41.430  39.904  1.00  11.98
ATOM    181   C    GLN   27    -24.023  40.113  39.345  1.00  11.67
ATOM    182   O    GLN   27    -24.829  39.428  39.949  1.00  11.63
ATOM    183   N    PRO   28    -23.539  39.714  38.197  1.00  10.36
ATOM    184   CG   PRO   28    -22.111  39.444  36.367  1.00  11.95
ATOM    185   CD   PRO   28    -22.544  40.519  37.403  1.00  10.61
ATOM    186   CB   PRO   28    -23.429  38.692  36.116  1.00  11.06
ATOM    187   CA   PRO   28    -23.977  38.497  37.537  1.00   9.08
ATOM    188   C    PRO   28    -23.418  37.248  38.194  1.00   9.80
ATOM    189   O    PRO   28    -22.278  37.282  38.749  1.00   9.50
ATOM    190   N    GLY   29    -24.245  36.179  38.101  1.00   6.29
ATOM    191   CA   GLY   29    -23.721  34.885  38.671  1.00   4.48
ATOM    192   C    GLY   29    -24.827  33.875  38.440  1.00   6.36
ATOM    193   O    GLY   29    -25.604  34.036  37.454  1.00   7.58
ATOM    194   N    PHE   30    -24.889  32.917  39.339  1.00   7.28
ATOM    195   CA   PHE   30    -25.971  31.891  39.292  1.00   7.77
ATOM    196   C    PHE   30    -26.232  31.306  40.703  1.00   6.83
ATOM    197   O    PHE   30    -25.281  31.334  41.532  1.00   8.49
ATOM    198   CB   PHE   30    -25.653  30.741  38.312  1.00   3.78
ATOM    199   CG   PHE   30    -24.384  29.955  38.483  1.00   5.51
ATOM    200   CD1  PHE   30    -24.299  28.836  39.311  1.00   5.54
ATOM    201   CD2  PHE   30    -23.251  30.336  37.752  1.00   8.26
ATOM    202   CE1  PHE   30    -23.126  28.108  39.451  1.00   8.21
ATOM    203   CE2  PHE   30    -21.996  29.661  37.898  1.00   6.20
ATOM    204   CZ   PHE   30    -21.971  28.509  38.739  1.00   7.61
ATOM    205   N    VAL   31    -27.413  30.739  40.862  1.00   4.85
ATOM    206   CA   VAL   31    -27.751  30.017  42.118  1.00   6.26
ATOM    207   C    VAL   31    -27.445  28.530  41.828  1.00   6.68
ATOM    208   O    VAL   31    -27.515  28.036  40.680  1.00   4.79
ATOM    209   CB   VAL   31    -29.141  30.296  42.666  1.00   7.03
ATOM    210   CG1  VAL   31    -29.230  31.765  43.136  1.00  11.46
ATOM    211   CG2  VAL   31    -30.190  29.902  41.646  1.00   8.54
ATOM    212   N    THR   32    -27.150  27.786  42.910  1.00   5.51
ATOM    213   CA   THR   32    -26.762  26.373  42.892  1.00   7.30
ATOM    214   C    THR   32    -26.833  25.866  44.356  1.00   8.85
ATOM    215   O    THR   32    -27.382  26.568  45.240  1.00   6.58
ATOM    216   CB   THR   32    -25.318  26.271  42.249  1.00   6.85
ATOM    217   OG1  THR   32    -24.927  24.904  42.030  1.00   6.22
ATOM    218   CG2  THR   32    -24.141  26.895  43.109  1.00   4.90
ATOM    219   N    ALA   33    -26.318  24.676  44.619  1.00   8.92
ATOM    220   CA   ALA   33    -26.313  24.007  45.928  1.00   9.53
```

```
ATOM    221  C    ALA   33    -25.158  24.465  46.827  1.00   9.16
ATOM    222  O    ALA   33    -24.007  24.503  46.369  1.00   8.53
ATOM    223  CB   ALA   33    -26.294  22.473  45.773  1.00   7.77
ATOM    224  N    GLY   34    -25.408  24.724  48.076  1.00   7.16
ATOM    225  CA   GLY   34    -24.348  25.143  49.024  1.00   8.05
ATOM    226  C    GLY   34    -23.390  24.043  49.347  1.00   7.39
ATOM    227  O    GLY   34    -22.194  24.315  49.698  1.00   8.30
ATOM    228  N    HIS   35    -23.788  22.780  49.271  1.00   7.52
ATOM    229  CA   HIS   35    -22.821  21.714  49.636  1.00   6.58
ATOM    230  C    HIS   35    -21.744  21.601  48.560  1.00   8.95
ATOM    231  O    HIS   35    -20.702  20.945  48.747  1.00   8.96
ATOM    232  CB   HIS   35    -23.497  20.364  49.883  1.00   8.85
ATOM    233  CG   HIS   35    -23.991  19.599  48.686  1.00   6.87
ATOM    234  ND1  HIS   35    -25.305  19.481  48.321  1.00   8.56
ATOM    235  CD2  HIS   35    -23.326  18.872  47.769  1.00   5.55
ATOM    236  CE1  HIS   35    -25.414  18.744  47.228  1.00   7.54
ATOM    237  NE2  HIS   35    -24.217  18.313  46.906  1.00   8.64
ATOM    238  N    CYS   36    -21.930  22.183  47.376  1.00   8.15
ATOM    239  CA   CYS   36    -20.940  22.145  46.312  1.00   8.05
ATOM    240  C    CYS   36    -19.746  23.062  46.679  1.00  11.13
ATOM    241  O    CYS   36    -18.715  22.841  45.999  1.00  10.34
ATOM    242  CB   CYS   36    -21.518  22.598  44.977  1.00   5.97
ATOM    243  SG   CYS   36    -22.774  21.389  44.403  1.00   9.16
ATOM    244  N    GLY   37    -19.855  24.012  47.601  1.00   9.60
ATOM    245  CA   GLY   37    -18.632  24.821  47.862  1.00   8.52
ATOM    246  C    GLY   37    -18.853  25.793  48.998  1.00  11.72
ATOM    247  O    GLY   37    -19.923  26.350  49.153  1.00  12.57
ATOM    248  N    ARG   38    -17.807  26.044  49.767  1.00   9.44
ATOM    249  NH2  ARG   38    -13.066  27.478  54.730  0.00  41.69
ATOM    250  NH1  ARG   38    -14.258  25.862  55.765  0.00  42.03
ATOM    251  CZ   ARG   38    -13.968  26.494  54.619  0.00  41.38
ATOM    252  NE   ARG   38    -14.559  26.142  53.467  0.00  39.87
ATOM    253  CD   ARG   38    -15.763  25.165  53.320  0.00  37.50
ATOM    254  CG   ARG   38    -17.064  25.666  52.814  1.00  23.13
ATOM    255  CB   ARG   38    -16.602  26.727  51.799  1.00  14.90
ATOM    256  CA   ARG   38    -17.812  27.040  50.845  1.00  12.65
ATOM    257  C    ARG   38    -17.566  28.415  50.239  1.00  11.84
ATOM    258  O    ARG   38    -16.987  28.562  49.137  1.00  10.80
ATOM    259  N    VAL   39    -17.953  29.488  50.953  1.00  12.22
ATOM    260  CA   VAL   39    -17.723  30.881  50.483  1.00  11.55
ATOM    261  C    VAL   39    -16.224  31.002  50.149  1.00  11.46
ATOM    262  O    VAL   39    -15.406  30.540  50.944  1.00  12.65
ATOM    263  CB   VAL   39    -18.195  31.902  51.513  1.00  14.37
ATOM    264  CG1  VAL   39    -17.541  33.262  51.282  1.00  18.26
ATOM    265  CG2  VAL   39    -19.720  32.035  51.617  1.00  19.01
ATOM    266  N    GLY   40    -15.853  31.595  49.017  1.00  10.59
ATOM    267  CA   GLY   40    -14.467  31.715  48.658  1.00   9.21
ATOM    268  C    GLY   40    -13.962  30.690  47.689  1.00  11.61
ATOM    269  O    GLY   40    -12.904  30.954  47.066  1.00  13.99
ATOM    270  N    THR   41    -14.603  29.592  47.441  1.00  10.26
ATOM    271  CG2  THR   41    -14.886  26.180  45.550  1.00   8.90
ATOM    272  OG1  THR   41    -15.058  26.792  47.930  1.00  14.49
ATOM    273  CB   THR   41    -15.123  27.285  46.571  1.00  12.41
ATOM    274  CA   THR   41    -14.199  28.566  46.525  1.00   9.98
```

```
ATOM   275  C    THR  41     -14.360  29.148  45.121  1.00  11.13
ATOM   276  O    THR  41     -15.404  29.657  44.713  1.00  10.17
ATOM   277  N    GLN  42     -13.297  28.983  44.365  1.00  12.36
ATOM   278  NE2  GLN  42     -11.317  32.840  43.178  0.70  32.68
ATOM   279  OE1  GLN  42      -9.407  31.714  42.552  0.70  35.48
ATOM   280  CD   GLN  42     -10.512  31.791  43.080  0.70  30.29
ATOM   281  CG   GLN  42     -11.132  30.558  43.680  0.70  24.69
ATOM   282  CB   GLN  42     -11.801  29.729  42.592  0.70  18.80
ATOM   288  CA   GLN  42     -13.263  29.456  42.977  1.00  11.77
ATOM   289  C    GLN  42     -13.852  28.392  42.063  1.00  13.86
ATOM   290  O    GLN  42     -13.615  27.187  42.330  1.00  12.07
ATOM   291  N    VAL  43     -14.544  28.817  41.002  1.00  13.96
ATOM   292  CG2  VAL  43     -17.397  28.751  39.309  1.00  15.91
ATOM   293  CG1  VAL  43     -17.192  27.656  41.542  1.00  10.29
ATOM   294  CB   VAL  43     -16.657  27.731  40.117  1.00  14.08
ATOM   295  CA   VAL  43     -15.132  27.886  40.018  1.00  11.05
ATOM   296  C    VAL  43     -14.717  28.297  38.584  1.00  10.70
ATOM   297  O    VAL  43     -14.393  29.467  38.214  1.00   8.75
ATOM   298  N    THR  44     -14.726  27.266  37.757  1.00   8.19
ATOM   299  CG2  THR  44     -13.085  26.655  34.277  1.00  16.80
ATOM   300  OG1  THR  44     -12.054  27.080  36.423  1.00  14.72
ATOM   301  CB   THR  44     -13.232  26.536  35.773  1.00   7.96
ATOM   302  CA   THR  44     -14.459  27.387  36.328  1.00   8.95
ATOM   303  C    THR  44     -15.708  26.877  35.588  1.00  10.78
ATOM   304  O    THR  44     -16.155  25.743  35.947  1.00   9.00
ATOM   305  N    ILE  45     -16.219  27.660  34.626  1.00  10.77
ATOM   306  CA   ILE  45     -17.352  27.175  33.850  1.00  11.78
ATOM   307  C    ILE  45     -16.950  27.476  32.396  1.00  10.56
ATOM   308  O    ILE  45     -16.976  28.673  32.030  1.00  10.62
ATOM   309  CB   ILE  45     -18.743  27.767  34.312  1.00   8.73
ATOM   310  CG1  ILE  45     -19.767  27.359  33.217  1.00  14.25
ATOM   311  CG2  ILE  45     -18.635  29.300  34.483  1.00  14.91
ATOM   312  CD1  ILE  45     -21.239  27.351  33.717  1.00  17.74
ATOM   313  N    GLY  46     -16.588  26.493  31.623  1.00  11.49
ATOM   314  CA   GLY  46     -16.162  26.796  30.214  1.00  13.72
ATOM   315  C    GLY  46     -15.009  27.812  30.282  1.00  12.34
ATOM   316  O    GLY  46     -14.011  27.661  31.002  1.00  14.15
ATOM   317  N    ASN  47     -15.134  28.895  29.512  1.00  13.14
ATOM   318  ND2  ASN  47     -15.075  31.342  26.221  1.00  26.89
ATOM   319  OD1  ASN  47     -16.257  31.266  28.086  1.00  18.12
ATOM   320  CG   ASN  47     -15.180  31.045  27.520  1.00  19.67
ATOM   321  CB   ASN  47     -13.914  30.476  28.081  1.00  17.20
ATOM   322  CA   ASN  47     -14.106  29.967  29.522  1.00  14.86
ATOM   323  C    ASN  47     -14.409  31.129  30.484  1.00  14.20
ATOM   324  O    ASN  47     -13.929  32.264  30.367  1.00  16.69
ATOM   325  N    GLY  48     -15.234  30.900  31.476  1.00  11.79
ATOM   326  CA   GLY  48     -15.629  31.860  32.487  1.00  10.60
ATOM   327  C    GLY  48     -15.114  31.350  33.840  1.00   8.68
ATOM   328  O    GLY  48     -14.741  30.180  34.021  1.00   8.85
ATOM   329  N    ARG  49     -15.067  32.286  34.782  1.00   8.71
ATOM   330  NH2  ARG  49     -10.753  29.684  38.714  0.00  43.61
ATOM   331  NH1  ARG  49      -9.430  30.717  37.086  0.00  39.51
ATOM   332  CZ   ARG  49     -10.647  30.223  37.466  0.00  42.12
ATOM   333  NE   ARG  49     -11.803  30.174  36.714  0.00  38.98
```

```
ATOM    334  CD  ARG    49     -11.625  30.774  35.625  1.00 24.44
ATOM    335  CG  ARG    49     -12.079  32.161  35.395  1.00 20.17
ATOM    336  CB  ARG    49     -13.190  32.537  36.355  1.00 13.15
ATOM    337  CA  ARG    49     -14.600  31.985  36.143  1.00  8.87
ATOM    338  C   ARG    49     -15.485  32.746  37.136  1.00  9.56
ATOM    339  O   ARG    49     -16.026  33.814  36.747  1.00 10.73
ATOM    340  N   GLY    50     -15.644  32.236  38.337  1.00 10.04
ATOM    341  CA  GLY    50     -16.416  32.933  39.372  1.00  6.68
ATOM    342  C   GLY    50     -15.985  32.438  40.758  1.00  7.46
ATOM    343  O   GLY    50     -15.035  31.654  40.838  1.00  8.57
ATOM    344  N   VAL    51     -16.755  32.885  41.756  1.00  9.13
ATOM    345  CG2 VAL    51     -15.047  33.181  45.219  1.00  9.31
ATOM    346  CG1 VAL    51     -16.041  34.936  43.760  1.00  9.54
ATOM    347  CB  VAL    51     -15.469  33.510  43.768  1.00 10.40
ATOM    348  CA  VAL    51     -16.439  32.474  43.145  1.00  8.97
ATOM    349  C   VAL    51     -17.739  32.363  43.951  1.00  8.46
ATOM    350  O   VAL    51     -18.657  33.166  43.726  1.00  8.01
ATOM    351  N   PHE    52     -17.778  31.394  44.846  1.00  7.71
ATOM    352  CD2 PHE    52     -20.510  28.198  46.287  1.00  7.34
ATOM    353  CE2 PHE    52     -20.952  27.038  45.614  1.00 12.48
ATOM    354  CZ  PHE    52     -20.103  26.415  44.672  1.00 11.92
ATOM    355  CE1 PHE    52     -18.857  26.983  44.355  1.00  8.56
ATOM    356  CD1 PHE    52     -18.454  28.151  45.012  1.00  7.30
ATOM    357  CG  PHE    52     -19.269  28.765  45.964  1.00 10.46
ATOM    358  CB  PHE    52     -18.820  30.015  46.703  1.00  9.22
ATOM    359  CA  PHE    52     -18.916  31.237  45.766  1.00  9.28
ATOM    360  C   PHE    52     -18.928  32.498  46.637  1.00 10.41
ATOM    361  O   PHE    52     -17.979  32.752  47.403  1.00 10.33
ATOM    362  N   GLU    53     -20.038  33.239  46.481  1.00  8.81
ATOM    363  OE2 GLU    53     -22.012  37.756  45.426  1.00 27.06
ATOM    364  OE1 GLU    53     -21.229  39.265  46.722  1.00 33.78
ATOM    365  CD  GLU    53     -21.338  38.087  46.413  1.00 28.63
ATOM    366  CG  GLU    53     -20.701  36.961  47.162  1.00 15.08
ATOM    367  CB  GLU    53     -20.818  35.612  46.441  1.00 10.91
ATOM    368  CA  GLU    53     -20.172  34.475  47.239  1.00 10.55
ATOM    369  C   GLU    53     -21.035  34.208  48.485  1.00 13.01
ATOM    370  O   GLU    53     -20.664  34.743  49.558  1.00 11.89
ATOM    371  N   GLN    54     -22.095  33.444  48.352  1.00  9.12
ATOM    372  NE2 GLN    54     -26.256  36.329  49.251  1.00 43.84
ATOM    373  OE1 GLN    54     -25.933  35.594  51.419  1.00 46.53
ATOM    374  CD  GLN    54     -25.586  35.741  50.241  1.00 40.72
ATOM    375  CG  GLN    54     -24.256  35.205  49.756  1.00 29.81
ATOM    376  CB  GLN    54     -24.346  33.707  49.555  1.00 17.82
ATOM    377  CA  GLN    54     -22.955  33.105  49.508  1.00 10.81
ATOM    378  C   GLN    54     -23.164  31.600  49.527  1.00 12.82
ATOM    379  O   GLN    54     -23.418  31.101  48.410  1.00 13.75
ATOM    380  N   SER    55     -23.074  30.926  50.665  1.00 10.56
ATOM    381  OG  SER    55     -22.169  27.372  50.204  1.00 14.02
ATOM    382  CB  SER    55     -21.995  28.781  50.228  1.00  9.88
ATOM    383  CA  SER    55     -23.280  29.470  50.637  1.00 11.20
ATOM    384  C   SER    55     -23.730  28.998  52.014  1.00 12.70
ATOM    385  O   SER    55     -23.084  29.298  53.011  1.00 11.84
ATOM    386  N   VAL    56     -24.824  28.274  52.086  1.00 11.38
ATOM    387  CA  VAL    56     -25.345  27.735  53.342  1.00  9.56
```

```
ATOM    388  C    VAL    56     -25.516  26.223  53.218  1.00  11.47
ATOM    389  O    VAL    56     -26.250  25.756  52.302  1.00  10.80
ATOM    390  CB   VAL    56     -26.691  28.365  53.715  1.00  12.57
ATOM    391  CG1  VAL    56     -27.250  27.561  54.895  1.00  13.65
ATOM    392  CG2  VAL    56     -26.542  29.809  54.111  1.00  14.61
ATOM    393  N    PHE    57     -24.903  25.475  54.116  1.00   9.44
ATOM    394  CA   PHE    57     -25.035  24.030  54.173  1.00  10.86
ATOM    395  C    PHE    57     -24.351  23.597  55.503  1.00  12.68
ATOM    396  O    PHE    57     -23.200  24.057  55.632  1.00  14.31
ATOM    397  CB   PHE    57     -24.383  23.289  52.962  1.00   9.20
ATOM    398  CG   PHE    57     -24.530  21.797  53.071  1.00   7.41
ATOM    399  CD1  PHE    57     -23.489  20.999  53.547  1.00  10.87
ATOM    400  CD2  PHE    57     -25.748  21.211  52.762  1.00  10.76
ATOM    401  CE1  PHE    57     -23.654  19.621  53.690  1.00  16.75
ATOM    402  CE2  PHE    57     -25.948  19.851  52.869  1.00   9.80
ATOM    403  CZ   PHE    57     -24.897  19.033  53.326  1.00  17.07
ATOM    404  N    PRO    58     -24.888  22.759  56.355  1.00  11.76
ATOM    405  CA   PRO    58     -26.182  22.082  56.294  1.00  11.15
ATOM    406  C    PRO    58     -27.302  22.967  56.755  1.00   9.63
ATOM    407  O    PRO    58     -27.072  24.207  56.657  1.00  10.82
ATOM    408  CB   PRO    58     -25.955  20.768  57.043  1.00  11.03
ATOM    409  CG   PRO    58     -24.947  21.178  58.078  1.00  12.71
ATOM    410  CD   PRO    58     -24.125  22.322  57.531  1.00  12.73
ATOM    411  N    GLY    59     -28.466  22.432  57.103  1.00  10.97
ATOM    412  CA   GLY    59     -29.594  23.338  57.495  1.00  11.26
ATOM    413  C    GLY    59     -30.330  23.680  56.200  1.00  10.98
ATOM    414  O    GLY    59     -31.477  23.240  56.091  1.00  11.30
ATOM    415  N    ASN    60     -29.767  24.482  55.291  1.00  10.66
ATOM    416  CA   ASN    60     -30.400  24.729  53.962  1.00   8.17
ATOM    417  C    ASN    60     -29.377  24.099  52.981  1.00   9.56
ATOM    418  O    ASN    60     -28.346  23.532  53.474  1.00   8.76
ATOM    419  CB   ASN    60     -30.598  26.175  53.595  1.00   9.50
ATOM    420  CG   ASN    60     -31.369  26.934  54.664  1.00  12.19
ATOM    421  OD1  ASN    60     -30.872  27.984  55.082  1.00  16.81
ATOM    422  ND2  ASN    60     -32.478  26.340  55.060  1.00  15.11
ATOM    423  N    ASP    61     -29.582  24.193  51.661  1.00   7.15
ATOM    424  CA   ASP    61     -28.544  23.661  50.701  1.00   7.83
ATOM    425  C    ASP    61     -28.598  24.692  49.547  1.00   8.69
ATOM    426  O    ASP    61     -29.213  24.393  48.519  1.00   7.71
ATOM    427  CB   ASP    61     -28.818  22.216  50.313  1.00   4.48
ATOM    428  CG   ASP    61     -27.637  21.575  49.640  1.00   6.18
ATOM    429  OD1  ASP    61     -27.591  20.419  49.245  1.00   6.86
ATOM    430  OD2  ASP    61     -26.622  22.316  49.431  1.00   8.20
ATOM    431  N    ALA    62     -28.041  25.868  49.751  1.00   7.72
ATOM    432  CB   ALA    62     -29.258  27.857  49.385  1.00   8.64
ATOM    433  CA   ALA    62     -28.134  26.967  48.775  1.00   8.98
ATOM    434  C    ALA    62     -26.880  27.802  48.618  1.00   9.19
ATOM    435  O    ALA    62     -26.114  27.939  49.618  1.00  10.25
ATOM    436  N    ALA    63     -26.667  28.360  47.434  1.00   7.69
ATOM    437  CA   ALA    63     -25.476  29.189  47.173  1.00   7.50
ATOM    438  C    ALA    63     -25.668  30.110  45.987  1.00   7.33
ATOM    439  O    ALA    63     -26.526  29.843  45.116  1.00   6.36
ATOM    440  CB   ALA    63     -24.247  28.263  46.886  1.00   4.57
ATOM    441  N    PHE    64     -24.889  31.172  45.985  1.00   8.23
```

```
ATOM    442  CD2 PHE    64     -24.221  35.364  43.942  1.00   6.73
ATOM    443  CE2 PHE    64     -24.051  36.237  42.841  1.00   7.23
ATOM    444  CZ  PHE    64     -25.063  36.205  41.842  1.00   6.08
ATOM    445  CE1 PHE    64     -26.166  35.352  41.959  1.00  10.30
ATOM    446  CD1 PHE    64     -26.263  34.453  43.038  1.00  10.04
ATOM    447  CG  PHE    64     -25.287  34.477  44.027  1.00   6.69
ATOM    448  CB  PHE    64     -25.415  33.537  45.240  1.00   6.42
ATOM    449  CA  PHE    64     -24.840  32.152  44.922  1.00   7.87
ATOM    450  C   PHE    64     -23.351  32.196  44.518  1.00  10.06
ATOM    451  O   PHE    64     -22.454  32.478  45.362  1.00  10.39
ATOM    452  N   VAL    65     -23.080  31.952  43.234  1.00   8.61
ATOM    453  CA  VAL    65     -21.722  32.028  42.662  1.00   8.62
ATOM    454  C   VAL    65     -21.686  33.327  41.831  1.00   8.89
ATOM    455  O   VAL    65     -22.514  33.548  40.948  1.00   7.44
ATOM    456  CB  VAL    65     -21.338  30.840  41.722  1.00  11.34
ATOM    457  CG1 VAL    65     -20.018  31.055  40.967  1.00  10.37
ATOM    458  CG2 VAL    65     -21.333  29.530  42.493  1.00   9.94
ATOM    459  N   ARG    66     -20.744  34.213  42.094  1.00   6.55
ATOM    460  NH2 ARG    66     -16.111  39.098  43.470  1.00  18.29
ATOM    461  NH1 ARG    66     -17.309  39.979  41.747  1.00  18.67
ATOM    462  CZ  ARG    66     -17.271  39.260  42.832  1.00  18.74
ATOM    463  NE  ARG    66     -18.308  38.673  43.409  1.00  22.97
ATOM    464  CD  ARG    66     -19.672  38.751  42.950  1.00  23.13
ATOM    465  CG  ARG    66     -19.916  37.827  41.797  1.00  18.33
ATOM    466  CB  ARG    66     -19.949  36.464  42.422  1.00  12.11
ATOM    467  CA  ARG    66     -20.545  35.475  41.416  1.00   8.00
ATOM    468  C   ARG    66     -19.501  35.310  40.305  1.00   7.85
ATOM    469  O   ARG    66     -18.447  34.738  40.557  1.00   8.51
ATOM    470  N   GLY    67     -19.828  35.857  39.132  1.00   8.23
ATOM    471  CA  GLY    67     -18.921  35.779  37.962  1.00   3.28
ATOM    472  C   GLY    67     -17.838  36.834  38.114  1.00   7.11
ATOM    473  O   GLY    67     -18.123  38.019  38.332  1.00   9.23
ATOM    474  N   THR    68     -16.585  36.418  37.933  1.00   6.19
ATOM    475  CA  THR    68     -15.407  37.292  37.994  1.00   6.13
ATOM    476  C   THR    68     -14.784  37.468  36.611  1.00  10.55
ATOM    477  O   THR    68     -13.939  38.358  36.375  1.00   9.20
ATOM    478  CB  THR    68     -14.366  36.832  39.071  1.00  13.02
ATOM    479  OG1 THR    68     -13.865  35.569  38.579  1.00   9.29
ATOM    480  CG2 THR    68     -14.870  36.773  40.522  1.00  11.87
ATOM    481  N   SER    69     -15.205  36.672  35.618  1.00  12.02
ATOM    482  CA  SER    69     -14.736  36.796  34.233  1.00  11.62
ATOM    483  C   SER    69     -15.660  36.069  33.264  1.00  12.37
ATOM    484  O   SER    69     -15.911  34.865  33.480  1.00  11.23
ATOM    485  CB  SER    69     -13.337  36.184  34.027  1.00  12.32
ATOM    486  OG  SER    69     -12.823  36.389  32.763  1.00  15.07
ATOM    487  N   ASN    70     -16.100  36.767  32.236  1.00  12.58
ATOM    488  ND2 ASN    70     -16.685  36.201  28.330  1.00  20.03
ATOM    489  OD1 ASN    70     -15.425  34.370  28.194  1.00  19.07
ATOM    490  CG  ASN    70     -15.954  35.243  28.878  1.00  14.54
ATOM    491  CB  ASN    70     -15.848  35.335  30.379  1.00   8.27
ATOM    492  CA  ASN    70     -16.894  36.195  31.131  1.00  11.17
ATOM    493  C   ASN    70     -18.166  35.424  31.400  1.00  10.53
ATOM    494  O   ASN    70     -18.343  34.319  30.817  1.00  14.17
ATOM    495  N   PHE    71     -19.048  35.946  32.209  1.00   8.98
```

```
ATOM    496  CD2  PHE   71     -21.139  34.054  36.002  1.00   5.72
ATOM    497  CE2  PHE   71     -20.735  33.063  36.900  1.00   7.44
ATOM    498  CZ   PHE   71     -19.483  32.395  36.669  1.00  10.35
ATOM    499  CE1  PHE   71     -18.713  32.681  35.550  1.00  10.41
ATOM    500  CD1  PHE   71     -19.159  33.681  34.652  1.00   9.67
ATOM    501  CG   PHE   71     -20.350  34.372  34.873  1.00   5.76
ATOM    502  CB   PHE   71     -20.839  35.417  33.897  1.00   7.11
ATOM    503  CA   PHE   71     -20.346  35.257  32.435  1.00  10.26
ATOM    504  C    PHE   71     -21.337  35.958  31.503  1.00  11.61
ATOM    505  O    PHE   71     -21.429  37.207  31.537  1.00  14.68
ATOM    506  N    THR   72     -22.071  35.275  30.691  1.00  11.03
ATOM    507  CA   THR   72     -23.133  35.902  29.860  1.00   9.26
ATOM    508  C    THR   72     -24.405  35.261  30.425  1.00   9.51
ATOM    509  O    THR   72     -24.562  34.027  30.269  1.00  11.35
ATOM    510  CB   THR   72     -23.036  35.596  28.328  1.00  15.61
ATOM    511  OG1  THR   72     -21.768  36.189  27.928  1.00  15.86
ATOM    512  CG2  THR   72     -24.177  36.178  27.494  1.00  14.54
ATOM    513  N    LEU   73     -25.282  36.028  31.020  1.00  11.12
ATOM    514  CA   LEU   73     -26.502  35.479  31.608  1.00   9.31
ATOM    515  C    LEU   73     -27.504  35.184  30.484  1.00   9.04
ATOM    516  O    LEU   73     -27.563  35.896  29.460  1.00   8.44
ATOM    517  CB   LEU   73     -27.046  36.412  32.687  1.00   8.84
ATOM    518  CG   LEU   73     -26.215  36.869  33.883  1.00  13.85
ATOM    519  CD1  LEU   73     -27.074  37.521  34.968  1.00  12.85
ATOM    520  CD2  LEU   73     -25.471  35.702  34.530  1.00   9.85
ATOM    521  N    THR   74     -28.295  34.161  30.737  1.00   7.42
ATOM    522  CG2  THR   74     -27.696  32.554  28.200  1.00   3.40
ATOM    523  OG1  THR   74     -29.174  31.283  29.642  1.00   9.42
ATOM    524  CB   THR   74     -29.063  32.532  28.922  1.00   7.73
ATOM    525  CA   THR   74     -29.389  33.735  29.859  1.00   7.40
ATOM    526  C    THR   74     -30.600  33.347  30.732  1.00  10.05
ATOM    527  O    THR   74     -30.473  33.184  31.959  1.00   7.44
ATOM    528  N    ASN   75     -31.775  33.201  30.069  1.00   8.53
ATOM    529  ND2  ASN   75     -36.021  33.747  28.974  1.00  14.07
ATOM    530  OD1  ASN   75     -33.929  33.279  28.252  1.00  14.16
ATOM    531  CG   ASN   75     -34.723  33.526  29.157  1.00  15.69
ATOM    532  CB   ASN   75     -34.178  33.518  30.570  1.00  11.17
ATOM    533  CA   ASN   75     -32.924  32.729  30.849  1.00   9.39
ATOM    534  C    ASN   75     -33.156  31.252  30.465  1.00  10.95
ATOM    535  O    ASN   75     -34.322  30.835  30.620  1.00  13.03
ATOM    536  N    LEU   76     -32.177  30.516  29.993  1.00   7.99
ATOM    537  CD2  LEU   76     -32.993  29.592  26.412  1.00  11.04
ATOM    538  CD1  LEU   76     -30.530  29.917  26.112  1.00  13.41
ATOM    539  CG   LEU   76     -31.687  29.987  27.082  1.00  11.12
ATOM    540  CB   LEU   76     -31.416  29.013  28.250  1.00  10.63
ATOM    541  CA   LEU   76     -32.315  29.158  29.530  1.00   8.79
ATOM    542  C    LEU   76     -31.876  28.059  30.512  1.00   8.97
ATOM    543  O    LEU   76     -31.038  28.290  31.385  1.00   6.01
ATOM    544  N    VAL   77     -32.529  26.936  30.323  1.00   8.54
ATOM    545  CA   VAL   77     -32.285  25.689  31.062  1.00   8.05
ATOM    546  C    VAL   77     -32.125  24.578  29.973  1.00   9.00
ATOM    547  O    VAL   77     -33.126  24.380  29.178  1.00   6.78
ATOM    548  CB   VAL   77     -33.397  25.290  32.052  1.00   8.09
ATOM    549  CG1  VAL   77     -33.049  23.911  32.715  1.00   5.84
```

```
ATOM    550  CG2 VAL   77     -33.575  26.350  33.142  1.00 10.07
ATOM    551  N   SER   78     -31.017  23.871  29.974  1.00  8.67
ATOM    552  OG  SER   78     -29.161  21.344  27.899  1.00  9.85
ATOM    553  CB  SER   78     -29.355  22.409  28.857  1.00 12.29
ATOM    554  CA  SER   78     -30.831  22.814  28.929  1.00  8.23
ATOM    555  C   SER   78     -31.710  21.583  29.189  1.00  9.82
ATOM    556  O   SER   78     -31.759  21.055  30.305  1.00  7.69
ATOM    557  N   ARG   79     -32.337  21.082  28.116  1.00  9.80
ATOM    558  NH2 ARG   79     -37.443  22.028  24.212  1.00 31.34
ATOM    559  NH1 ARG   79     -38.500  22.780  26.184  1.00 27.56
ATOM    560  CZ  ARG   79     -37.601  21.991  25.554  1.00 28.07
ATOM    561  NE  ARG   79     -36.785  21.131  26.161  1.00 21.89
ATOM    562  CD  ARG   79     -36.718  20.936  27.589  1.00 18.78
ATOM    563  CG  ARG   79     -35.265  21.118  27.992  1.00  9.14
ATOM    564  CB  ARG   79     -34.499  19.957  27.396  1.00  7.07
ATOM    565  CA  ARG   79     -33.163  19.879  28.166  1.00 10.01
ATOM    566  C   ARG   79     -32.272  18.740  27.659  1.00 11.09
ATOM    567  O   ARG   79     -32.799  17.622  27.476  1.00 11.76
ATOM    568  N   TYR   80     -30.980  18.901  27.456  1.00 10.89
ATOM    569  OH  TYR   80     -25.669  19.608  31.411  1.00 13.70
ATOM    570  CD2 TYR   80     -28.969  18.626  30.175  1.00  8.55
ATOM    571  CE2 TYR   80     -28.018  19.277  30.962  1.00  9.07
ATOM    572  CZ  TYR   80     -26.667  19.006  30.683  1.00 13.15
ATOM    573  CE1 TYR   80     -26.290  18.103  29.673  1.00 13.12
ATOM    574  CD1 TYR   80     -27.305  17.481  28.921  1.00 12.00
ATOM    575  CG  TYR   80     -28.646  17.742  29.153  1.00 10.87
ATOM    576  CB  TYR   80     -29.686  17.010  28.331  1.00 11.71
ATOM    577  CA  TYR   80     -30.100  17.809  27.036  1.00 13.19
ATOM    578  C   TYR   80     -30.669  16.889  25.939  1.00 15.57
ATOM    579  O   TYR   80     -31.074  17.414  24.848  1.00 16.53
ATOM    580  N   ASN   81     -30.732  15.583  26.157  1.00 15.67
ATOM    581  ND2 ASN   81     -30.251  12.075  23.672  0.50 23.42
ATOM    582  OD1 ASN   81     -31.653  10.851  24.930  0.50 22.68
ATOM    583  CG  ASN   81     -31.012  11.924  24.769  0.50 24.69
ATOM    584  CB  ASN   81     -30.915  13.117  25.699  0.50 20.33
ATOM    589  CA  ASN   81     -31.169  14.536  25.163  1.00 17.67
ATOM    590  C   ASN   81     -32.611  14.689  24.807  1.00 18.70
ATOM    591  O   ASN   81     -33.067  14.207  23.731  1.00 20.41
ATOM    592  N   THR   82     -33.405  15.385  25.621  1.00 15.25
ATOM    593  CG2 THR   82     -36.933  16.845  26.136  1.00 15.50
ATOM    594  OG1 THR   82     -35.944  14.838  27.235  1.00 15.80
ATOM    595  CB  THR   82     -35.663  16.070  26.495  1.00 13.76
ATOM    596  CA  THR   82     -34.787  15.661  25.275  1.00 16.61
ATOM    597  C   THR   82     -34.775  16.712  24.128  1.00 19.57
ATOM    598  O   THR   82     -35.725  16.765  23.314  1.00 20.18
ATOM    599  N   GLY   83     -33.765  17.555  23.973  1.00 17.44
ATOM    600  CA  GLY   83     -33.611  18.551  22.941  1.00 16.21
ATOM    601  C   GLY   83     -34.082  19.964  23.286  1.00 12.64
ATOM    602  O   GLY   83     -35.127  20.225  23.908  1.00 12.83
ATOM    603  N   GLY   84     -33.281  20.926  22.859  1.00 11.84
ATOM    604  CA  GLY   84     -33.604  22.331  23.082  1.00 11.09
ATOM    605  C   GLY   84     -33.492  22.741  24.541  1.00  9.78
ATOM    606  O   GLY   84     -32.796  22.177  25.384  1.00 10.83
ATOM    607  N   TYR   85     -34.104  23.875  24.825  1.00 10.88
```

```
ATOM    608  OH   TYR    85     -28.004   24.555   24.203  1.00  18.98
ATOM    609  CD2  TYR    85     -31.561   25.395   24.068  1.00  12.07
ATOM    610  CE2  TYR    85     -30.266   25.023   23.693  1.00  13.73
ATOM    611  CZ   TYR    85     -29.263   24.890   24.644  1.00  15.05
ATOM    612  CE1  TYR    85     -29.519   25.081   26.012  1.00  12.94
ATOM    613  CD1  TYR    85     -30.826   25.421   26.395  1.00  12.96
ATOM    614  CG   TYR    85     -31.850   25.570   25.445  1.00  11.64
ATOM    615  CB   TYR    85     -33.264   25.866   25.882  1.00  10.50
ATOM    616  CA   TYR    85     -34.079   24.539   26.116  1.00  10.86
ATOM    617  C    TYR    85     -35.418   25.002   26.674  1.00  13.82
ATOM    618  O    TYR    85     -36.268   25.491   25.854  1.00  14.41
ATOM    619  N    ALA    86     -35.569   24.891   27.969  1.00   9.86
ATOM    620  CB   ALA    86     -37.046   24.630   29.971  1.00   9.75
ATOM    621  CA   ALA    86     -36.735   25.425   28.695  1.00  11.67
ATOM    622  C    ALA    86     -36.361   26.918   28.958  1.00  11.87
ATOM    623  O    ALA    86     -35.188   27.341   28.972  1.00   9.92
ATOM    624  N    THR    87     -37.345   27.829   29.131  1.00  10.43
ATOM    625  CG2  THR    87     -36.841   29.875   26.861  1.00  17.11
ATOM    626  OG1  THR    87     -38.959   29.934   28.083  1.00  17.19
ATOM    627  CB   THR    87     -37.539   30.174   28.200  1.00  17.24
ATOM    628  CA   THR    87     -37.057   29.241   29.379  1.00  10.64
ATOM    629  C    THR    87     -37.640   29.593   30.724  1.00  11.34
ATOM    630  O    THR    87     -38.696   29.055   31.041  1.00  13.09
ATOM    631  N    VAL    88     -37.001   30.448   31.521  1.00  10.66
ATOM    632  CA   VAL    88     -37.441   30.863   32.856  1.00   9.45
ATOM    633  C    VAL    88     -38.255   32.155   32.696  1.00  11.88
ATOM    634  O    VAL    88     -37.698   33.094   32.136  1.00  10.63
ATOM    635  CB   VAL    88     -36.246   31.053   33.821  1.00   7.00
ATOM    636  CG1  VAL    88     -36.652   31.636   35.192  1.00   5.32
ATOM    637  CG2  VAL    88     -35.478   29.746   33.985  1.00   9.05
ATOM    638  N    ALA    89     -39.467   32.233   33.201  1.00  10.89
ATOM    639  CB   ALA    89     -41.539   33.201   32.260  1.00   9.11
ATOM    640  CA   ALA    89     -40.325   33.440   33.132  1.00  11.01
ATOM    641  C    ALA    89     -40.690   33.918   34.548  1.00  11.13
ATOM    642  O    ALA    89     -41.242   35.028   34.655  1.00  13.90
ATOM    643  N    GLY    90     -40.351   33.181   35.617  1.00   9.54
ATOM    644  CA   GLY    90     -40.632   33.592   36.976  1.00   8.75
ATOM    645  C    GLY    90     -40.322   32.409   37.921  1.00  10.19
ATOM    646  O    GLY    90     -39.660   31.477   37.500  1.00   9.62
ATOM    647  N    HIS    91     -40.857   32.540   39.135  1.00  11.81
ATOM    648  CD2  HIS    91     -40.073   33.404   43.018  1.00  18.32
ATOM    649  NE2  HIS    91     -40.052   34.763   43.177  1.00  17.97
ATOM    650  CE1  HIS    91     -39.622   35.366   42.127  1.00  17.17
ATOM    651  ND1  HIS    91     -39.350   34.411   41.259  1.00  16.07
ATOM    652  CG   HIS    91     -39.605   33.184   41.765  1.00  16.04
ATOM    653  CB   HIS    91     -39.411   31.883   41.060  1.00  11.82
ATOM    654  CA   HIS    91     -40.637   31.530   40.180  1.00  10.58
ATOM    655  C    HIS    91     -41.854   31.229   41.025  1.00  12.38
ATOM    656  O    HIS    91     -41.723   31.032   42.248  1.00  13.11
ATOM    657  N    ASN    92     -43.013   31.126   40.369  1.00  12.16
ATOM    658  ND2  ASN    92     -46.608   32.760   41.360  1.00  44.37
ATOM    659  OD1  ASN    92     -45.564   33.225   39.385  1.00  40.52
ATOM    660  CG   ASN    92     -45.903   32.418   40.259  1.00  35.33
ATOM    661  CB   ASN    92     -45.524   30.938   40.252  1.00  23.82
```

```
ATOM    662  CA  ASN    92     -44.261  30.746  41.119  1.00 13.35
ATOM    663  C   ASN    92     -44.164  29.268  41.493  1.00 12.66
ATOM    664  O   ASN    92     -43.930  28.437  40.582  1.00 11.76
ATOM    665  N   GLN    93     -44.364  28.935  42.749  1.00 11.08
ATOM    666  NE2 GLN    93     -42.340  27.432  47.693  1.00 21.50
ATOM    667  OE1 GLN    93     -44.559  27.501  47.458  1.00 31.26
ATOM    668  CD  GLN    93     -43.422  27.632  46.972  1.00 27.63
ATOM    669  CG  GLN    93     -43.291  28.002  45.511  1.00 20.72
ATOM    670  CB  GLN    93     -44.409  27.379  44.700  1.00 15.24
ATOM    671  CA  GLN    93     -44.262  27.516  43.171  1.00 12.74
ATOM    672  C   GLN    93     -45.394  26.705  42.566  1.00 13.82
ATOM    673  O   GLN    93     -46.572  27.162  42.672  1.00 15.94
ATOM    674  N   ALA    94     -45.166  25.549  42.048  1.00 11.74
ATOM    675  CA  ALA    94     -46.178  24.676  41.481  1.00 11.41
ATOM    676  C   ALA    94     -46.815  23.934  42.649  1.00 14.20
ATOM    677  O   ALA    94     -46.120  23.587  43.637  1.00 14.08
ATOM    678  CB  ALA    94     -45.495  23.704  40.529  1.00  6.58
ATOM    679  N   PRO    95     -48.112  23.645  42.551  1.00 14.96
ATOM    680  CG  PRO    95     -50.259  23.275  41.661  1.00 15.96
ATOM    681  CD  PRO    95     -48.954  24.020  41.412  1.00 15.38
ATOM    682  CB  PRO    95     -50.261  22.810  43.087  1.00 13.99
ATOM    683  CA  PRO    95     -48.815  22.843  43.571  1.00 13.77
ATOM    684  C   PRO    95     -48.308  21.414  43.670  1.00 12.85
ATOM    685  O   PRO    95     -47.789  20.722  42.764  1.00 13.21
ATOM    686  N   ILE    96     -48.439  20.860  44.892  1.00  9.64
ATOM    687  CD1 ILE    96     -46.305  19.698  47.937  1.00 20.39
ATOM    688  CG1 ILE    96     -47.785  19.940  47.690  1.00 17.20
ATOM    689  CB  ILE    96     -48.425  19.023  46.634  1.00 13.72
ATOM    690  CG2 ILE    96     -48.131  17.530  46.952  1.00 17.91
ATOM    691  CA  ILE    96     -48.058  19.444  45.141  1.00 11.51
ATOM    692  C   ILE    96     -48.841  18.627  44.138  1.00 13.14
ATOM    693  O   ILE    96     -50.052  18.979  43.880  1.00 15.21
ATOM    694  N   GLY    97     -48.332  17.575  43.528  1.00 10.18
ATOM    695  CA  GLY    97     -49.020  16.783  42.537  1.00  9.00
ATOM    696  C   GLY    97     -48.645  17.200  41.126  1.00 11.33
ATOM    697  O   GLY    97     -48.867  16.374  40.221  1.00 12.32
ATOM    698  N   SER    98     -48.108  18.393  40.935  1.00 10.97
ATOM    699  OG  SER    98     -48.122  21.262  40.073  0.70 15.96
ATOM    700  CB  SER    98     -47.149  20.355  39.724  0.70 13.01
ATOM    703  CA  SER    98     -47.643  18.918  39.637  1.00 11.70
ATOM    704  C   SER    98     -46.376  18.198  39.140  1.00 11.01
ATOM    705  O   SER    98     -45.567  17.708  39.906  1.00 12.53
ATOM    706  N   SER    99     -46.203  18.149  37.825  1.00  8.54
ATOM    707  OG  SER    99     -45.372  18.423  34.957  1.00 12.93
ATOM    708  CB  SER    99     -45.157  17.258  35.747  1.00  7.78
ATOM    709  CA  SER    99     -45.010  17.562  37.226  1.00  8.54
ATOM    710  C   SER    99     -43.921  18.659  37.391  1.00  7.90
ATOM    711  O   SER    99     -44.195  19.884  37.534  1.00 10.31
ATOM    712  N   VAL   100     -42.675  18.231  37.384  1.00  9.21
ATOM    713  CA  VAL   100     -41.468  19.082  37.505  1.00  5.59
ATOM    714  C   VAL   100     -40.375  18.343  36.773  1.00  5.35
ATOM    715  O   VAL   100     -40.380  17.108  36.785  1.00  9.03
ATOM    716  CB  VAL   100     -41.112  19.395  38.979  1.00  5.88
ATOM    717  CG1 VAL   100     -40.630  18.114  39.670  1.00  8.61
```

```
ATOM    718  CG2 VAL 100     -40.142  20.579  39.127  1.00  5.24
ATOM    719  N   CYS 101     -39.423  19.055  36.168  1.00  5.24
ATOM    720  CA  CYS 101     -38.304  18.494  35.437  1.00  4.35
ATOM    721  C   CYS 101     -36.989  18.996  36.086  1.00  5.37
ATOM    722  O   CYS 101     -36.984  20.152  36.529  1.00  8.17
ATOM    723  CB  CYS 101     -38.312  18.824  33.935  1.00  5.99
ATOM    724  SG  CYS 101     -39.723  18.001  33.063  1.00  8.35
ATOM    725  N   ARG 102     -35.982  18.175  36.084  1.00  6.08
ATOM    726  CA  ARG 102     -34.649  18.527  36.587  1.00  7.57
ATOM    727  C   ARG 102     -33.605  18.534  35.462  1.00  8.71
ATOM    728  O   ARG 102     -33.604  17.647  34.598  1.00  8.00
ATOM    729  CB  ARG 102     -34.261  17.489  37.655  1.00  4.69
ATOM    730  CG  ARG 102     -32.859  17.784  38.286  1.00  3.27
ATOM    731  CD  ARG 102     -32.303  16.653  39.077  1.00  6.25
ATOM    732  NE  ARG 102     -32.250  15.402  38.343  1.00  7.04
ATOM    733  CZ  ARG 102     -31.471  15.083  37.294  1.00  9.62
ATOM    734  NH1 ARG 102     -31.692  13.864  36.773  1.00  9.55
ATOM    735  NH2 ARG 102     -30.608  15.953  36.805  1.00  5.91
ATOM    736  N   SER 103     -32.662  19.454  35.404  1.00  7.27
ATOM    737  CA  SER 103     -31.567  19.475  34.435  1.00  4.96
ATOM    738  C   SER 103     -30.259  19.365  35.228  1.00  6.42
ATOM    739  O   SER 103     -30.059  20.177  36.162  1.00  6.49
ATOM    740  CB  SER 103     -31.571  20.781  33.624  1.00  5.59
ATOM    741  OG  SER 103     -30.581  20.673  32.575  1.00  7.71
ATOM    742  N   GLY 104     -29.359  18.411  34.965  1.00  7.52
ATOM    743  CA  GLY 104     -28.071  18.282  35.661  1.00  5.92
ATOM    744  C   GLY 104     -27.031  17.745  34.686  1.00  6.41
ATOM    745  O   GLY 104     -27.354  17.083  33.665  1.00  7.09
ATOM    746  N   SER 105     -25.757  18.002  34.912  1.00  7.88
ATOM    747  OG  SER 105     -22.953  18.433  35.504  1.00 11.75
ATOM    748  CB  SER 105     -23.430  18.504  34.179  1.00  7.00
ATOM    749  CA  SER 105     -24.638  17.559  34.049  1.00 10.37
ATOM    750  C   SER 105     -24.255  16.085  34.102  1.00 10.06
ATOM    751  O   SER 105     -23.505  15.679  33.176  1.00 10.75
ATOM    752  N   THR 106     -24.719  15.248  35.018  1.00  9.74
ATOM    753  CA  THR 106     -24.403  13.811  35.029  1.00  9.92
ATOM    754  C   THR 106     -25.458  13.046  34.238  1.00  8.56
ATOM    755  O   THR 106     -25.079  12.174  33.464  1.00 10.42
ATOM    756  CB  THR 106     -24.322  13.103  36.435  1.00 10.71
ATOM    757  OG1 THR 106     -23.436  13.978  37.167  1.00 10.45
ATOM    758  CG2 THR 106     -23.782  11.671  36.508  1.00  6.76
ATOM    759  N   THR 107     -26.723  13.319  34.467  1.00  7.87
ATOM    760  CA  THR 107     -27.804  12.599  33.831  1.00  5.96
ATOM    761  C   THR 107     -28.634  13.349  32.838  1.00  7.88
ATOM    762  O   THR 107     -29.531  12.664  32.266  1.00  8.47
ATOM    763  CB  THR 107     -28.695  11.935  34.969  1.00  8.85
ATOM    764  OG1 THR 107     -29.241  13.086  35.695  1.00  7.24
ATOM    765  CG2 THR 107     -27.869  11.012  35.858  1.00  8.14
ATOM    766  N   GLY 108     -28.523  14.609  32.643  1.00  7.16
ATOM    767  CA  GLY 108     -29.341  15.323  31.611  1.00  8.94
ATOM    768  C   GLY 108     -30.668  15.756  32.223  1.00 10.50
ATOM    769  O   GLY 108     -30.722  16.175  33.436  1.00  8.98
ATOM    770  N   TRP 109     -31.691  15.642  31.408  1.00  6.52
ATOM    771  CD2 TRP 109     -35.413  18.684  30.968  1.00  5.39
```

```
ATOM    772  CE3 TRP   109     -34.790  19.728  31.656  1.00   5.67
ATOM    773  CZ3 TRP   109     -35.588  20.864  31.900  1.00  10.11
ATOM    774  CH2 TRP   109     -36.931  20.950  31.533  1.00   7.46
ATOM    775  CZ2 TRP   109     -37.555  19.912  30.864  1.00   5.36
ATOM    776  CE2 TRP   109     -36.762  18.789  30.603  1.00   8.40
ATOM    777  NE1 TRP   109     -37.097  17.619  29.964  1.00  11.33
ATOM    778  CD1 TRP   109     -35.996  16.771  29.909  1.00   8.89
ATOM    779  CG  TRP   109     -34.928  17.409  30.506  1.00   7.87
ATOM    780  CB  TRP   109     -33.558  16.856  30.594  1.00   4.08
ATOM    781  CA  TRP   109     -33.070  16.106  31.803  1.00   6.13
ATOM    782  C   TRP   109     -34.031  15.013  32.176  1.00   7.55
ATOM    783  O   TRP   109     -34.244  14.017  31.372  1.00   8.28
ATOM    784  N   HIS   110     -34.566  15.040  33.380  1.00   6.29
ATOM    785  CD2 HIS   110     -32.409  12.573  33.819  1.00   8.99
ATOM    786  NE2 HIS   110     -31.845  11.558  33.121  1.00  10.03
ATOM    787  CE1 HIS   110     -32.751  10.595  32.981  1.00  12.94
ATOM    788  ND1 HIS   110     -33.856  11.027  33.562  1.00  12.68
ATOM    789  CG  HIS   110     -33.678  12.246  34.128  1.00   9.92
ATOM    790  CB  HIS   110     -34.761  13.004  34.840  1.00   8.94
ATOM    791  CA  HIS   110     -35.487  13.971  33.861  1.00   7.82
ATOM    792  C   HIS   110     -36.648  14.637  34.584  1.00   7.74
ATOM    793  O   HIS   110     -36.444  15.708  35.190  1.00   8.03
ATOM    794  N   CYS   111     -37.832  13.990  34.506  1.00   7.77
ATOM    795  CA  CYS   111     -39.052  14.589  35.065  1.00   7.64
ATOM    796  C   CYS   111     -39.864  13.660  35.952  1.00   9.31
ATOM    797  O   CYS   111     -39.559  12.451  35.928  1.00  11.03
ATOM    798  CB  CYS   111     -39.988  15.100  33.925  1.00   9.61
ATOM    799  SG  CYS   111     -39.150  16.153  32.711  1.00   9.12
ATOM    800  N   GLY   112     -40.828  14.245  36.638  1.00   8.81
ATOM    801  CA  GLY   112     -41.625  13.408  37.597  1.00   8.51
ATOM    802  C   GLY   112     -42.521  14.315  38.399  1.00  10.25
ATOM    803  O   GLY   112     -42.794  15.437  37.941  1.00  12.04
ATOM    804  N   THR   113     -42.979  13.969  39.595  1.00  10.08
ATOM    805  CA  THR   113     -43.870  14.809  40.372  1.00   8.62
ATOM    806  C   THR   113     -43.359  15.387  41.685  1.00   9.71
ATOM    807  O   THR   113     -42.441  14.786  42.268  1.00  10.48
ATOM    808  CB  THR   113     -45.240  13.996  40.648  1.00  17.08
ATOM    809  OG1 THR   113     -44.930  12.755  41.340  1.00  19.10
ATOM    810  CG2 THR   113     -46.004  13.705  39.362  1.00  15.24
ATOM    811  N   ILE   114     -43.963  16.488  42.073  1.00   8.35
ATOM    812  CA  ILE   114     -43.662  17.108  43.365  1.00   9.73
ATOM    813  C   ILE   114     -44.554  16.338  44.383  1.00  13.59
ATOM    814  O   ILE   114     -45.816  16.336  44.198  1.00  12.54
ATOM    815  CB  ILE   114     -44.008  18.621  43.384  1.00  10.58
ATOM    816  CG1 ILE   114     -43.089  19.319  42.341  1.00  12.00
ATOM    817  CG2 ILE   114     -43.864  19.215  44.814  1.00  12.84
ATOM    818  CD1 ILE   114     -43.555  20.750  42.065  1.00  10.62
ATOM    819  N   GLN   115     -43.977  15.668  45.379  1.00  12.39
ATOM    820  NE2 GLN   115     -43.951  10.378  45.759  1.00  33.00
ATOM    821  OE1 GLN   115     -42.098  11.415  46.407  1.00  34.76
ATOM    822  CD  GLN   115     -43.243  11.496  45.943  1.00  30.30
ATOM    823  CG  GLN   115     -43.993  12.758  45.524  1.00  18.83
ATOM    824  CB  GLN   115     -44.077  13.606  46.811  1.00  11.43
ATOM    825  CA  GLN   115     -44.732  14.936  46.396  1.00  11.59
```

```
ATOM    826  C    GLN   115     -44.956   15.640   47.693   1.00  11.61
ATOM    827  O    GLN   115     -46.105   15.494   48.196   1.00  14.96
ATOM    828  N    ALA   116     -44.037   16.355   48.292   1.00  12.17
ATOM    829  CA   ALA   116     -44.291   16.976   49.618   1.00  10.65
ATOM    830  C    ALA   116     -43.263   18.055   49.863   1.00   9.88
ATOM    831  O    ALA   116     -42.162   17.978   49.326   1.00  13.41
ATOM    832  CB   ALA   116     -44.101   15.894   50.689   1.00  10.10
ATOM    833  N    ARG   117     -43.586   19.020   50.636   1.00   9.81
ATOM    834  NH2  ARG   117     -43.870   23.560   45.115   1.00  13.10
ATOM    835  NH1  ARG   117     -45.496   23.020   46.568   1.00  17.40
ATOM    836  CZ   ARG   117     -44.191   23.340   46.386   1.00  16.37
ATOM    837  NE   ARG   117     -43.268   23.465   47.330   1.00  14.91
ATOM    838  CD   ARG   117     -43.450   23.251   48.783   1.00  13.89
ATOM    839  CG   ARG   117     -43.323   21.801   49.092   1.00  10.78
ATOM    840  CB   ARG   117     -43.392   21.470   50.596   1.00  10.30
ATOM    841  CA   ARG   117     -42.725   20.137   50.983   1.00  10.62
ATOM    842  C    ARG   117     -42.465   20.023   52.496   1.00  12.42
ATOM    843  O    ARG   117     -43.122   19.229   53.201   1.00  14.36
ATOM    844  N    GLY   118     -41.566   20.803   52.999   1.00  10.94
ATOM    845  CA   GLY   118     -41.246   20.891   54.430   1.00  14.46
ATOM    846  C    GLY   118     -40.590   19.675   55.005   1.00  13.77
ATOM    847  O    GLY   118     -40.761   19.531   56.229   1.00  14.95
ATOM    848  N    GLN   119     -39.874   18.886   54.215   1.00  11.83
ATOM    849  NE2  GLN   119     -42.518   16.522   54.159   1.00  27.14
ATOM    850  OE1  GLN   119     -41.331   14.597   53.939   1.00  29.04
ATOM    851  CD   GLN   119     -41.505   15.779   53.683   1.00  26.05
ATOM    852  CG   GLN   119     -40.511   16.511   52.791   1.00  23.83
ATOM    853  CB   GLN   119     -39.161   16.633   53.499   1.00  15.28
ATOM    854  CA   GLN   119     -39.228   17.649   54.654   1.00  12.25
ATOM    855  C    GLN   119     -37.819   17.866   55.191   1.00  13.13
ATOM    856  O    GLN   119     -37.023   18.655   54.674   1.00  11.96
ATOM    857  N    SER   120     -37.520   17.136   56.272   1.00  12.77
ATOM    858  OG   SER   120     -36.874   16.674   59.024   0.50  13.43
ATOM    859  CB   SER   120     -36.074   17.591   58.330   0.50  15.06
ATOM    862  CA   SER   120     -36.147   17.234   56.873   1.00  11.79
ATOM    863  C    SER   120     -35.513   15.938   56.438   1.00  14.19
ATOM    864  O    SER   120     -36.167   14.855   56.352   1.00  14.17
ATOM    865  N    VAL   121     -34.228   16.035   56.037   1.00  14.53
ATOM    866  CG2  VAL   121     -34.392   15.445   53.235   1.00  20.02
ATOM    867  CG1  VAL   121     -32.537   13.814   53.494   1.00  22.53
ATOM    868  CB   VAL   121     -33.176   15.085   54.041   1.00  19.23
ATOM    869  CA   VAL   121     -33.466   14.920   55.565   1.00  14.60
ATOM    870  C    VAL   121     -32.106   14.892   56.248   1.00  17.85
ATOM    871  O    VAL   121     -31.399   15.890   56.335   1.00  16.78
ATOM    872  N    SER   122     -31.749   13.694   56.677   1.00  18.77
ATOM    873  OG   SER   122     -31.320   13.436   59.447   1.00  35.50
ATOM    874  CB   SER   122     -30.306   12.902   58.611   1.00  26.24
ATOM    875  CA   SER   122     -30.397   13.594   57.262   1.00  20.95
ATOM    876  C    SER   122     -29.504   12.911   56.238   1.00  20.78
ATOM    877  O    SER   122     -29.704   11.746   55.840   1.00  25.20
ATOM    878  N    TYR   123     -28.548   13.651   55.794   1.00  19.04
ATOM    879  CA   TYR   123     -27.479   13.164   54.927   1.00  21.72
ATOM    880  C    TYR   123     -26.478   12.615   55.995   1.00  25.29
ATOM    881  O    TYR   123     -26.521   13.015   57.187   1.00  26.53
```

```
ATOM    882  CB  TYR   123     -26.981  14.342  54.135  1.00 18.93
ATOM    883  CG  TYR   123     -27.915  14.920  53.100  1.00 18.61
ATOM    884  CD1 TYR   123     -27.849  16.273  52.784  1.00 15.70
ATOM    885  CD2 TYR   123     -28.840  14.144  52.381  1.00 21.00
ATOM    886  CE1 TYR   123     -28.658  16.844  51.808  1.00 15.37
ATOM    887  CE2 TYR   123     -29.712  14.700  51.423  1.00 18.34
ATOM    888  CZ  TYR   123     -29.581  16.067  51.133  1.00 16.62
ATOM    889  OH  TYR   123     -30.390  16.593  50.172  1.00 15.25
ATOM    890  N   PRO   124     -25.578  11.721  55.647  1.00 28.48
ATOM    891  CG  PRO   124     -24.105  10.334  54.354  1.00 32.40
ATOM    892  CD  PRO   124     -25.391  11.155  54.297  1.00 30.53
ATOM    893  CB  PRO   124     -23.748  10.168  55.828  1.00 32.32
ATOM    894  CA  PRO   124     -24.583  11.183  56.598  1.00 31.44
ATOM    895  C   PRO   124     -23.732  12.285  57.226  1.00 32.68
ATOM    896  O   PRO   124     -23.355  12.124  58.408  1.00 33.64
ATOM    897  N   GLU   125     -23.417  13.329  56.485  1.00 32.09
ATOM    898  CA  GLU   125     -22.646  14.515  56.843  1.00 32.45
ATOM    899  C   GLU   125     -23.410  15.484  57.766  1.00 33.22
ATOM    900  O   GLU   125     -22.932  15.954  58.861  1.00 33.87
ATOM    901  CB  GLU   125     -22.144  15.220  55.588  1.00 28.10
ATOM    902  CG  GLU   125     -22.899  15.278  54.299  1.00 34.56
ATOM    903  CD  GLU   125     -23.341  14.605  53.384  0.00 53.35
ATOM    904  OE1 GLU   125     -23.517  15.100  52.231  0.00 59.96
ATOM    905  OE2 GLU   125     -23.156  13.352  53.591  0.00 58.46
ATOM    906  N   GLY   126     -24.666  15.793  57.397  1.00 31.75
ATOM    907  CA  GLY   126     -25.549  16.682  58.182  1.00 28.35
ATOM    908  C   GLY   126     -27.017  16.695  57.720  1.00 25.07
ATOM    909  O   GLY   126     -27.393  16.107  56.682  1.00 25.93
ATOM    910  N   THR   127     -27.811  17.417  58.486  1.00 19.30
ATOM    911  CG2 THR   127     -31.485  17.638  59.616  1.00 15.49
ATOM    912  OG1 THR   127     -29.548  16.190  60.199  1.00 22.50
ATOM    913  CB  THR   127     -29.964  17.487  59.664  1.00 14.93
ATOM    914  CA  THR   127     -29.242  17.558  58.256  1.00 13.91
ATOM    915  C   THR   127     -29.689  18.791  57.491  1.00 11.25
ATOM    916  O   THR   127     -29.203  19.885  57.803  1.00 10.59
ATOM    917  N   VAL   128     -30.649  18.626  56.584  1.00 11.18
ATOM    918  CA  VAL   128     -31.201  19.747  55.791  1.00  9.77
ATOM    919  C   VAL   128     -32.688  19.787  56.164  1.00  8.45
ATOM    920  O   VAL   128     -33.182  18.697  56.393  1.00 11.45
ATOM    921  CB  VAL   128     -30.956  19.633  54.298  1.00  7.25
ATOM    922  CG1 VAL   128     -29.466  19.790  54.013  1.00 11.55
ATOM    923  CG2 VAL   128     -31.377  18.285  53.735  1.00  9.36
ATOM    924  N   THR   129     -33.266  20.960  56.248  1.00  9.49
ATOM    925  CG2 THR   129     -34.182  21.202  59.125  1.00 18.71
ATOM    926  OG1 THR   129     -34.282  23.173  57.758  1.00 14.40
ATOM    927  CB  THR   129     -34.884  21.913  57.959  1.00  8.96
ATOM    928  CA  THR   129     -34.680  21.088  56.613  1.00  9.66
ATOM    929  C   THR   129     -35.407  21.804  55.487  1.00 10.11
ATOM    930  O   THR   129     -34.796  22.467  54.615  1.00 10.92
ATOM    931  N   ASN   130     -36.709  21.619  55.563  1.00 10.84
ATOM    932  ND2 ASN   130     -38.570  25.717  53.765  1.00 35.10
ATOM    933  OD1 ASN   130     -39.854  23.969  54.369  1.00 28.19
ATOM    934  CG  ASN   130     -38.739  24.527  54.362  1.00 30.11
ATOM    935  CB  ASN   130     -37.496  23.827  54.952  1.00 17.09
```

```
ATOM    936  CA  ASN   130     -37.620  22.299  54.616  1.00 12.34
ATOM    937  C   ASN   130     -37.388  21.988  53.136  1.00 11.59
ATOM    938  O   ASN   130     -37.557  22.883  52.268  1.00 11.46
ATOM    939  N   MET   131     -37.056  20.742  52.880  1.00  9.76
ATOM    940  CE  MET   131     -33.020  20.248  50.187  1.00 16.57
ATOM    941  SD  MET   131     -33.597  21.082  51.629  1.00 20.94
ATOM    942  CG  MET   131     -34.411  19.573  52.379  1.00  9.59
ATOM    943  CB  MET   131     -35.664  19.199  51.580  1.00  5.73
ATOM    944  CA  MET   131     -36.732  20.297  51.529  1.00  9.93
ATOM    945  C   MET   131     -38.007  19.797  50.840  1.00  9.00
ATOM    946  O   MET   131     -38.962  19.372  51.519  1.00 10.48
ATOM    947  N   THR   132     -37.995  19.869  49.527  1.00  8.82
ATOM    948  CA  THR   132     -39.129  19.393  48.710  1.00  5.72
ATOM    949  C   THR   132     -38.769  18.054  48.108  1.00  7.44
ATOM    950  O   THR   132     -37.719  17.850  47.428  1.00  9.83
ATOM    951  CB  THR   132     -39.497  20.516  47.675  1.00  6.44
ATOM    952  OG1 THR   132     -39.851  21.700  48.434  1.00  9.35
ATOM    953  CG2 THR   132     -40.681  20.100  46.737  1.00  7.59
ATOM    954  N   ARG   133     -39.640  17.061  48.306  1.00  4.85
ATOM    955  NH2 ARG   133     -42.116  12.875  51.526  1.00 39.69
ATOM    956  NH1 ARG   133     -43.846  11.985  50.304  1.00 32.03
ATOM    957  CZ  ARG   133     -42.539  12.272  50.397  1.00 36.90
ATOM    958  NE  ARG   133     -41.666  11.948  49.418  1.00 28.98
ATOM    959  CD  ARG   133     -40.253  12.204  49.398  1.00 20.06
ATOM    960  CG  ARG   133     -39.832  13.218  48.354  1.00 11.77
ATOM    961  CB  ARG   133     -40.079  14.660  48.801  1.00  6.59
ATOM    962  CA  ARG   133     -39.443  15.674  47.833  1.00  6.76
ATOM    963  C   ARG   133     -40.092  15.457  46.455  1.00  7.46
ATOM    964  O   ARG   133     -41.227  15.963  46.241  1.00  9.38
ATOM    965  N   THR   134     -39.360  14.793  45.552  1.00  9.68
ATOM    966  CG2 THR   134     -39.353  17.060  43.521  1.00  7.44
ATOM    967  OG1 THR   134     -38.110  15.030  42.788  1.00  8.17
ATOM    968  CB  THR   134     -39.392  15.603  43.141  1.00  8.74
ATOM    969  CA  THR   134     -39.921  14.565  44.202  1.00  8.24
ATOM    970  C   THR   134     -39.576  13.135  43.785  1.00  8.06
ATOM    971  O   THR   134     -38.694  12.518  44.396  1.00  9.92
ATOM    972  N   THR   135     -40.301  12.622  42.770  1.00  7.24
ATOM    973  CG2 THR   135     -42.463  10.541  42.733  1.00 12.10
ATOM    974  OG1 THR   135     -41.763  11.403  40.497  1.00 11.13
ATOM    975  CB  THR   135     -41.362  10.601  41.650  1.00 10.58
ATOM    976  CA  THR   135     -40.037  11.294  42.228  1.00  8.03
ATOM    977  C   THR   135     -38.974  11.340  41.147  1.00  7.98
ATOM    978  O   THR   135     -38.731  10.327  40.471  1.00  9.10
ATOM    979  N   VAL   136     -38.326  12.452  40.852  1.00 10.38
ATOM    980  CG2 VAL   136     -38.483  14.754  39.130  1.00  6.65
ATOM    981  CG1 VAL   136     -36.094  14.300  38.374  1.00 10.08
ATOM    982  CB  VAL   136     -37.136  14.096  39.495  1.00  9.89
ATOM    983  CA  VAL   136     -37.296  12.595  39.813  1.00  9.10
ATOM    984  C   VAL   136     -35.990  11.927  40.235  1.00  9.23
ATOM    985  O   VAL   136     -35.640  12.113  41.414  1.00 11.00
ATOM    986  N   CYS   137     -35.273  11.188  39.408  1.00  7.90
ATOM    987  CA  CYS   137     -33.997  10.564  39.780  1.00  8.61
ATOM    988  C   CYS   137     -32.841  11.600  39.681  1.00  9.07
ATOM    989  O   CYS   137     -33.024  12.659  39.015  1.00  9.87
```

```
ATOM    990  CB  CYS  137     -33.702   9.452  38.761  1.00   8.35
ATOM    991  SG  CYS  137     -33.425  10.011  37.031  1.00  11.68
ATOM    992  N   ALA  138     -31.687  11.330  40.300  1.00   7.09
ATOM    993  CB  ALA  138     -30.467  13.454  41.104  1.00   8.40
ATOM    994  CA  ALA  138     -30.503  12.207  40.220  1.00   8.25
ATOM    995  C   ALA  138     -29.294  11.352  40.568  1.00   8.58
ATOM    996  O   ALA  138     -29.409  10.287  41.211  1.00  10.28
ATOM    997  N   GLU  139     -28.105  11.803  40.178  1.00   9.17
ATOM    998  OE2 GLU  139     -27.880   7.597  37.175  1.00  10.81
ATOM    999  OE1 GLU  139     -25.864   8.348  37.135  1.00  10.87
ATOM   1000  CD  GLU  139     -26.946   8.270  37.673  1.00  12.62
ATOM   1001  CG  GLU  139     -27.289   9.053  38.912  1.00  10.79
ATOM   1002  CB  GLU  139     -26.414  10.298  39.196  1.00   8.09
ATOM   1003  CA  GLU  139     -26.818  11.099  40.431  1.00   9.02
ATOM   1004  C   GLU  139     -25.776  12.156  40.775  1.00   9.85
ATOM   1005  O   GLU  139     -25.966  13.362  40.507  1.00   9.59
ATOM   1006  N   PRO  140     -24.677  11.769  41.394  1.00  11.00
ATOM   1007  CG  PRO  140     -23.255  10.606  42.890  1.00  10.81
ATOM   1008  CD  PRO  140     -24.305  10.376  41.788  1.00  10.23
ATOM   1009  CB  PRO  140     -22.595  11.921  42.569  1.00  13.07
ATOM   1010  CA  PRO  140     -23.611  12.741  41.794  1.00  10.28
ATOM   1011  C   PRO  140     -23.095  13.561  40.611  1.00   9.93
ATOM   1012  O   PRO  140     -22.846  13.081  39.498  1.00  11.30
ATOM   1013  N   GLY  141     -23.015  14.865  40.884  1.00   7.17
ATOM   1014  CA  GLY  141     -22.596  15.857  39.927  1.00   7.59
ATOM   1015  C   GLY  141     -23.845  16.611  39.448  1.00   6.72
ATOM   1016  O   GLY  141     -23.742  17.715  38.907  1.00   7.49
ATOM   1017  N   ASP  142     -25.050  16.077  39.671  1.00   7.35
ATOM   1018  CA  ASP  142     -26.325  16.710  39.296  1.00   6.21
ATOM   1019  C   ASP  142     -26.663  17.752  40.369  1.00   5.40
ATOM   1020  O   ASP  142     -27.522  18.627  40.062  1.00   3.95
ATOM   1021  CB  ASP  142     -27.497  15.784  39.058  1.00   7.83
ATOM   1022  CG  ASP  142     -27.531  14.867  37.860  1.00   7.53
ATOM   1023  OD1 ASP  142     -28.075  13.736  37.908  1.00   7.92
ATOM   1024  OD2 ASP  142     -27.048  15.355  36.863  1.00   6.85
ATOM   1025  N   SER  143     -26.112  17.668  41.546  1.00   5.60
ATOM   1026  CA  SER  143     -26.422  18.670  42.589  1.00   5.95
ATOM   1027  C   SER  143     -26.287  20.098  42.102  1.00   7.22
ATOM   1028  O   SER  143     -25.328  20.407  41.346  1.00   7.03
ATOM   1029  CB  SER  143     -25.451  18.527  43.777  1.00   7.47
ATOM   1030  OG  SER  143     -25.764  17.255  44.327  1.00  11.26
ATOM   1031  N   GLY  144     -27.206  20.956  42.571  1.00   5.35
ATOM   1032  CA  GLY  144     -27.301  22.370  42.249  1.00   5.48
ATOM   1033  C   GLY  144     -28.051  22.665  40.945  1.00   6.00
ATOM   1034  O   GLY  144     -28.334  23.858  40.698  1.00   7.24
ATOM   1035  N   GLY  145     -28.295  21.671  40.140  1.00   5.00
ATOM   1036  CA  GLY  145     -28.959  21.818  38.828  1.00   5.08
ATOM   1037  C   GLY  145     -30.400  22.272  38.981  1.00   6.80
ATOM   1038  O   GLY  145     -31.096  22.093  40.013  1.00   8.09
ATOM   1039  N   SER  146     -31.016  22.823  37.953  1.00   4.98
ATOM   1040  CA  SER  146     -32.375  23.344  37.961  1.00   4.54
ATOM   1041  C   SER  146     -33.561  22.389  38.160  1.00   5.95
ATOM   1042  O   SER  146     -33.513  21.305  37.566  1.00   6.69
ATOM   1043  CB  SER  146     -32.609  23.870  36.500  1.00   4.69
```

```
ATOM   1044  OG   SER  146   -31.487  24.440  35.945  1.00   7.80
ATOM   1045  N    TYR  147   -34.584  22.813  38.888  1.00   4.96
ATOM   1046  OH   TYR  147   -34.686  16.409  41.718  1.00  15.17
ATOM   1047  CD2  TYR  147   -36.809  19.212  40.614  1.00   8.25
ATOM   1048  CE2  TYR  147   -36.419  17.910  40.955  1.00  10.83
ATOM   1049  CZ   TYR  147   -35.130  17.695  41.413  1.00  13.00
ATOM   1050  CE1  TYR  147   -34.196  18.722  41.524  1.00   8.41
ATOM   1051  CD1  TYR  147   -34.601  20.028  41.200  1.00   7.28
ATOM   1052  CG   TYR  147   -35.885  20.262  40.762  1.00   6.98
ATOM   1053  CB   TYR  147   -36.258  21.677  40.422  1.00   5.48
ATOM   1054  CA   TYR  147   -35.875  22.091  39.028  1.00   5.55
ATOM   1055  C    TYR  147   -36.829  23.167  38.409  1.00   6.41
ATOM   1056  O    TYR  147   -36.859  24.306  38.918  1.00   6.54
ATOM   1057  N    ILE  148   -37.559  22.845  37.365  1.00   5.67
ATOM   1058  CA   ILE  148   -38.454  23.821  36.710  1.00   6.64
ATOM   1059  C    ILE  148   -39.776  23.154  36.317  1.00   6.20
ATOM   1060  O    ILE  148   -39.743  21.993  35.834  1.00   6.60
ATOM   1061  CB   ILE  148   -37.661  24.408  35.475  1.00   8.25
ATOM   1062  CG1  ILE  148   -38.445  25.567  34.843  1.00  10.19
ATOM   1063  CG2  ILE  148   -37.269  23.309  34.443  1.00  11.02
ATOM   1064  CD1  ILE  148   -37.739  26.438  33.738  1.00  11.12
ATOM   1065  N    SER  149   -40.878  23.912  36.472  1.00   6.67
ATOM   1066  OG   SER  149   -42.874  22.350  38.136  1.00  15.36
ATOM   1067  CB   SER  149   -43.209  23.415  37.231  1.00   9.17
ATOM   1068  CA   SER  149   -42.219  23.396  36.098  1.00   7.08
ATOM   1069  C    SER  149   -42.712  24.364  35.000  1.00   7.85
ATOM   1070  O    SER  149   -43.087  25.496  35.341  1.00   8.98
ATOM   1071  N    GLY  150   -42.632  23.897  33.754  1.00  10.00
ATOM   1072  CA   GLY  150   -43.066  24.798  32.663  1.00  11.86
ATOM   1073  C    GLY  150   -41.990  25.883  32.482  1.00   8.97
ATOM   1074  O    GLY  150   -40.850  25.591  32.148  1.00  12.79
ATOM   1075  N    THR  151   -42.463  27.096  32.745  1.00   9.09
ATOM   1076  CG2  THR  151   -42.428  29.087  30.347  1.00  13.40
ATOM   1077  OG1  THR  151   -43.398  29.844  32.497  1.00  13.13
ATOM   1078  CB   THR  151   -42.170  29.426  31.816  1.00  11.88
ATOM   1079  CA   THR  151   -41.527  28.257  32.661  1.00  10.61
ATOM   1080  C    THR  151   -41.196  28.758  34.085  1.00   9.76
ATOM   1081  O    THR  151   -40.553  29.810  34.179  1.00  10.13
ATOM   1082  N    GLN  152   -41.628  28.099  35.157  1.00   6.87
ATOM   1083  CA   GLN  152   -41.440  28.600  36.494  1.00   7.20
ATOM   1084  C    GLN  152   -40.304  27.909  37.266  1.00   8.56
ATOM   1085  O    GLN  152   -40.488  26.681  37.461  1.00  12.38
ATOM   1086  CB   GLN  152   -42.770  28.493  37.286  1.00   6.03
ATOM   1087  CG   GLN  152   -43.935  29.238  36.607  1.00   9.11
ATOM   1088  CD   GLN  152   -43.668  30.705  36.459  1.00   7.44
ATOM   1089  OE1  GLN  152   -43.411  31.422  37.422  1.00  11.18
ATOM   1090  NE2  GLN  152   -43.686  31.229  35.247  1.00  15.32
ATOM   1091  N    ALA  153   -39.288  28.691  37.696  1.00   7.16
ATOM   1092  CA   ALA  153   -38.166  28.065  38.442  1.00   6.99
ATOM   1093  C    ALA  153   -38.696  27.572  39.786  1.00   6.78
ATOM   1094  O    ALA  153   -39.432  28.329  40.450  1.00   8.03
ATOM   1095  CB   ALA  153   -37.062  29.133  38.567  1.00   6.81
ATOM   1096  N    GLN  154   -38.383  26.349  40.198  1.00   4.41
ATOM   1097  CA   GLN  154   -38.827  25.782  41.460  1.00   6.90
```

```
ATOM   1098  C    GLN  154     -37.692   25.687   42.494  1.00   7.22
ATOM   1099  O    GLN  154     -37.931   26.098   43.640  1.00   7.22
ATOM   1100  CB   GLN  154     -39.459   24.374   41.221  1.00   6.12
ATOM   1101  CG   GLN  154     -40.644   24.402   40.211  1.00   6.24
ATOM   1102  CD   GLN  154     -41.732   25.321   40.671  1.00   9.04
ATOM   1103  OE1  GLN  154     -42.271   25.234   41.795  1.00   9.56
ATOM   1104  NE2  GLN  154     -42.164   26.267   39.859  1.00   4.50
ATOM   1105  N    GLY  155     -36.547   25.153   42.078  1.00   7.56
ATOM   1106  CA   GLY  155     -35.475   24.954   43.098  1.00   7.31
ATOM   1107  C    GLY  155     -34.202   24.370   42.501  1.00   7.69
ATOM   1108  O    GLY  155     -34.029   24.335   41.280  1.00   7.17
ATOM   1109  N    VAL  156     -33.252   24.073   43.370  1.00   6.91
ATOM   1110  CA   VAL  156     -31.925   23.515   42.968  1.00   7.24
ATOM   1111  C    VAL  156     -31.760   22.136   43.631  1.00   5.91
ATOM   1112  O    VAL  156     -32.096   21.942   44.815  1.00   6.78
ATOM   1113  CB   VAL  156     -30.786   24.527   43.154  1.00   6.19
ATOM   1114  CG1  VAL  156     -31.048   25.862   42.407  1.00   5.61
ATOM   1115  CG2  VAL  156     -30.409   24.754   44.616  1.00   8.17
ATOM   1116  N    THR  157     -31.186   21.164   42.911  1.00   3.82
ATOM   1117  CG2  THR  157     -30.184   17.395   42.515  1.00   4.16
ATOM   1118  OG1  THR  157     -30.991   19.138   41.073  1.00   8.01
ATOM   1119  CB   THR  157     -30.243   18.893   42.293  1.00   3.37
ATOM   1120  CA   THR  157     -30.971   19.799   43.383  1.00   4.97
ATOM   1121  C    THR  157     -30.083   19.754   44.627  1.00   5.89
ATOM   1122  O    THR  157     -28.979   20.281   44.589  1.00   5.74
ATOM   1123  N    SER  158     -30.588   19.070   45.635  1.00   5.99
ATOM   1124  CA   SER  158     -29.830   18.914   46.876  1.00   7.64
ATOM   1125  C    SER  158     -29.316   17.473   46.969  1.00  10.26
ATOM   1126  O    SER  158     -28.087   17.229   47.132  1.00  10.04
ATOM   1127  CB   SER  158     -30.619   19.304   48.134  1.00   8.30
ATOM   1128  OG   SER  158     -29.853   18.975   49.296  1.00   9.39
ATOM   1129  N    GLY  159     -30.150   16.443   46.900  1.00   9.83
ATOM   1130  CA   GLY  159     -29.635   15.060   47.040  1.00   9.90
ATOM   1131  C    GLY  159     -30.756   14.048   47.006  1.00  12.82
ATOM   1132  O    GLY  159     -31.878   14.478   46.680  1.00  13.31
ATOM   1133  N    GLY  160     -30.510   12.792   47.352  1.00  12.00
ATOM   1134  CA   GLY  160     -31.646   11.846   47.257  1.00  12.56
ATOM   1135  C    GLY  160     -31.091   10.410   47.219  1.00  15.35
ATOM   1136  O    GLY  160     -29.988   10.197   47.741  1.00  15.70
ATOM   1137  N    SER  161     -31.869    9.497   46.679  1.00  13.10
ATOM   1138  OG   SER  161     -33.410    7.381   47.752  1.00  18.73
ATOM   1139  CB   SER  161     -31.996    7.324   47.833  1.00  16.84
ATOM   1140  CA   SER  161     -31.379    8.089   46.671  1.00  14.66
ATOM   1141  C    SER  161     -31.670    7.448   45.325  1.00  13.50
ATOM   1142  O    SER  161     -32.491    8.066   44.640  1.00  13.10
ATOM   1143  N    GLY  162     -31.078    6.310   45.040  1.00  11.84
ATOM   1144  CA   GLY  162     -31.318    5.641   43.734  1.00  12.53
ATOM   1145  C    GLY  162     -30.457    6.331   42.672  1.00  12.12
ATOM   1146  O    GLY  162     -29.545    7.088   42.957  1.00  11.79
ATOM   1147  N    ASN  163     -30.786    6.068   41.407  1.00  10.66
ATOM   1148  CA   ASN  163     -30.058    6.588   40.269  1.00   8.29
ATOM   1149  C    ASN  163     -31.033    6.671   39.088  1.00  11.02
ATOM   1150  O    ASN  163     -32.220    6.293   39.233  1.00  10.33
ATOM   1151  CB   ASN  163     -28.827    5.741   39.950  1.00  10.88
```

```
ATOM   1152  CG   ASN   163     -29.238    4.312   39.578  1.00  14.23
ATOM   1153  OD1  ASN   163     -29.966    3.979   38.660  1.00  11.31
ATOM   1154  ND2  ASN   163     -28.649    3.362   40.334  1.00  18.48
ATOM   1155  N    CYS   164     -30.499    7.132   37.956  1.00  10.86
ATOM   1156  CA   CYS   164     -31.420    7.271   36.806  1.00  11.83
ATOM   1157  C    CYS   164     -31.687    6.006   35.998  1.00  13.69
ATOM   1158  O    CYS   164     -32.428    6.145   34.993  1.00  15.15
ATOM   1159  CB   CYS   164     -31.100    8.500   35.971  1.00  10.31
ATOM   1160  SG   CYS   164     -31.448   10.097   36.795  1.00   9.57
ATOM   1161  N    ARG   165     -31.110    4.919   36.364  1.00  11.68
ATOM   1162  NH2  ARG   165     -26.089    2.173   38.339  1.00  59.15
ATOM   1163  NH1  ARG   165     -25.617    4.096   37.196  1.00  58.35
ATOM   1164  CZ   ARG   165     -26.258    2.909   37.212  1.00  55.39
ATOM   1165  NE   ARG   165     -27.054    2.356   36.310  1.00  47.93
ATOM   1166  CD   ARG   165     -27.631    2.632   35.037  1.00  40.44
ATOM   1167  CG   ARG   165     -28.933    3.381   34.944  1.00  31.56
ATOM   1168  CB   ARG   165     -30.065    2.765   35.785  1.00  18.33
ATOM   1169  CA   ARG   165     -31.324    3.621   35.703  1.00  17.34
ATOM   1170  C    ARG   165     -32.498    2.928   36.433  1.00  14.57
ATOM   1171  O    ARG   165     -33.499    2.588   35.782  1.00  15.39
ATOM   1172  N    THR   166     -32.347    2.784   37.751  1.00  12.62
ATOM   1173  CG2  THR   166     -31.557    0.620   39.350  1.00  18.19
ATOM   1174  OG1  THR   166     -32.296    2.562   40.679  1.00  17.67
ATOM   1175  CB   THR   166     -32.716    1.474   39.795  1.00  16.75
ATOM   1176  CA   THR   166     -33.407    2.140   38.540  1.00  13.18
ATOM   1177  C    THR   166     -34.528    3.049   39.012  1.00  15.18
ATOM   1178  O    THR   166     -35.581    2.528   39.436  1.00  16.50
ATOM   1179  N    GLY   167     -34.296    4.347   39.040  1.00  13.17
ATOM   1180  CA   GLY   167     -35.255    5.345   39.536  1.00  13.42
ATOM   1181  C    GLY   167     -34.815    5.663   40.997  1.00  14.50
ATOM   1182  O    GLY   167     -33.957    4.993   41.596  1.00  13.35
ATOM   1183  N    GLY   168     -35.330    6.773   41.562  1.00  14.99
ATOM   1184  CA   GLY   168     -34.923    7.118   42.940  1.00  12.40
ATOM   1185  C    GLY   168     -35.852    8.241   43.371  1.00  15.29
ATOM   1186  O    GLY   168     -36.909    8.509   42.754  1.00  14.71
ATOM   1187  N    THR   169     -35.422    8.845   44.471  1.00  14.65
ATOM   1188  CG2  THR   169     -37.341   10.701   47.345  1.00  11.85
ATOM   1189  OG1  THR   169     -37.698    8.540   46.281  1.00  16.91
ATOM   1190  CB   THR   169     -36.711    9.582   46.529  1.00  14.83
ATOM   1191  CA   THR   169     -36.177    9.973   45.077  1.00  13.13
ATOM   1192  C    THR   169     -35.165   11.121   45.248  1.00  11.43
ATOM   1193  O    THR   169     -34.007   10.807   45.611  1.00  11.62
ATOM   1194  N    THR   170     -35.621   12.315   44.946  1.00   8.52
ATOM   1195  CG2  THR   170     -33.232   12.956   43.075  1.00   6.44
ATOM   1196  OG1  THR   170     -35.355   14.161   43.068  1.00  19.35
ATOM   1197  CB   THR   170     -34.090   13.942   43.798  1.00  12.63
ATOM   1198  CA   THR   170     -34.667   13.406   45.165  1.00   8.99
ATOM   1199  C    THR   170     -35.363   14.555   45.880  1.00  11.07
ATOM   1200  O    THR   170     -36.582   14.758   45.736  1.00  12.91
ATOM   1201  N    PHE   171     -34.531   15.291   46.609  1.00   9.07
ATOM   1202  CD2  PHE   171     -36.450   15.430   50.154  1.00  12.37
ATOM   1203  CE2  PHE   171     -37.017   14.281   50.750  1.00  12.72
ATOM   1204  CZ   PHE   171     -36.332   13.053   50.718  1.00  14.13
ATOM   1205  CE1  PHE   171     -35.064   12.901   50.136  1.00  11.85
```

```
ATOM   1206  CD1 PHE   171     -34.501  14.041  49.547  1.00 12.01
ATOM   1207  CG  PHE   171     -35.187  15.262  49.538  1.00 14.42
ATOM   1208  CB  PHE   171     -34.500  16.430  48.855  1.00  8.65
ATOM   1209  CA  PHE   171     -34.946  16.484  47.353  1.00 10.31
ATOM   1210  C   PHE   171     -34.276  17.746  46.736  1.00  9.69
ATOM   1211  O   PHE   171     -33.096  17.749  46.336  1.00 10.28
ATOM   1212  N   TYR   172     -35.022  18.818  46.721  1.00  6.76
ATOM   1213  OH  TYR   172     -40.405  22.042  43.789  1.00 10.33
ATOM   1214  CD2 TYR   172     -37.368  19.978  44.053  1.00  7.13
ATOM   1215  CE2 TYR   172     -38.680  20.393  43.754  1.00  9.56
ATOM   1216  CZ  TYR   172     -39.128  21.645  44.088  1.00 11.06
ATOM   1217  CE1 TYR   172     -38.255  22.544  44.740  1.00  7.89
ATOM   1218  CD1 TYR   172     -36.943  22.125  44.984  1.00  5.66
ATOM   1219  CG  TYR   172     -36.496  20.849  44.693  1.00  5.21
ATOM   1220  CB  TYR   172     -35.049  20.462  44.892  1.00  6.84
ATOM   1221  CA  TYR   172     -34.465  20.077  46.256  1.00  7.19
ATOM   1222  C   TYR   172     -34.711  21.217  47.245  1.00  6.71
ATOM   1223  O   TYR   172     -35.673  21.172  48.064  1.00  8.96
ATOM   1224  N   GLN   173     -33.781  22.185  47.157  1.00  5.53
ATOM   1225  NE2 GLN   173     -33.746  26.714  50.033  1.00  6.96
ATOM   1226  OE1 GLN   173     -32.289  25.169  50.891  1.00 10.23
ATOM   1227  CD  GLN   173     -32.795  25.753  49.933  1.00  9.42
ATOM   1228  CG  GLN   173     -32.411  25.493  48.482  1.00  3.75
ATOM   1229  CB  GLN   173     -32.463  24.037  48.054  1.00  8.35
ATOM   1230  CA  GLN   173     -33.883  23.428  47.962  1.00  5.17
ATOM   1231  C   GLN   173     -34.741  24.402  47.187  1.00  6.61
ATOM   1232  O   GLN   173     -34.469  24.693  45.967  1.00  7.86
ATOM   1233  N   GLU   174     -35.814  24.921  47.782  1.00  6.75
ATOM   1234  OE2 GLU   174     -40.122  25.837  46.396  1.00  8.25
ATOM   1235  OE1 GLU   174     -40.521  23.919  47.243  1.00 10.88
ATOM   1236  CD  GLU   174     -39.899  24.969  47.265  1.00 10.25
ATOM   1237  CG  GLU   174     -38.863  25.164  48.362  1.00  8.85
ATOM   1238  CB  GLU   174     -37.861  26.313  48.083  1.00  9.36
ATOM   1239  CA  GLU   174     -36.686  25.892  47.108  1.00  7.86
ATOM   1240  C   GLU   174     -35.933  27.178  46.774  1.00  8.69
ATOM   1241  O   GLU   174     -35.082  27.712  47.515  1.00  9.98
ATOM   1242  N   VAL   175     -36.198  27.769  45.591  1.00  8.61
ATOM   1243  CG2 VAL   175     -34.568  29.950  43.032  1.00 11.90
ATOM   1244  CG1 VAL   175     -36.989  29.512  42.968  1.00 13.78
ATOM   1245  CB  VAL   175     -35.652  29.062  43.589  1.00 13.52
ATOM   1246  CA  VAL   175     -35.605  29.022  45.144  1.00  8.03
ATOM   1247  C   VAL   175     -36.196  30.221  45.869  1.00  8.45
ATOM   1248  O   VAL   175     -35.453  31.199  46.161  1.00  8.96
ATOM   1249  N   THR   176     -37.454  30.220  46.297  1.00  9.06
ATOM   1250  CG2 THR   176     -40.371  32.282  47.869  1.00 18.26
ATOM   1251  OG1 THR   176     -40.343  30.692  46.091  1.00 18.82
ATOM   1252  CB  THR   176     -39.648  31.030  47.350  1.00 15.35
ATOM   1253  CA  THR   176     -38.133  31.355  46.965  1.00 10.08
ATOM   1254  C   THR   176     -37.370  32.053  48.082  1.00 12.75
ATOM   1255  O   THR   176     -37.203  33.295  48.105  1.00 12.78
ATOM   1256  N   PRO   177     -36.827  31.275  49.019  1.00 13.60
ATOM   1257  CA  PRO   177     -36.059  31.831  50.137  1.00 14.56
ATOM   1258  C   PRO   177     -34.832  32.550  49.634  1.00 14.53
ATOM   1259  O   PRO   177     -34.405  33.537  50.205  1.00 14.33
```

```
ATOM   1260  CB   PRO  177     -35.684  30.599  50.967  1.00  15.59
ATOM   1261  CG   PRO  177     -36.607  29.488  50.587  1.00  15.55
ATOM   1262  CD   PRO  177     -37.028  29.818  49.155  1.00  14.17
ATOM   1263  N    MET  178     -34.177  32.085  48.557  1.00  11.26
ATOM   1264  CE   MET  178     -31.755  28.533  46.007  1.00  19.72
ATOM   1265  SD   MET  178     -30.708  29.927  46.237  1.00  22.73
ATOM   1266  CG   MET  178     -31.639  30.737  47.651  1.00  17.28
ATOM   1267  CB   MET  178     -32.343  31.919  46.980  1.00   9.92
ATOM   1268  CA   MET  178     -32.991  32.789  48.077  1.00  11.19
ATOM   1269  C    MET  178     -33.372  34.163  47.572  1.00  14.99
ATOM   1270  O    MET  178     -32.631  35.161  47.724  1.00  16.24
ATOM   1271  N    VAL  179     -34.492  34.273  46.870  1.00  12.66
ATOM   1272  CG2  VAL  179     -35.871  34.516  44.214  1.00  11.56
ATOM   1273  CG1  VAL  179     -36.995  36.540  45.154  1.00  16.31
ATOM   1274  CB   VAL  179     -36.242  35.254  45.495  1.00  14.06
ATOM   1275  CA   VAL  179     -34.973  35.549  46.347  1.00  14.10
ATOM   1276  C    VAL  179     -35.411  36.462  47.516  1.00  17.87
ATOM   1277  O    VAL  179     -35.152  37.674  47.535  1.00  18.01
ATOM   1278  N    ASN  180     -36.139  35.872  48.451  1.00  17.87
ATOM   1279  ND2  ASN  180     -39.996  35.004  49.792  1.00  34.66
ATOM   1280  OD1  ASN  180     -39.173  36.590  48.442  1.00  26.20
ATOM   1281  CG   ASN  180     -39.030  35.860  49.435  1.00  27.22
ATOM   1282  CB   ASN  180     -37.798  35.850  50.334  1.00  22.46
ATOM   1283  CA   ASN  180     -36.683  36.628  49.576  1.00  21.81
ATOM   1284  C    ASN  180     -35.663  37.122  50.588  1.00  22.21
ATOM   1285  O    ASN  180     -35.786  38.276  51.007  1.00  25.30
ATOM   1286  N    SER  181     -34.775  36.258  50.952  1.00  20.13
ATOM   1287  OG   SER  181     -34.362  34.891  53.477  1.00  46.23
ATOM   1288  CB   SER  181     -33.268  35.230  52.620  1.00  29.26
ATOM   1289  CA   SER  181     -33.740  36.530  51.921  1.00  20.62
ATOM   1290  C    SER  181     -32.474  37.109  51.355  1.00  20.10
ATOM   1291  O    SER  181     -31.914  37.915  52.104  1.00  20.08
ATOM   1292  N    TRP  182     -32.042  36.665  50.186  1.00  17.06
ATOM   1293  CD2  TRP  182     -28.744  33.771  49.582  1.00  20.91
ATOM   1294  CE3  TRP  182     -28.470  33.240  48.331  1.00  15.11
ATOM   1295  CZ3  TRP  182     -27.853  31.999  48.269  1.00  15.36
ATOM   1296  CH2  TRP  182     -27.529  31.313  49.436  1.00  15.65
ATOM   1297  CZ2  TRP  182     -27.769  31.806  50.713  1.00  19.64
ATOM   1298  CE2  TRP  182     -28.381  33.057  50.742  1.00  24.59
ATOM   1299  NE1  TRP  182     -28.738  33.820  51.828  1.00  27.77
ATOM   1300  CD1  TRP  182     -29.323  34.986  51.373  1.00  29.42
ATOM   1301  CG   TRP  182     -29.377  35.009  50.004  1.00  22.91
ATOM   1302  CB   TRP  182     -29.884  36.098  49.127  1.00  20.07
ATOM   1303  CA   TRP  182     -30.771  37.210  49.681  1.00  14.46
ATOM   1304  C    TRP  182     -30.992  38.306  48.680  1.00  14.45
ATOM   1305  O    TRP  182     -30.007  38.974  48.321  1.00  16.23
ATOM   1306  N    GLY  183     -32.203  38.445  48.182  1.00  13.61
ATOM   1307  CA   GLY  183     -32.431  39.519  47.179  1.00  13.59
ATOM   1308  C    GLY  183     -31.864  39.105  45.800  1.00  12.98
ATOM   1309  O    GLY  183     -31.478  40.015  45.005  1.00  11.51
ATOM   1310  N    VAL  184     -31.805  37.788  45.559  1.00  12.12
ATOM   1311  CG2  VAL  184     -31.741  34.892  44.375  1.00  20.41
ATOM   1312  CG1  VAL  184     -29.458  35.739  44.931  1.00  20.83
ATOM   1313  CB   VAL  184     -30.729  35.966  44.088  1.00  14.52
```

```
ATOM   1314  CA   VAL   184      -31.288   37.397   44.216  1.00  13.35
ATOM   1315  C    VAL   184      -32.431   37.647   43.201  1.00  13.39
ATOM   1316  O    VAL   184      -33.619   37.490   43.538  1.00  13.79
ATOM   1317  N    ARG   185      -32.041   37.991   41.974  1.00  11.85
ATOM   1318  NH2  ARG   185      -31.382   44.754   43.270  1.00  30.49
ATOM   1319  NH1  ARG   185      -30.633   44.370   41.110  1.00  29.76
ATOM   1320  CZ   ARG   185      -31.320   43.982   42.177  1.00  30.81
ATOM   1321  NE   ARG   185      -31.986   42.816   42.217  1.00  27.27
ATOM   1322  CD   ARG   185      -31.978   41.937   41.036  1.00  23.48
ATOM   1323  CG   ARG   185      -32.959   40.840   41.410  1.00  19.17
ATOM   1324  CB   ARG   185      -32.789   39.732   40.349  1.00  14.23
ATOM   1325  CA   ARG   185      -32.980   38.274   40.869  1.00  11.15
ATOM   1326  C    ARG   185      -32.746   37.319   39.703  1.00   8.87
ATOM   1327  O    ARG   185      -31.721   37.472   39.065  1.00   8.01
ATOM   1328  N    LEU   186      -33.644   36.370   39.444  1.00   9.17
ATOM   1329  CA   LEU   186      -33.463   35.447   38.328  1.00   9.78
ATOM   1330  C    LEU   186      -33.503   36.225   36.995  1.00  10.75
ATOM   1331  O    LEU   186      -34.316   37.132   36.787  1.00  10.04
ATOM   1332  CB   LEU   186      -34.648   34.435   38.305  1.00   8.11
ATOM   1333  CG   LEU   186      -34.760   33.549   39.546  1.00  16.49
ATOM   1334  CD1  LEU   186      -35.699   32.375   39.276  1.00  14.66
ATOM   1335  CD2  LEU   186      -33.400   32.928   39.887  1.00  16.56
ATOM   1336  N    ARG   187      -32.652   35.750   36.102  1.00   7.79
ATOM   1337  NH2  ARG   187      -30.740   39.908   29.630  1.00  46.94
ATOM   1338  NH1  ARG   187      -29.232   39.169   31.188  1.00  49.29
ATOM   1339  CZ   ARG   187      -30.477   39.174   30.718  1.00  44.29
ATOM   1340  NE   ARG   187      -31.443   38.474   31.338  1.00  36.97
ATOM   1341  CD   ARG   187      -31.199   37.750   32.536  1.00  28.81
ATOM   1342  CG   ARG   187      -31.219   36.300   32.604  1.00  27.43
ATOM   1343  CB   ARG   187      -31.340   35.889   34.068  1.00  12.14
ATOM   1344  CA   ARG   187      -32.653   36.298   34.718  1.00   9.41
ATOM   1345  C    ARG   187      -33.901   35.672   34.023  1.00  10.55
ATOM   1346  O    ARG   187      -34.139   34.427   33.990  1.00  10.23
ATOM   1347  N    THR   188      -34.769   36.530   33.478  1.00   9.32
ATOM   1348  CA   THR   188      -35.996   36.175   32.723  1.00  10.52
ATOM   1349  C    THR   188      -35.889   36.694   31.263  1.00  11.51
ATOM   1350  O    THR   188      -34.786   37.058   30.810  1.00  10.45
ATOM   1351  CB   THR   188      -37.361   36.593   33.422  1.00   7.88
ATOM   1352  OG1  THR   188      -37.427   38.057   33.443  1.00   7.10
ATOM   1353  CG2  THR   188      -37.581   36.118   34.850  1.00   8.10
ATOM   1354  OXT  THR   188      -36.851   36.451   30.513  1.00  13.52
```

Fig. 2

PROTEASE VARIANTS

CROSS-REFERENCE TO RELATED APPLICATIONS

This application is a divisional of U.S. application Ser. No. 12/984,826 filed on Jan. 5, 2011, now U.S. Pat. No. 8,377,677, which is a divisional of U.S. application Ser. No. 10/574,554 filed on Apr. 3, 2006, now U.S. Pat. No. 7,892,808, which is a 35 U.S.C. 371 national application of PCT/DK2004/000688 filed Oct. 8, 2004, which claims priority or the benefit under 35 U.S.C. 119 of Danish application nos. PA 2003 01494 and PA 2004 00333 filed Oct. 10, 2003 and Mar. 1, 2004, respectively, and U.S. provisional application Nos. 60/510,450 and 60/549,347 filed Oct. 10, 2003 and Mar. 2, 2004, respectively, the contents of which are fully incorporated herein by reference.

FIELD OF THE INVENTION

The present invention relates to a novel protease 3D structure, as well as variants of a parent protease, in particular variants of amended properties, such as improved thermostability and/or amended temperature activity profile. The invention also relates to DNA sequences encoding such variants, their production in a recombinant host cell, as well as methods of using the variants, in particular within the field of animal feed and detergents. The invention furthermore relates to methods of generating and preparing protease variants of amended properties. Preferred parent proteases are *Nocardiopsis* proteases, such as proteases comprising the mature peptide parts of SEQ ID NOs: 2, 4, 6, 8, 10, and 21.

BACKGROUND OF THE INVENTION

Protease sequences derived from strains of *Nocardiopsis* are disclosed in WO 88/03947, WO 01/58276, and DK 1996 00013 ("Protease 10," SEQ ID NOs: 1-2).

JP 2003284571-A discloses, as SEQ ID NOs: 2 and 1, the amino acid sequence and the corresponding DNA sequence, respectively, of a protease derived from *Nocardiopsis* sp. TOA-1 (FERM P-18676). The sequences have been entered in the GENESEQ database as GENESEQP no. ADF43564 and GENESEQN no. ADF43563, respectively.

JP 2-255081-A discloses a protease derived from *Nocardiopsis* sp. strain OPC-210 (FERM P-10508), however without sequence information. The strain is no longer available, as the deposit was withdrawn.

DD 20043218 discloses a proteolytic preparation derived from *Nocardiopsis dassonvillei* strain ZIMET 43647, however without sequence information. The strain appears to be no longer available.

Additional *Nocardiopsis* protease sequences are disclosed in PCT/DK04/000433 ("Protease 08," SEQ ID NOs: 9-10); PCT/DK04/000434 ("Protease 11," SEQ ID NOs: 5-6 herein); PCT/DK04/000432 ("Protease 18," SEQ ID NOs: 3-4); and PCT/DK04/000435 ("Protease 35," SEQ ID NOs: 7-8).

It is an object of the present invention to provide alternative proteases, in particular for use in animal feed and/or detergents, in particular novel and improved protease variants, preferably of amended properties, such as improved thermostability and/or a higher or lower optimum temperature.

SUMMARY OF THE INVENTION

The present invention relates to a variant of a parent protease, comprising a substitution in at least one position of at least one region selected from the group of regions consisting of: 6-18; 22-28; 32-39; 42-58; 62-63; 66-76; 78-100; 103-106; 111-114; 118-131; 134-136; 139-141; 144-151; 155-156; 160-176; 179-181; and 184-188; wherein (a) the variant has protease activity; and
(b) each position corresponds to a position of amino acids 1 to 188 of SEQ ID NO: 2; and
(c) the variant has a percentage of identity to amino acids 1 to 188 of SEQ ID NO: 2 of at least 60%.

The present invention also relates to isolated nucleic acid sequences encoding the protease variant and to nucleic acid constructs, vectors, and host cells comprising the nucleic acid sequences as well as methods for producing and using the protease variants.

BRIEF DESCRIPTION OF THE FIGURES

FIG. 1 is a multiple alignment of Protease 10, Protease 18, Protease 11, Protease 35 and Protease 08 (the mature peptide parts of SEQ ID NOs: 2, 4, 6, 8 and 10, respectively), also including a protease variant of the invention, viz. Protease 22 (amino acids 1-188 of SEQ ID NO: 21); and FIG. 2 provides the coordinates of the novel 3D structure of Protease 10 (amino acids 1 to 188 of SEQ ID NO: 2) derived from *Nocardiopsis* sp. NRRL 18262.

DETAILED DESCRIPTION OF THE INVENTION

Three-Dimensional Structure of Protease 10

The structure of Protease 10 was solved in accordance with the principles for X-ray crystallographic methods as given, for example, in X-Ray Structure Determination, Stout, G. K. and Jensen, L. H., John Wiley & Sons, Inc. NY, 1989. The structural coordinates for the crystal structure at 2.2 Å resolution using the isomorphous replacement method are given in FIG. 2 in standard PDB format (Protein Data Bank, Brookhaven National Laboratory, Brookhaven, Conn.). The PDB file of FIG. 2 relates to the mature peptide part of Protease 10 corresponding to residues 1-188 of SEQ ID NO: 2.

Molecular Dynamics (MD)

Molecular Dynamics (MD) simulations are indicative of the mobility of the amino acids in a protein structure (see McCammon, J A and Harvey, S C., 1987, "Dynamics of proteins and nucleic acids", Cambridge University Press). Such protein dynamics are often compared to the crystallographic B-factors (see Stout, G H and Jensen, L H, 1989, "X-ray structure determination", Wiley). By running the MD simulation at, e.g., different temperatures, the temperature related mobility of residues is simulated. Regions having the highest mobility or flexibility (here isotropic fluctuations) may be suggested for random mutagenesis. It is here understood that the high mobility found in certain areas of the protein, may be thermally improved by substituting these residues.

Using the programs CHARMM (Accelrys) and NAMD (University of Illinois at Urbana-Champaign) the Protease 10 structure described above was subjected to MD at 300 and 400K. Starting from the coordinates of FIG. 2 hydrogen and missing heavy atoms were built using CHARMM procedures HBUILD and IC BUILD respectively. Then the structure was minimized using CHARMM Conjugate Gradients (CONJ) minimization procedure for a total of 200 steps. The protein was then put on a 70×70×70 Angstrom box and solvated with TIP3 water molecules. A total of 11124 water molecules were added and then minimized, keeping the protein coordinates fixed, using CHARMM Adopted Basis Newton Raphson (ABNR) minimization procedure for 20000 steps. The system was then heated to the desired temperature at a rate of 1K every 100 steps using the NAMD software. After an equilibration of 50 picoseconds, an NVE ensemble MD was run for 1 nanosecond, both steps done with the software NAMD. A cut-off of 12 Angstrom was used for the non-bonded interactions. Periodic boundary conditions were used after the solvation step and for all the subsequent ones. The isotropic root mean square (RMS) fluctuations were calculated with the CHARMM procedure COOR DYNA.

The following suggested regions for mutagenesis result from MD simulations: From residue 160 to 170, from residue 78 to 90, from residue 43 to 50, from residue 66 to 75, and from residue 22 to 28.

Strategy for Preparing Variants

Regions of amino acid residues, as well as individual amino acid substitutions, were suggested for mutagenesis based on the 3D-structure of FIG. 2 and the alignment of the five known proteases (upper five rows of FIG. 1), mainly with a view to improving thermostability.

The following regions were suggested, cf. claim 1: 6-18; 22-28; 32-39; 42-58; 62-63; 66-76; 78-100; 103-106; 111-114; 118-131; 134-136; 139-141; 144-151; 155-156; 160-176; 179-181; and 184-188.

At least one of the following positions of the above regions are preferably subjected to mutagenesis, cf. claim 3; 6; 7; 8; 9; 10; 12; 13; 16; 17; 18; 22; 23; 24; 25; 26; 27; 28; 32; 33; 37; 38; 39; 42; 43; 44; 45; 46; 47; 48; 49; 50; 51; 52; 53; 54; 55; 56; 58; 62; 63; 66; 67; 68; 69; 70; 71; 72; 73; 74; 75; 76; 78; 79; 80; 81; 82; 83; 84; 85; 86; 87; 88; 89; 90; 91; 92; 93; 94; 95; 96; 97; 98; 99; 100; 103; 105; 106; 111; 113; 114; 118; 120; 122; 124; 125; 127; 129; 130; 131; 134; 135; 136; 139; 140; 141; 144; 145; 146; 147; 148; 149; 150; 151; 155; 156; 160; 161; 162; 163; 164; 165; 166; 167; 168; 169; 170; 171; 172; 173; 174; 175; 176; 179; 180; 181; 184; 185; 186; 187; and/or 188.

Contemplated specific variants are listed in the claims, viz. variants of Protease 10, Protease 18, Protease 11, Protease 35 as well as Protease 08 in claims 4 and 15; variants of Protease 10 in claim 16; variants of Protease 18 in claim 17; variants of Protease 11 in claim 18; variants of Protease 35 in claim 19; and variants of Protease 08 in claim 20.

The various concepts underlying the invention are also reflected in the claims as follows: Stabilization by disulfide-bridges in claims 5 and 6; proline-stabilization in claims 7-8; substitution of exposed neutral residues with negatively charged residues in claims 9-10; substitution of exposed neutral residues with positively charged residues in claims 11-12; substitution of small residues with bulkier residues inside the protein in claim 13; and regions proposed for mutagenesis following MD simulations in claim 14.

The term "at least one" means "one or more," viz., e.g., in the context of regions: One, two, three, four, five, six, seven, eight, nine, ten, eleven, twelve, thirteen, fourteen, fifteen, sixteen, or seventeen; or, in the context of positions or substitutions: One, two, three, four, five, and so on, up to, e.g., ninety.

In a particular embodiment, the number of regions proposed for and/or subjected to mutagenesis is at least one, two, three, four, five, six, seven, eight, nine, ten, eleven, twelve, thirteen, fourteen, fifteen, sixteen, or at least seventeen.

In another particular embodiment, the number of regions proposed for and/or subjected to mutagenesis is no more than one, two, three, four, five, six, seven, eight, nine, ten, eleven, twelve, thirteen, fourteen, fifteen, sixteen, or no more than seventeen.

Polypeptides Having Protease Activity

Polypeptides having protease activity, or proteases, are sometimes also designated peptidases, proteinases, peptide hydrolases, or proteolytic enzymes. Proteases may be of the exo-type that hydrolyze peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in *Eur. J. Biochem.* 223: 1-5 (1994); *Eur. J. Biochem.* 232: 1-6 (1995); *Eur. J. Biochem.* 237: 1-5 (1996); *Eur. J. Biochem.* 250:1-6 (1997); and *Eur. J. Biochem.* 264: 610-650 (1999); respectively. The nomenclature is regularly supplemented and updated; see, e.g., the World Wide Web (WWW) at chem.qmw.ac.uk/iubmb/enzyme/index.html.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In particular embodiments, the parent proteases and/or the protease variants of the invention and for use according to the invention are selected from the group consisting of:

(a) Proteases belonging to the EC 3.4.-.- enzyme group;

(b) Serine proteases belonging to the S group of the above Handbook;

(c1) Serine proteases of peptidase family S2A; and (c2) Serine proteases of peptidase family S1E as described in *Biochem. J.* 290: 205-218 (1993) and in MEROPS protease database, release 6.20, Mar. 24, 2003 (merops.ac.uk). The database is described in Rawlings et al., 2002, MEROPS: the protease database, *Nucleic Acids Res.* 30: 343-346.

For determining whether a given protease is a Serine protease, and a family S2A protease, reference is made to the above Handbook and the principles indicated therein. Such determination can be carried out for all types of proteases, be it naturally occurring or wild-type proteases; or genetically engineered or synthetic proteases.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Examples of protease substrates are casein, such as Azurine-Crosslinked Casein (AZCL-casein). Examples of suitable protease assays are described in the experimental part.

Parent Protease

The parent protease is a protease from which the protease variant is, or can be, derived. For the present purposes, any protease can be used as the parent protease, as long as the resulting protease variant is homologous to Protease 10, i.e., the protease derived from *Nocardiopsis* sp. NRRL 18262 and comprising amino acids 1-188 of SEQ ID NO: 2.

In a particular embodiment the parent protease is also homologous to Protease 10.

In the present context, homologous means having an identity of at least 60% to SEQ ID NO: 2, viz. amino acids 1-188 of the mature peptide part of Protease 10. Homology is determined as generally described below in the section entitled Amino Acid Homology.

The parent protease may be a wild-type or naturally occurring polypeptide, or an allelic variant thereof, or a fragment thereof that has protease activity, in particular a mature part thereof. It may also be a variant thereof and/or a genetically engineered or synthetic polypeptide.

In a particular embodiment the wild-type parent protease is i) a bacterial protease; ii) a protease of the phylum Actinobacteria; iii) of the class Actinobacteria; iv) of the order Actinomycetales v) of the family Nocardiopsaceae; vi) of the genus *Nocardiopsis*; and/or a protease derived from vii) *Nocardiopsis* species, such as *Nocardiopsis alba, Nocardiopsis antarctica, Nocardiopsis composta, Nocardiopsis dassonvillei, Nocardiopsis exhalans, Nocardiopsis halophila, Nocardiopsis halotolerans, Nocardiopsis kunsanensis, Nocardiopsis listed, Nocardiopsis lucentensis, Nocardiopsis metallicus, Nocardiopsis prasina, Nocardiopsis sp., Nocardiopsis synnemataformans, Nocardiopsis trehalosi, Nocardiopsis tropica, Nocardiopsis umidischolae,* or *Nocardiopsis xinjiangensis.*

Examples of such strains are: *Nocardiopsis alba* DSM 15647 (wild-type producer of Protease 08), Nocardiopsis dassonvillei NRRL 18133 (wild-type producer of Protease M58-1 described in WO 88/03947), *Nocardiopsis dassonvillei* subsp. *dassonvillei* DSM 43235 (wild-type producer of Protease 18), *Nocardiopsis prasina* DSM 15648 (wild-type producer of Protease 11), *Nocardiopsis prasina* DSM 15649 (wild-type producer of Protease 35), *Nocardiopsis* sp. NRRL 18262 (wild-type producer of Protease 10), *Nocardiopsis* sp. FERM P-18676 (described in JP 2003284571-A).

Strains of these species are accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL), e.g., *Nocardiopsis dassonvillei* subsp. *dassonvillei* DSM 43235 is publicly available from DSMZ (Deutsche Sammlung von Mikroorganismen und Zellkulturen GmbH, Braunschweig, Germany).

Furthermore, such polypeptides may be identified and obtained from other sources including microorganisms or DNA isolated from nature (e.g., soil, composts, water, etc.) using suitable probes. Techniques for isolating microorganisms or DNA from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The parent protease may be a mature part of any of the amino acid sequences referred to above. A mature part means a mature amino acid sequence and refers to that part of an amino acid sequence which remains after a potential signal peptide part and/or pro-peptide part has been cleaved off. The mature parts of each of the proteases Protease 08, 10, 11, 18, 22 and 35 are specified in the sequence listing.

The parent protease may also be a fragment of a specified amino acid sequence, viz. a polypeptide having one or more amino acids deleted from the amino and/or carboxyl terminus of this amino acid sequence. In one embodiment, a fragment contains at least 80, or at least 90, or at least 100, or at least 110, or at least 120, or at least 130, or at least 140, or at least 150, or at least 160, or at least 170, or at least 180, or at least 185 amino acid residues.

The parent protease may also be an allelic variant, allelic referring to the existence of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In another embodiment, the parent protease may be a genetically engineered protease, e.g., a variant of the wild-type or natural parent proteases referred to above comprising a substitution, deletion, and/or insertion of one or more amino acids. In other words: The parent protease may itself be a protease variant, such as Protease 22. The amino acid sequence of such parent protease may differ from the amino acid sequence specified by an insertion or deletion of one or more amino acid residues and/or the substitution of one or more amino acid residues by different amino acid residues. The amino acid changes may be of a minor, or of a major, nature. Amino acid changes of a major nature are, e.g., those resulting in a variant protease of the present invention with amended properties. In another particular embodiment, the amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

Still further examples of genetically engineered parent proteases are synthetic proteases, designed by man, and expectedly not occurring in nature. EP 897985 discloses a process of preparing a consensus protein. Shuffled proteases are other examples of synthetic or genetically engineered parent proteases, which can be prepared as is generally known in the art, eg by Site-directed Mutagenesis, by PCR (using a PCR fragment containing the desired mutation as one of the primers in the PCR reactions), or by Random Mutagenesis. Included in the concept of a synthetic protease is also any hybrid or chimeric protease, i.e., a protease which comprises a combination of partial amino acid sequences derived from at least two proteases. Gene shuffling is generally described in, e.g., WO 95/22625 and WO 96/00343. Re-combination of protease genes can be made independently of the specific sequence of the parents by synthetic shuffling as described in Ness et al. 2002, *Nature Biotechnology* 20(12): 1251-1255. Synthetic oligonucleotides degenerated in their DNA sequence to provide the possibility of all amino acids found in the set of parent proteases are designed and the genes assembled according to the reference. The shuffling can be carried out for the full length sequence or for only part of the sequence and then later combined with the rest of the gene to give a full length sequence. Two, three, four, five or all six of the proteases designated Protease 10, 18, 11, 35, 08 and 22 (SEQ ID NOs: 2, 4, 6, 8, 10, and 21; in particular the mature parts thereof) are particular examples of such parent proteases which can be subjected to shuffling as described above, to provide additional proteases of the invention.

In further particular embodiments, the parent protease comprises, or consists of, respectively, the amino acid sequence specified, or an allelic variant thereof; or a fragment thereof that has protease activity.

In still further particular embodiments, the protease variant of the invention is not identical to: (i) amino acids 1-188 of SEQ ID NO: 2, amino acids 1-188 of SEQ ID NO: 4, amino acids 1-188 of SEQ ID NO: 6, amino acids 1-188 of SEQ ID NO: 8, and amino acids 1-188 of SEQ ID NO: 10; (ii) amino acids 1-188 of SEQ ID NO: 2; (iii) amino acids 1-188 of SEQ ID NO: 2 with the substitution T87A; (iv) amino acids 1-188 of SEQ ID NO: 4; (v) amino acids 1-188 of SEQ ID NO: 6; (vi) amino acids 1-188 of SEQ ID NO: 8; (vii) amino acids 1-188 of SEQ ID NO: 10; (viii) the protease derived from *Nocardiopsis dassonvillei* NRRL 18133; (ix) the protease having amino acids 1 to 188 of SEQ ID NO: 2 as disclosed in JP 2003284571-A; (x) the protease having the sequence entered in GENESEQP with no. ADF43564; (xi) the protease disclosed in DK patent application no. PA 2004 00969 as SEQ ID NO: 2, in particular the mature part thereof; (xii) the protease disclosed in DK patent application no. PA 2004 00969 as SEQ ID NO: 4, in particular the mature part thereof; (xiii) the protease disclosed in DK patent application no. PA 2004 00969 as SEQ ID NO: 6, in particular the mature part thereof; (xiv) the protease disclosed in DK patent application no. 2004 00969 as SEQ ID NO: 8, in particular the mature part thereof; (xv) the protease disclosed in DK patent application no. PA 2004 00969 as SEQ ID NO: 10, in particular the mature part thereof; (xvi) the protease disclosed in DK patent application no. PA 2004 00969 as SEQ ID NO: 12, in particular the mature part thereof; and/or (xvii) any prior art protease of a percentage of identity to SEQ ID NO: 2 of at least 60%.

Microorganism Taxonomy

Questions relating to taxonomy may be solved by consulting a taxonomy data base, such as the NCBI Taxonomy Browser which is available at the following internet site: www.ncbi.nlm.nih.gov/Taxonomy/taxonomyhome.html, and/or by consulting Taxonomy handbooks. For the present purposes, the taxonomy is preferably according to the chapter: The road map to the Manual by G. M. Garrity & J. G. Holt in Bergey's Manual of Systematic Bacteriology, 2001, second edition, volume 1, David R. Bone, Richard W. Castenholz.

Amino Acid Homology

The present invention refers to proteases, viz. parent proteases, and/or protease variants, having a certain degree of identity to amino acids 1 to 188 of SEQ ID NO: 2, such parent and/or variant proteases being hereinafter designated "homologous proteases".

For purposes of the present invention the degree of identity between two amino acid sequences, as well as the degree of identity between two nucleotide sequences, is determined by the program "align" which is a Needleman-Wunsch alignment (i.e., a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides "Align" is part of the FASTA package version v20u6 (see Pearson and. Lipman, 1988, "Improved Tools for Biological Sequence Analysis", *PNAS* 85:2444-2448, and Pearson, 1990, "Rapid and Sensitive Sequence Comparison with FASTP and FASTA," *Methods in Enzymology* 183:63-98). FASTA protein alignments use the Smith-Waterman algorithm with no limitation on gap size (see "Smith-Waterman algorithm", Smith and Waterman, 1981, *J. Mol. Biol.* 147: 195-197).

Multiple alignments of protein sequences may be made using "ClustalW" (Thompson, et al., 1994, CLUSTAL W: improving the sensitivity of progressive multiple sequence alignment through sequence weighting, positions-specific gap penalties and weight matrix choice, *Nucleic Acids Research* 22:4673-4680). Multiple alignment of DNA sequences may be done using the protein alignment as a template, replacing the amino acids with the corresponding codon from the DNA sequence.

In particular embodiments, the homologous protease has an amino acid sequence which has a degree of identity to amino acids 1 to 188 of SEQ ID NO: 2 of at least 60%, 62%, 64%, 66%, 68%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or of at least about 99%.

In alternative embodiments, the homologous protease has an amino acid sequence which has a degree of identity to SEQ ID NO: 2 of at least 50%, 51%, 52%, 53%, 54%, 55%, 56%, 57%, 58%, or at least 59%.

In another particular embodiment, the parent protease, and/or the protease variant, comprises a mature amino acid sequence which differs by no more than seventyfive, seventyfour, seventythree, seventytwo, seventyone, seventy, sixtynine, sixtyeight, sixtyseven, sixtysix, sixtyfive, sixtyfour, sixtythree, sixtytwo, sixtyone, sixty, fiftynine, fiftyeight, fiftyseven, fiftysix, fiftyfive, fiftyfour, fiftythree, fiftytwo, fiftyone, fifty, fortynine, fortyeight, fortyseven, fortysix, fortyfive, fortyfour, fortythree, fortytwo, fortyone, forty, thirtynine, thirtyeight, thirtyseven, thirtysix, thirtyfive, thirtyfour, thirtythree, thirtytwo, thirtyone, thirty, twentynine, twentyeight, twentyseven, twentysix, twentyfive, twentyfour, twentythree, twentytwo, twentyone, twenty, nineteen, eighteen, seventeen, sixteen, fifteen, fourteen, thirteen, twelve, eleven, ten, nine, eight, seven, six, five, four, three, by no more than two, or only by one amino acid(s) from the specified amino acid sequence, e.g., amino acids 1 to 188 of SEQ ID NO: 2.

In a still further particular embodiment, the parent protease, and/or the protease variant, comprises a mature amino acid sequence which differs by at least seventyfive, seventyfour, seventythree, seventytwo, seventyone, seventy, sixtynine, sixtyeight, sixtyseven, sixtysix, sixtyfive, sixtyfour, sixtythree, sixtytwo, sixtyone, sixty, fiftynine, fiftyeight, fiftyseven, fiftysix, fiftyfive, fiftyfour, fiftythree, fiftytwo, fiftyone, fifty, fortynine, fortyeight, fortyseven, fortysix, fortyfive, fortyfour, fortythree, fortytwo, fortyone, forty, thirtynine, thirtyeight, thirtyseven, thirtysix, thirtyfive, thirtyfour, thirtythree, thirtytwo, thirtyone, thirty, twentynine, twentyeight, twentyseven, twentysix, twentyfive, twentyfour, twentythree, twentytwo, twentyone, twenty, nineteen, eighteen, seventeen, sixteen, fifteen, fourteen, thirteen, twelve, eleven, ten, nine, eight, seven, six, five, four, three, by at least two, or by one amino acid(s) from the specified amino acid sequence, e.g., amino acids 1 to 188 of SEQ ID NO: 2.

Nucleic Acid Hybridization

In the alternative, homologous parent proteases, as well as variant proteases, may be defined as being encoded by a nucleic acid sequence which hybridizes under very low stringency conditions, preferably low stringency conditions, more preferably medium stringency conditions, more preferably medium-high stringency conditions, even more preferably high stringency conditions, and most preferably very high stringency conditions with nucleotides 900-1466, or 900-1463, of SEQ ID NO: 1, or a subsequence or a complementary strand thereof (J. Sambrook, E. F. Fritsch, and T. Maniatus, 1989, Molecular Cloning, A Laboratory Manual, 2d edition, Cold Spring Harbor, N.Y.). A subsequence may be at least 100 nucleotides, or at least 200, 300, 400, or at least 500 nucleotides. Moreover, the subsequence may encode a polypeptide fragment that has the relevant enzyme activity.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

Position Numbering

In the present context, the basis for numbering positions is amino acids 1 to 188 of SEQ ID NO: 2, Protease 10, starting with A1 and ending with T188, see FIG. 1. A parent protease, as well as a variant protease, may comprise extensions as compared to SEQ ID NO: 2, i.e., in the N-terminal, and/or the C-terminal ends thereof. The amino acids of such extensions, if any, are to be numbered as is usual in the art, i.e., for a C-terminal extension: 189, 190, 191 and so forth, and for an N-terminal extension −1, −2, −3 and so forth.

Alterations, Such as Substitutions, Deletions, Insertions

In the present context, the following are examples of various ways in which a protease variant can be designed or derived from a parent amino acid sequence: An amino acid can be substituted with another amino acid; an amino acid can be deleted; an amino acid can be inserted; as well as any combination of any number of such alterations.

For the present purposes, the term substitution is intended to include any number of any type of such alterations. This is a reasonable definition, because, for example, a deletion can be regarded as a substitution of an amino acid, AA, in a given position, nn, with nothing, ( ). Such substitution can be designated: AAnn( ). Likewise, an insertion of only one amino acid, BB, downstream an amino acid, AA, in a given position, nn, can be designated: ( )naBB. And if two amino acids, BB and CC, are inserted downstream of amino acid AA in position nn, this substitution (combination of two substitutions) can be designated: ( )naBB+( )nbCC, the thus created gaps between amino acids nn and nn+1 in the parent sequence being assigned lower case or subscript letters a, b, c etc. to the former position number, here nn. A similar numbering procedure is followed when aligning a new sequence to the multiple alignment of FIG. 1, in case of a gap being created by the alignment between amino acids nn and nn+1: Each position of the gap is assigned a number: nna, nnb etc. A comma (,) between substituents, as, e.g., in the substitution T129E, D,Y,Q means "either or", i.e., that T129 is substituted with E, or D, or Y, or Q. A plus-sign (+) between substitutions, e.g., 129D+135P means "and", i.e., that these two single substitutions are combined in one and the same protease variant.

In the present context, the term "a" substitution" means at least one substitution. At least one means one or more, e.g., one, or two, or three, or four, or five, or six, or seven, or eight, or nine, or ten, or twelve, or fourteen, or fifteen, or sixteen, or eighteen, or twenty, or twentytwo or twentyfour, or twentyfive, or twenty eight, or thirty, and so on, to include in principle, any number of substitutions. The variants of the invention, however, still have to be, e.g., at least 60% identical to SEQ ID NO: 2, this percentage being determined by the above-mentioned program. The substitutions can be applied to any position encompassed by any region mentioned in claim 1, and variants comprising combinations of any number and type of such substitutions are also included. The term substitution as used herein also include deletions, as well as extensions, or insertions, that may add to the length of the sequence corresponding to amino acids 1 to 188 of SEQ ID NO: 2.

Furthermore, the term "a substitution" embraces a substitution into any one of the other nineteen natural amino acids, or into other amino acids, such as non-natural amino acids. For example, a substitution of amino acid T in position 22 includes each of the following substitutions: 22A, 22C, 22D, 22E, 22F, 22G, 22H, 22I, 22K, 22L, 22M, 22N, 22P, 22Q, 22R, 22S, 22V, 22W, and 22Y. This is, by the way, equivalent to the designation 22x, wherein X designates any amino acid. These substitutions can also be designated T22A, T22C, T22X, etc. The same applies by analogy to each and every position mentioned herein, to specifically include herein any one of such substitutions.

Identifying Corresponding Position Numbers

For each amino acid residue in each parent, or variant, protease of the invention, and/or for use according to the invention, it is possible to directly and unambiguously assign an amino acid residue in the sequence of amino acids 1 to 188 of SEQ ID NO: 2 to which it corresponds. Corresponding residues are assigned the same number, by reference to the Protease 10 sequence.

As it appears from the numbering of FIG. 1, in conjunction with the numbering of the sequence listing, for each amino acid residue of each of the proteases Protease 10, Protease 18, Protease 11, Protease 35, Protease 08, and Protease 22, the corresponding amino acid residue in SEQ ID NO: 2 has the same number. This number is easily derivable from FIG. 1. At least in case of these six proteases, the number is the same as the number assigned to this amino acid residue in the sequence listing for the mature part of the respective protease.

For a given position in another protease—be it a parent or a variant protease—a corresponding position of SEQ ID NO: 2 can always be found, as follows:

The amino acid sequence of another parent protease, or, in turn, of a variant protease amino acid sequence, is designated SEQ-X. A position corresponding to position N of SEQ ID NO: 2 is found as follows: The parent or variant protease amino acid sequence SEQ-X is aligned with SEQ ID NO: 2 as specified above in the section entitled Amino Acid Homology. From the alignment, the position in sequence SEQ-X corresponding to position N of SEQ ID NO: 2 can be clearly and unambiguously derived, using the principles described below.

SEQ-X is the mature part of the protease in question. In the alternative, it may also include a signal peptide part, and/or a propeptide part, or it may be a fragment of the mature protease which has protease activity, e.g., a fragment of the same length as SEQ ID NO: 2, and/or it may be the fragment which extends from A1 to T188 when aligned with SEQ ID NO: 2 as described herein.

Region and Position

In the present context, the term region means at least one position of a parent protease amino acid sequence, the term position designating an amino acid residue of such amino acid sequence. In one embodiment, region means one or more successive positions of the parent protease amino acid sequence, e.g., one, two, three, four, five, six, seven, eight, etc., up to any number of consecutive positions of the sequence. Accordingly, a region may consist of one position only, or it may consist of any number of consecutive positions, such as, e.g., positions 62 and 63; or positions 111, 112, 113 and 114. For the present purposes, these two regions are designated 62-63, and 111-114, respectively. The boundaries of these regions or ranges are included in the region.

A region encompasses specifically each and every position it embraces. For example, region 111-114 specifically encompasses each of the positions 111, 112, 113, and 114. The same applies by analogy for the other regions mentioned herein.

Thermostability

For the present purposes, the term thermostable as applied in the context of a certain polypeptide, refers to the melting temperature, Tm, of such polypeptide, as determined using Differential Scanning calorimetry (DSC) in 10 mM sodium phosphate, 50 mM sodium chloride, pH 7.0, using a constant scan rate of 1.5° C./min.

The following Tm's were determined under the above conditions: 76.5° C. (Protease 10), 83.0° C. (Protease 18), 78.3° C. (Protease 08), 76.6° C. (Protease 35), 73.7° C. (Protease 11), and 83.5° C. (Protease 22).

For a thermostable polypeptide, the Tm is at least 83.1° C. In particular embodiments, the Tm is at least 84, 85, 86, 87, 88, 89, 90, 91, 92, 93, 94, 95, 96, 97, 98, 99 or at least 100° C.

In the alternative, the term thermostable refers to a melting temperature of at least 73.8, or at least 76.7° C., or at least 78.4° C., preferably at least 74, 75, 76, 77, 78, 79, 80, 81, 82, or at least 83° C., still as determined using DSC at a pH of 7.0.

For the determination of Tm, a sample of the polypeptide with a purity of at least 90% (or 91, 92, 93, 94, 95, 96, 97, or 98%) as determined by SDS-PAGE may be used. Still further, the enzyme sample may have a concentration of between 0.5 and 2.5 mg/ml protein (or between 0.6 and 2.4, or between 0.7 and 2.2, or between 0.8 and 2.0 mg/ml protein), as determined from absorbance at 280 nm and based on an extinction coefficient calculated from the amino acid sequence of the enzyme in question.

The DSC takes place at the desired pH (e.g., pH 5.5, 7.0, 3.0, or 2.5) and with a constant heating rate, e.g., of 1, 1.5, 2, 3, 4, 5, 6, 7, 8, 9 or 10° C./min.

In a particular embodiment, the protease variant of the invention is thermostable, preferably more thermostable than the parent protease. In this context, preferred parent proteases are Protease 18, or Protease 10.

In another particular embodiment, a culture supernatant of the protease variant of the invention, appropriately diluted, exhibits a residual activity after incubation for four hours at 65° C. in a 0.2 M $Na_2HPO_4$ buffer, titrated with 0.1 M citric acid to i) pH 6.0, or ii) pH 4.0, of at least 20%, relative to an un-incubated (frozen) control, the activity being measured using the Protazyme AK assay at pH 8.5 and 37° C., as described in Example 2. In further particular embodiments, the residual activity is at least 25, 30, 35, 40, 45, 50, 55, 60, 65, 70, 75, or at least 77%.

Temperature Activity Profile

In a particular embodiment, the protease variant of the invention exhibits an amended temperature activity profile as compared to, e.g., Protease 10 (or Protease 18, Protease 11, Protease 35, or Protease 08). For example, the protease variant of the invention may exhibit a relative activity at pH 9 and 80° C. of at least 0.40, preferably at least 0.45, 0.50, 0.55, 0.60, 0.65, 0.70, 0.75, 0.80, 0.85, 0.90, or at least 0.95, the term "relative" referring to the maximum activity measured for the protease in question. For Protease 22, the activity is relative to the activity at 80° C. which is set to 1.000 (100%), and for Protease 10, the activity at 70° C. is set to 1.000 (100%), see Example 3. As another example, the protease variant of the invention exhibits a relative activity at pH 9 and 90° C. of at least 0.10, preferably at least 0.15, 0.20, 0.25, 0.30, or of at least 0.35. In a particular embodiment, the protease activity is measured using the Protazyme AK assay of Example 1.

Low-Allergenic Variants

In a specific embodiment, the protease variants of the present invention are (also) low-allergenic variants, designed to invoke a reduced immunological response when exposed to animals, including man. The term immunological response is to be understood as any reaction by the immune system of an animal exposed to the protease variant. One type of immunological response is an allergic response leading to increased levels of IgE in the exposed animal. Low-allergenic variants may be prepared using techniques known in the art. For example the protease variant may be conjugated with polymer moieties shielding portions or epitopes of the protease variant involved in an immunological response. Conjugation with polymers may involve in vitro chemical coupling of polymer to the protease variant, e.g., as described in WO 96/17929, WO 98/30682, WO 98/35026, and/or WO 99/00489. Conjugation may in addition or alternatively thereto involve in vivo coupling of polymers to the protease variant. Such conjugation may be achieved by genetic engineering of the nucleotide sequence encoding the protease variant, inserting consensus sequences encoding additional glycosylation sites in the protease variant and expressing the protease variant in a host capable of glycosylating the protease variant, see, e.g., WO 00/26354. Another way of providing low-allergenic variants is genetic engineering of the nucleotide sequence encoding the protease variant so as to cause the protease variants to self-oligomerize, effecting that protease variant monomers may shield the epitopes of other protease variant monomers and thereby lowering the antigenicity of the oligomers. Such products and their preparation is described, e.g., in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the protease variant by known gene manipulation techniques such as site directed mutagenesis (see, e.g., WO 00/26230, WO 00/26354 and/or WO 00/22103) and/or conjugation of a polymer may be done in sufficient proximity to the epitope for the polymer to shield the epitope.

Nucleic Acid Sequences and Constructs

The present invention also relates to nucleic acid sequences comprising a nucleic acid sequence which encodes a protease variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into the parent protease coding sequence or a subsequence thereof, wherein the mutant nucleic acid sequence encodes a variant protease. The introduction of a mutation into the nucleic acid sequence to exchange one nucleotide for another nucleotide may be accomplished by site-directed mutagenesis using any of the methods known in the art, e.g., by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the protease enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent protease in question. This may, e.g., be advantageous when certain regions of the enzyme have been identified to be of particular importance for a given property of the enzyme.

Alternative methods for providing variants of the invention include gene shuffling, e.g., as described in WO 95/22625 or in WO 96/00343, and the consensus derivation process as described in EP 897985 (see the section "Parent Protease" for more details).

In particular embodiments, the nucleic acid sequence of the invention is not identical to: (i) Nucleotides 900-1466, or 900-1463, of SEQ ID NO: 1, nucleotides 499-1062 of SEQ ID NO: 3, nucleotides 496-1059 of SEQ ID NO: 5, nucleotides 496-1059 of SEQ ID NO: 7, and nucleotides 502-1065 of SEQ ID NO: 9; (ii) nucleotides 900-1466 of SEQ ID NO: 1; (iii) nucleotides 900-1463 of SEQ ID NO: 1; (iv) nucleotides 900-1463 of SEQ ID NO: 1 as disclosed in DK 1996 00013; (v) nucleotides 499-1062 of SEQ ID NO: 3; (vi) nucleotides 496-1059 of SEQ ID NO: 5; (vii) nucleotides 496-1059 of SEQ ID NO: 7; (viii) nucleotides 502-1065 of SEQ ID NO: 9; (xi) the nucleic acid sequence encoding the mature peptide part of the protease derived from *Nocardiopsis dassonvillei* NRRL 18133; (x) the nucleic acid sequence having SEQ ID NO: 1 as disclosed in JP 2003284571-A; (xi) the nucleic acid sequence GENESEQN no. ADF43563; (xii) the nucleic acid sequence disclosed in DK patent application no. PA 2004 00969 as SEQ ID NO: 1, in particular the mature peptide encoding part thereof; (xiii) the nucleic acid sequencep disclosed in DK patent application no. PA 2004 00969 as SEQ ID NO: 3, in particular the mature peptide encoding part thereof; (xiv) the nucleic acid sequence disclosed in DK patent application no. PA 2004 00969 as SEQ ID NO: 5, in particular the mature peptide encoding part thereof; (xv) the nucleic acid sequence disclosed in DK patent application no. PA 2004 00969 as SEQ ID NO: 7, in particular the mature peptide encoding part thereof; (xvi) the nucleic acid sequence disclosed in DK patent application no. PA 2004 00969 as SEQ ID NO: 9, in particular the mature peptide encoding part thereof; (xvii) the nucleic acid sequence disclosed in DK patent application no. PA 2004 00969 as SEQ ID NO: 11, in particular the mature peptide encoding part thereof; and/or (xviii) nucleic acid sequences encoding any prior art proteases of at least 60% identity to amino acids 1 to 188 of SEQ ID NO: 2.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

Expression Vector

A nucleic acid sequence encoding a protease variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a protease variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The protease variant may also be co-expressed together with at least one other enzyme of animal feed interest, such as an alpha-amylase, a phytase, a galactanase, a xylanase, an endoglucanase, an endo-1,3(4)-beta-glucanase, an alpha-galactosidase, and/or a protease. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The protease variant may also be expressed as a fusion protein, i.e., that the gene encoding the protease variant has been fused in frame to the gene encoding another protein. This protein may be another enzyme or a functional domain from another enzyme.

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote cell, such as an animal, a mammalian, an insect, a plant, or a fungal cell. Preferred animal cells are non-human animal cells.

In a preferred embodiment, the host cell is a fungal cell, or a yeast cell, such as a *Candida, Hansenula, Kluyveromyces, Pichia, Saccharomyces, Schizosaccharomyces,* or *Yarrowia* cell. The fungal host cell may be a filamentous fungal cell, such as a cell of a species of, but not limited to, *Acremonium, Aspergillus, Fusarium, Humicola, Mucor, Myceliophthora, Neurospora, Penicillium, Thielavia, Tolypocladium,* or *Trichoderma*. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis,* or a *Streptomyces* cell, such as *Streptomyces lividans* or *Streptomyces murinus,* or a *Nocardiopsis* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus,* and *Enterococcus*.

Methods of Production

The present invention also relates to methods for producing a protease variant of the present invention comprising (a) cultivating a host cell under conditions conducive for production of the protease variant; and (b) recovering the protease variant.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the protease is secreted into the nutrient medium, it can be recovered directly from the medium. If it is not secreted, it can be recovered from cell lysates.

The resulting protease may be recovered by methods known in the art. For example, it can be recovered from the nutrient medium by conventional procedures including, but not limited to, centrifugation, filtration, extraction, spray-drying, evaporation, or precipitation.

The proteases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an anti-nutritive factor.

In a particular embodiment, the polypeptide is targeted to the endosperm storage vacuoles in seeds. This can be obtained by synthesizing it as a precursor with a suitable signal peptide, see Horvath et al. in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, triticale (stabilized hybrid of wheat (Triticum) and rye (Secale), and maize (corn). Examples of dicot plants are tobacco, legumes, such as sunflower (Helianthus), cotton (Gossypium), lupins, potato, sugar beet, pea, bean and soybean, and cruciferous plants (family Brassicaceae), such as cauliflower, rape seed, and the closely related model organism *Arabidopsis thaliana*.

Low-phytate plants as described, e.g., in U.S. Pat. Nos. 5,689, 054 and 6,111,168 are examples of engineered plants.

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*. Low-phytate plants as described, e.g., in U.S. Pat. Nos. 5,689,054 and 6,111,168 are examples of engineered plants. Examples of plant parts are stem, callus, leaves, root, fruits, seeds, and tubers, as well as the individual tissues comprising these parts, e.g., epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the following promoters may be used: The 35S-CaMV promoter (Franck et al., 1980, *Cell* 21: 285-294), the maize ubiquitin 1 (Christensen A H, Sharrock R A and Quail, 1992, Maize polyubiquitin genes: structure, thermal perturbation of expression and transcript splicing, and promoter activity following transfer to protoplasts by electroporation), or the rice actin 1 promoter (*Plant Mol. Biol.* 18: 675-689; Zhang et al., 1991, Analysis of rice Act1 5' region activity in transgenic rice plants. *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may be inducible by abiotic treatments such as temperature, drought or alterations in salinity or inducible by exogenously applied substances that activate the promoter, e.g., ethanol, oestrogens, plant hormones like ethylene, abscisic acid, gibberellic acid, and/or heavy metals.

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al. referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38), and it can also be used for transforming monocots, although other transformation methods are generally preferred for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, *Plant Journal* 2: 275-281; Shimamoto, 1994, *Current Opinion in Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a protease variant of the present invention under conditions conducive for production of the protease variant; and (b) recovering the protease variant.

Animals as Expression Hosts

The present invention also relates to a transgenic, non-human animal and products or elements thereof, examples of which are body fluids such as milk and blood, organs, flesh, and animal cells. Techniques for expressing proteins, e.g., in mammalian cells, are known in the art, see, e.g., the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a protease variant of the present invention so as to express and produce the protease variant. The protease variant may be recovered from the animal, e.g., from the milk of female animals, or it may be expressed to the benefit of the animal itself, e.g., to assist the animal's digestion. Examples of animals are mentioned below in the section headed Animal Feed and Animal Feed Additives.

To produce a transgenic animal with a view to recovering the protease variant from the milk of the animal, a gene encoding the protease variant may be inserted into the fertilized eggs of an animal in question, e.g., by use of a transgene expression vector which comprises a suitable milk protein promoter, and the gene encoding the protease variant. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The protease variant may be purified from the animal's milk, see, e.g., Meade, H. M. et al., 1999, Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the protease variant, the transgene may be operably linked to a first regulatory sequence for salivary gland specific expression of the protease variant, as disclosed in WO 00/64247.

Animal Feed and Animal Feed Additives

For the present purposes, the term animal includes all animals, including human beings. In a particular embodiment, the protease variants and compositions of the invention can be used as a feed additive for non-human animals. Examples of animals are non-ruminants, and ruminants, such as sheep, goats, horses, and cattle, e.g., beef cattle, cows, and young calves. In a particular embodiment, the animal is a non-ruminant animal. Non-ruminant animals include mono-gastric animals, e.g., pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns).

The term feed or feed composition means any compound, preparation, mixture, or composition suitable for, or intended for intake by an animal. The feed can be fed to the animal before, after, or simultaneously with the diet. The latter is preferred.

The composition of the invention, when intended for addition to animal feed, may be designated an animal feed additive. Such additive always comprises the protease variant in question, preferably in the form of stabilized liquid or dry compositions. The additive may comprise other components or ingredients of animal feed. The so-called pre-mixes for animal feed are particular examples of such animal feed additives. Pre-mixes may contain the enzyme(s) in question, and in addition at least one vitamin and/or at least one mineral.

Accordingly, in a particular embodiment, in addition to the component polypeptides, the composition of the invention may comprise or contain at least one fat-soluble vitamin, and/or at least one water-soluble vitamin, and/or at least one trace mineral. Also at least one macro mineral may be included.

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

Further, optional, feed-additive ingredients are colouring agents, e.g., carotenoids such as beta-carotene, astaxanthin, and lutein; aroma compounds; stabilizers; polyunsaturated fatty acids; reactive oxygen generating species; antimicrobial peptides; and/or at least one additional enzyme.

Additional enzyme components of the invention include at least one polypeptide having amylase, preferably alpha-amylase, activity, and/or at least one polypeptide having xylanase activity; and/or at least one polypeptide having endoglucanase activity; and/or at least one polypeptide having endo-1,3(4)-beta-glucanase activity; and/or at least one polypeptide having phytase activity; and/or at least one polypeptide having galactanase activity; and/or at least one polypeptide having alpha-galactosidase activity; and/or at least one other polypeptide having protease activity (EC 3.4.-.-); and/or at least one polypeptide having phospholipase A1 (EC 3.1.1.32), phospholipase A2 (EC 3.1.1.4), lysophospholipase (EC 3.1.1.5), phospholipase C (EC 3.1.4.3), and/or phospholipase D (EC 3.1.4.4) activity.

Alpha-amylase activity can be measured as is known in the art, e.g., using a starch-based substrate.

Xylanase activity can be measured using any assay, in which a substrate is employed, that includes 1,4-beta-D-xylosidic endo-linkages in xylans. Different types of substrates are available for the determination of xylanase activity, e.g., Xylazyme cross-linked arabinoxylan tablets (from Mega-Zyme), or insoluble powder dispersions and solutions of azo-dyed arabinoxylan.

Endoglucanase activity can be determined using any endoglucanase assay known in the art. For example, various cellulose- or beta-glucan-containing substrates can be applied. An endoglucanase assay may use AZCL-Barley beta-Glucan, or preferably (1) AZCL-HE-Cellulose, or (2) Azo-CM-cellulose as a substrate. In both cases, the degradation of the substrate is followed spectrophotometrically at $OD_{595}$ (see the Megazyme method for AZCL-polysaccharides for the assay of endo-hydrolases at megazyme.com/booklets/AZCLPOL.pdf.

Endo-1,3(4)-beta-glucanase activity can be determined using any endo-1,3(4)-beta-glucanase assay known in the art. A preferred substrate for endo-1,3(4)-beta-glucanase activity measurements is a cross-linked azo-coloured beta-glucan Barley substrate, wherein the measurements are based on spectrophotometric determination principles.

Phytase activity can be measured using any suitable assay, e.g., the FYT assay described in Example 4 of WO 98/28408.

Galactanase can be assayed, e.g., with AZCL galactan from Megazyme, and alpha-galactosidase can be assayed, e.g., with pNP-alpha-galactoside.

For assaying these enzyme activities the assay-pH and the assay-temperature are to be adapted to the enzyme in question (preferably a pH close to the optimum pH, and a temperature close to the optimum temperature). A preferred assay pH is in the range of 2-10, preferably 3-9, more preferably pH 3 or 4 or 5 or 6 or 7 or 8, for example pH 3 or pH 7. A preferred assay temperature is in the range of 20-90° C., preferably 30-90° C., more preferably 40-80° C., even more preferably 40-70° C., preferably 40 or 45 or 50° C. The enzyme activity is defined by reference to appropriate blinds, e.g., a buffer blind.

Examples of antimicrobial peptides (AMP's) are CAP18, Leucocin A, Tritrpticin, Pro-tegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus* giganteus, and *Aspergillus niger* peptides, as well as variants and fragments thereof which retain antifungal activity, as disclosed in WO 94/01459 and WO 02/090384.

Examples of polyunsaturated fatty acids are 018, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

Usually fat and water soluble vitamins, as well as trace minerals form part of a so-called premix intended for addition to the feed, whereas macro minerals are usually separately added to the feed. A premix enriched with a protease of the invention, is an example of an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg. WO 01/58275 corresponds to U.S. Ser. No. 09/779,334 which is hereby incorporated by reference.

An animal feed composition according to the invention has a crude protein content of 50-800 g/kg, and furthermore comprises at least one protease variant as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or, in a particular embodiment, it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley;

and/or 0-30% oats; and/or 0-40% soybean meal; and/or 0-25%, preferably 0-10%, fish meal; 0-25% meat and bone meal; and/or 0-20% whey.

Animal diets can, e.g., be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease variant should of course be applied in an effective amount, i.e., in an amount adequate for improving solubilisation and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease enzyme protein per kg feed (ppm).

For determining mg enzyme protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg enzyme protein per kg feed is calculated.

The same principles apply for determining mg enzyme protein in feed additives. Of course, if a sample is available of the protease used for preparing the feed additive or the feed, the specific activity is determined from this sample (no need to purify the protease from the feed composition or the additive).

Detergent Compositions

The protease variant of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease variant of the invention. The detergent additive as well as the detergent composition may comprise one or more other enzymes such as another protease, such as alkaline proteases from *Bacillus*, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258068 and EP 305216 or from *H. insolens* as described in WO 96/13580, a *Pseudomonas* lipase, e.g., from *P. alcaligenes* or *P. pseudoalcaligenes* (EP 218272), *P. cepacia* (EP 331376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta* 1131: 253-360), *B. stearothermophilus* (JP 64/744992) or *B. pumilus* (WO 91/16422). Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S).

Suitable amylases (alpha- and/or beta-) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839. Examples of useful amylases are the variants described in WO 94/02597, WO 94/18314, WO 95/26397, WO 96/23873, WO 97/43424, WO 00/60060, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are Natalase™, Supramyl™, Stainzyme™, Duramyl™, Termamyl™, Fungamyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259. Especially suitable cellulases are the alkaline or neutral cellulases having colour care benefits. Examples of such cellulases are cellulases described in EP 0 495257, EP 531372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544. Commercially available cellulases include Celluzyme™, and Carezyme™ (Novozymes A/S), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liqour, preferably 0.05-5 mg of enzyme protein per liter of wash liqour, in particular 0.1-1 mg of enzyme protein per liter of wash liqour.

The enzyme of the invention may additionally be incorporated in the detergent formulations disclosed in WO 97/07202.

Method for Generating Protease Variants

The invention also relates to a method for generating a protease variant of an improved property, the method comprising the following steps:

(a) selecting a parent protease of at least 60% identity to amino acids 1 to 188 of SEQ ID NO: 2;

(b) establishing a 3D structure of the parent protease by homology modelling using the FIG. 2 structure as a model; and/or aligning the parent protease according to the alignment of FIG. 1;

(c) proposing at least one amino acid substitution, e.g., by:
  (i) subjecting the 3D structure of (b) to MD simulations at increased temperatures, and identifying regions in the amino acid sequence of the parent protease of high mobility (isotropic fluctuations);
  (ii) introducing disulfide bridges by way of cysteine substitutions (C-C);
  (iii) introducing proline substitutions (P);
  (iv) replacing exposed neutral amino acid residues with negatively charged amino acid residues (E,D);
  (v) replacing exposed neutral amino acid residues with positively charged amino acid residues (R,K);
  (vi) replacing small amino acid residues inside the protein with bulkier amino acid residues (W);
  (vii) comparing by homology alignment and/or homology modelling according to step (c)(i) at least two related parent proteases and transferring amino acid residue differences inbetween these protease backbones, preferably from a backbone having the improved property to a backbone not having this improved property;

(d) preparing a DNA sequence encoding the parent protease but for inclusion of a DNA codon of the at least one amino acid substitution proposed in steps (c)(ii)-(c)(vii), or subjecting the parent DNA sequence to random mutagenesis, targeting at least one of the regions identified in step (c)(i);

(e) expressing the DNA sequence obtained in step (d) in a host cell, and (h) selecting a host cell expressing a protease variant with an improved property.

The invention furthermore relates to a method for producing a protease variant obtainable or obtained by the method of generating protease variants described above, comprising (a) cultivating the host cell to produce a supernatant comprising the variant; and (b) recovering the variant.

The invention also relates to isolated nucleic acid sequences comprising a nucleic acid sequence which encodes the protease variant obtainable according to this method, as well as methods for producing it by (a) cultivating the host cell to produce a supernatant comprising the variant; and (b) recovering the variant; a transgenic plant, or plant part, capable of expressing it; transgenic, non-human animals, or products, or elements thereof, being capable of expressing it;

animal feeds, as well as animal feed additives, comprising it; methods for improving the nutritional value of an animal feed by use thereof; methods for the treatment of proteins, such as vegetable proteins, by use thereof; as well as the use thereof (i) in animal feed; (ii) in the preparation of animal feed; (iii) for improving the nutritional value of animal feed; and/or (iv) for the treatment of proteins; and/or in detergents.

Alternative Embodiments

In an alternative embodiment, the term "alteration" is used instead of "substitution" as the general term for amendments in the protease molecule. This alternative embodiment includes each of the claims formulated as exemplified below for claim 1, and also specifically includes everything what is stated herein, e.g., definitions (other than the definition of substitution), i.e., the various aspects, particular embodiments etc.

A variant of a parent protease, comprising an alteration in at least one position of at least one region selected from the group of regions consisting of: 6-18; 22-28; 32-39; 42-58; 62-63; 66-76; 78-100; 103-106; 111-114; 118-131; 134-136; 139-141; 144-151; 155-156; 160-176; 179-181; and 184-188; wherein
 (a) the alteration(s) are independently
  (i) an insertion of an amino acid immediately downstream of the position,
  (ii) a deletion of the amino acid which occupies the position, and/or
  (iii) a substitution of the amino acid which occupies the position;
 (b) the variant has protease activity; and
 (c) each position corresponds to a position of SEQ ID NO: 2, preferably amino acids 1 to 188 thereof; and
 (d) the variant has a percentage of identity to SEQ ID NO: 2, preferably to amino acids 1 to 188 thereof, of at least 60%.

The term "polypeptide variant", "protein variant", "enzyme variant", "protease variant" or simply "variant" refers to a polypeptide of the invention comprising one or more alteration(s), such as substitution(s), insertion(s), deletion(s), and/or truncation(s) of one or more specific amino acid residue(s) in one or more specific position(s) in the polypeptide.

The term "parent polypeptide", "parent protein", "parent enzyme", "standard enzyme", "parent protease" or simply "parent" refers to the polypeptide on which the variant was based. This term also refers to the polypeptide with which a variant is compared and aligned.

The term "randomized library", "variant library", or simply "library" refers to a library of variant polypeptides. Diversity in the variant library can be generated via mutagenesis of the genes encoding the variants at the DNA triplet level, such that individual codons are variegated, e.g., by using primers of partially randomized sequence in a PCR reaction. Several techniques have been described, by which one can create a diverse combinatorial library by variegating several nucleotide positions in a gene and recombining them, for instance where these positions are too far apart to be covered by a single (spiked or doped) oligonucleotide primer. These techniques include the use of in vivo recombination of the individually diversified gene segments as described in WO 97/07205 on page 3, lines 8 to 29 (Novozymes A/S). They also include the use of DNA shuffling techniques to create a library of full length genes, wherein several gene segments are combined, and wherein each segment may be diversified, e.g., by spiked mutagenesis (Stemmer, 1994, *Nature* 370: 389-391 and U.S. Pat. Nos. 5,811,238; 5,605,793; and 5,830, 721). One can use a gene encoding a protein "backbone" (wildtype parent polypeptide) as a template polynucleotide, and combine this with one or more single or double-stranded oligonucleotides as described in WO 98/41623 and in WO 98/41622 (Novozymes A/S). The single-stranded oligonucleotides could be partially randomized during synthesis. The double-stranded oligonucleotides could be PCR products incorporating diversity in a specific region. In both cases, one can dilute the diversity with corresponding segments encoding the sequence of the backbone protein in order to limit the average number of changes that are introduced.

Methods have also been established for designing the ratios of nucleotide mixtures (A; C; T; G) to be inserted in specific codon positions during oligo- or polynucleotide synthesis, so as to introduce a bias in order to approximate a desired frequency distribution towards a set of one or more desired amino acids that will be encoded by the particular codons. It may be of interest to produce a variant library, that comprises permutations of a number of known amino acid modifications in different locations in the primary sequence of the polypeptide. These could be introduced post-translationally or by chemical modification sites, or they could be introduced through mutations in the encoding genes. The modifications by themselves may previously have been proven beneficial for one reason or another (e.g., decreasing antigenicity, or improving specific activity, performance, stability, or other characteristics). In such instances, it may be desirable first to create a library of diverse combinations of known sequences. For example, if twelve individual mutations are known, one could combine (at least) twelve segments of the parent protein encoding gene, wherein each segment is present in two forms: one with, and one without the desired mutation. By varying the relative amounts of those segments, one could design a library (of size 2^12) for which the average number of mutations per gene can be predicted. This can be a useful way of combining mutations, that by themselves give some, but not sufficient effect, without resorting to very large libraries, as is often the case when using 'spiked mutagenesis'. Another way to combine these 'known mutations' could be by using family shuffling of oligomeric DNA encoding the known mutations with fragments of the full length wild type sequence.

In describing the various variants produced or contemplated according to the invention, a number of nomenclatures and conventions are used which are described in detail below. A frame of reference is first defined by aligning the variant polypeptide with a parent enzyme. A preferred parent enzyme is Protease 10 (amino acids 1 to 188 of SEQ ID NO: 2). Thereby a number of alterations will be defined in relation to the amino acid sequence of amino acids 1 to 188 of SEQ ID NO: 2.

A substitution in a variant is indicated as:
Original amino acid-position-substituted amino acid;
The three or one letter codes are used, including the codes Xaa and X to indicate any amino acid residue. Accordingly, the notation "T82S" or "Thr82Ser" means, that the variant comprises a substitution of threonine with serine in the variant amino acid position corresponding to the amino acid in position 82 in the parent enzyme, when the two are aligned as indicated above.

Where the original amino acid residue may be any amino acid residue, a short hand notation may at times be used indicating only the position, and the substituted amino acid, for example:
Position-substituted amino acid; or "82S",
Such a notation is particular relevant in connection with modification(s) in a series of homologous polypeptides.

Similarly when the identity of the substituting amino acid residue(s) is immaterial:

Original amino acid-position; or "T82"

When both the original amino acid(s) and substituted amino acid(s) may be any amino acid, then only the position is indicated, e.g., "82".

When the original amino acid(s) and/or substituted amino acid(s) may comprise more than one, but not all amino acid(s), then the amino acids are listed separated by commas:

Original amino acids-position no.-substituted amino acids; or "T10E,D,Y".

A number of examples of this nomenclature are listed below:

The substitution of threonine for histidine in position 91 is designated as: "His91Thr" or "H91T"; or the substitution of any amino acid residue acid for histidine in position 91 is designated as: "His91Xaa" or "H91X" or "His91" or "H91".

For a modification where the original amino acid(s) and/or substituted amino acid(s) may comprise more than one, but not all amino acid(s), the substitution of glutamic acid, aspartic acid, or tyrosine for threonine in position 10:

"Thr10Glu,Asp,Tyr" or "T10E,D,Y"; which indicates the specific variants: "T10E", "T10D", and "T10Y".

A deletion of glycine in position 26 will be indicated by: "Gly26*" or "G26*"

Correspondingly, the deletion of more than one amino acid residue, such as the deletion of glycine and glutamine in positions 26 and 27 will be designated "Gly26*+Gln27*" or "G26*+Q27*".

The insertion of an additional amino acid residue such as, e.g., a lysine after G26 is indicated by: "Gly26GlyLys" or "G26GK"; or, when more than one amino acid residue is inserted, such as, e.g., a Lys, and Ala after G26 this will be indicated as: "Gly26GlyLysAla" or "G26GKA".

In such cases the inserted amino acid residue(s) are numbered by the addition of lower case letters to the position number of the amino acid residue preceding the inserted amino acid residue(s). In the above example the sequences would thus be:

| Parent: | | Variant: | |
|---|---|---|---|
| 26 | 26 | 26a | 26b |
| G | G | K | A |

In cases where an amino acid residue identical to the existing amino acid residue is inserted, it is clear that degeneracy in the nomenclature arises. If for example a glycine is inserted after the glycine in the above example this would be indicated by "G26GG".

Given that an alanine were present in position 25, the same actual change could just as well be indicated as "A25AG":

| | Parent: | | Variant: | | |
|---|---|---|---|---|---|
| Numbering I: | 25 | 26 | 25 | 26 | 26a |
| Sequence: | A | G | A | G | G |
| Numbering II: | | | 25 | 25a | 26 |

Such instances will be apparent to the skilled person, and the indication "G26GG" and corresponding indications for this type of insertions is thus meant to comprise such equivalent degenerate indications.

By analogy, if amino acid sequence segments are repeated in the parent polypeptide and/or in the variant, it will be apparent to the skilled person that equivalent degenerate indications are comprised, also when other alterations than insertions are listed such as deletions and/or substitutions. For instance, the deletion of two consecutive amino acids "AG" in the sequence "AGAG" from position 194-197, may be written as "A194*+G1956*" or "A196*+G197*":

| | Parent: | | | | Variant: | |
|---|---|---|---|---|---|---|
| Numbering I: | 194 | 195 | 196 | 197 | 194 | 195 |
| Sequence: | A | G | A | G | A | G |
| Numbering II: | | | | | 196 | 197 |

Variants comprising multiple modifications are separated by pluses, e.g.: "Arg170Tyr+Gly195Glu" or "R170Y+G195E", representing modifications in positions 170 and 195 substituting tyrosine and glutamic acid for arginine and glycine, respectively. Thus, "Tyr167Gly,Ala,Ser,Thr+Arg170Gly,Ala,Ser,Thr" designates the following variants: "Tyr167Gly+Arg170Gly", "Tyr167Gly+Arg170Ala", "Tyr167Gly+Arg170Ser", "Tyr167Gly+Arg170Thr", "Tyr167Ala+Arg170Gly", "Tyr167Ala+Arg170Ala", "Tyr167Ala+Arg170Ser", "Tyr167Ala+Arg 170Thr", "Tyr167Ser+Arg170Gly", "Tyr167Ser+Arg170Ala", "Tyr167Ser+Arg170Ser", "Tyr167Ser+Arg 170Thr", "Tyr167Thr+Arg170Gly", "Tyr167Thr+Arg170Ala", "Tyr167Thr+Arg170Ser", and "Tyr167Thr+Arg170Thr".

This nomenclature is particular relevant relating to modifications aimed at substituting, inserting or deleting amino acid residues having specific common properties, such modifications are referred to as conservative amino acid modification(s).

Various Embodiments

These are additional various embodiments of the invention:

The variant of any one of claims 1-16 and 18-20 which comprises at least one of the following substitutions: T10Y, A24S, V51T, E53Q, T82S, A86Q, T87S, 196A, G118N, S122R, N130S, L186I.

The variant of any one of claims 1-16 and 18-19 which comprises at least one of the following substitutions: R38T; Q42G,P; R49T,Q; Q54N,R; A89S,T; H91S,T; N92S; S99A,Q; A120T; E125Q; T129Y,Q; M131L; T135N; Y147F; N151S; R165S; T166V,F; F171Y; V179I,L; preferably at least one of the following substitutions: R38T; N92S; A120T; E125Q; M131L; T135N; Y147F; N151S; R165S; and/or F171Y.

The variant of any one of claims 1-19 which comprises at least one of the following substitutions: A25S, T44S, A62S, P95A, V100I, I114V, T176N, N180S, V184L, R185T.

The variant of any one of claims 1-20 which has amended properties, such as an improved thermostability and/or a higher or lower optimum temperature, such as a Tm of at least 83.1° C. as measured by DSC in 10 mM sodium phosphate, 50 mM sodium chloride, pH 7.0.

The variant of any one of claims 1-20 which derives from a strain of the genus *Nocardiopsis*, such as *Nocardiopsis alba, Nocardiopsis antarctica, Nocardiopsis prasina, Nocardiopsis composta, Nocardiopsis dassonvillei, Nocardiopsis exhalans, Nocardiopsis halophila, Nocardiopsis halotolerans, Nocardiopsis kunsanensis, Nocardiopsis listeri, Nocardiopsis lucentensis, Nocardiopsis metallicus, Nocardiopsis sp., Nocardiopsis synnemataformans, Nocardiopsis trehalosi, Nocardiopsis tropica, Nocardiopsis umidischolae,* or *Nocardiopsis xinjiangensis*, preferably *Nocardiopsis alba*

DSM 15647, *Nocardiopsis dassonvillei* NRRL 18133, *Nocardiopsis dassonvillei* subsp. *dassonvillei* DSM 43235, *Nocardiopsis prasina* DSM 15648, *Nocardiopsis prasina* DSM 15649, *Nocardiopsis* sp. NRRL 18262, most preferably *Nocardiopsis* sp. FERM P-18676.

A composition, such as an animal feed additive, comprising at least one protease variant of any one of claims 1-20, and
 (a) at least one fat soluble vitamin;
 (b) at least one water soluble vitamin; and/or
 (c) at least one trace mineral,
optionally further comprising at least one enzyme selected from the following group of enzymes: amylases, galactanases, alpha-galactosidases, xylanases, endoglucanases, endo-1,3(4)-beta-glucanases, phytases, phospholipases, and other proteases; if desired also comprising at least one amylase, and/or phospholipase.

The present invention is further described by the following examples which should not be construed as limiting the scope of the invention.

EXAMPLES

Example 1

Protease Assays pNA Assay
 pNA substrate: Suc-AAPF-pNA (Bachem L-1400).
 Temperature: Room temperature (25° C.)
 Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0, 11.0, and 12.0 with HCl or NaOH.
 20 microliters protease (diluted in 0.01% Triton X-100) is mixed with 100 microliters assay buffer. The assay is started by adding 100 microliters pNA substrate (50 mg dissolved in 1.0 ml DMSO and further diluted 45× with 0.01% Triton X-100). The increase in $OD_{405}$ is monitored as a measure of the protease activity.

Protazyme AK Assay
 Substrate: Protazyme AK tablet (cross-linked and dyed casein; from Megazyme)
 Temperature: controlled (assay temperature).
 Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 2.5, 3.0, 3.5, 4.0, 5.0, 6.0, 7.0, 8.0, 9.0, 10.0 and 11.0 with HCl or NaOH.
 A Protazyme AK tablet is suspended in 2.0 ml 0.01% Triton X-100 by gentle stirring. 500 microliters of this suspension and 500 microliters assay buffer are mixed in an Eppendorf tube and placed on ice. 20 microliters protease sample (diluted in 0.01% Triton X-100) is added. The assay is initiated by transferring the Eppendorf tube to an Eppendorf thermomixer, which is set to the assay temperature. The tube is incubated for 15 minutes on the Eppendorf thermomixer at its highest shaking rate (1400 rpm). The incubation is stopped by transferring the tube back to the ice bath. Then the tube is centrifuged in an icecold centrifuge for a few minutes and 200 microliters supernatant is transferred to a microtiter plate. $OD_{650}$ is read as a measure of protease activity. A buffer blind is included in the assay (instead of enzyme).

Example 2

Preparation and Testing of Protease Variants

Four protease variants comprising the amino acid sequence of amino acids 1 to 188 of SEQ ID NO: 2 (Protease 10) with the single substitutions N47D, T127R, N92K, and Q54R, respectively, were prepared as described below for variant N47D.

Site directed mutagenesis was carried out using the Megaprimer method as described by Sarkar and Sommer (*Bio Techniques* 8: 404-407 (1990)).

The N47D variant was constructed by use of the following primers, of which primer R10WT-CL29 (SEQ ID NO: 11) is gene specific, and primer RSWT126 (SEQ ID NO: 12) mutagenic:

```
R10WT-CL29:
                             (SEQ ID NO: 11)
5' CCGATTATGGAGCGGATTGAACATGCG 3'

RSWT126:
                             (SEQ ID NO: 12)
5' GTGACCATCGGCGACGGCAGGGGCGTCTTCG 3',
``` to amplify by PCR an approximately 469 bp DNA fragment from the construct described below.

The Protease 10 DNA construct used for the above amplification was an expression cassette (SEQ ID NO: 13) for incorporation into the genome of *Bacillus subtilis*. The construct contains a fusion of DNA encoding the signal sequence and the gene encoding the pro- and the mature protein of Protease 10 (SEQ ID NO: 14), a promoter construction, and also the cat gene conferring resistance towards chloramphenicol. To facilitate the integration into the genome by homologous recombination, flanking regions of around 3 kb of a *Bacillus subtilis* endogenous gene were incorporated upstream and downstream of the Protease 10 encoding sequence.

The resulting 469 bp fragment was purified from an agarose gel (Sigma Aldrich cat. no. A6877) and used as a Megaprimer together with primer R10WT-CL39N (SEQ ID NO: 15) in a second PCR carried out on the same template.

```
R10WT-CL39N:
                             (SEQ ID NO: 15)
5' GGAGCTCTGAAAAAAAGGAGAGGATAAAGAATGAA 3'.
```

The full construction of approximately 10 kb is made in vitro by long range PCR, using the oligonucleotides R10WT-CL28N (SEQ ID NO: 16), R10WT-CL28C (SEQ ID NO: 17), and the Expand Long Template PCR System from Roche Applied Science (cat no. 11759060), according to the suppliers manual.

```
R10WT-CL28N:
                             (SEQ ID NO: 16)
5' GCGTTCCGATAATCGCGGTGACAATGCCG 3'

R10WT-CL28C:
                             (SEQ ID NO: 17)
5' TTCATGAGTCTGCGCCCTGAGATCCTCTG 3'
```

The resulting approximately 1.2 kb fragment was purified and combined in a new PCR reaction using Expand Long Template PCR System with the flanking fragments of the construction made by two PCR reactions using R10WT-2C-rev (SEQ ID NO: 18) and R10WT-CL28C (SEQ ID NO: 17); and RSWT001 (SEQ ID NO: 19) and R10WT-CL28N (SEQ ID NO: 16) as primer sets. The resulting 10 kb fragment can be amplified using the R10WT-CL28N (SEQ ID NO: 16) and R10WT-CL28C (SEQ ID NO: 17) primers, to increase the number of transformants.

```
R10WT-2C-rev:
                                            (SEQ ID NO: 18)
5' TAATCGCATGTTCAATCCGCTCCATAATCG 3'

RSWT001:
                                            (SEQ ID NO: 19)
5' CCCAACGGTTTCTTCATTCTTTATCCTCTCCTTTTTTTCAGAGC 3'
```

Competent cells of an amylase- and protease-low strain of *Bacillus subtilis* (such as strain SHA273 described in WO 92/11357 and WO 95/10603) were transformed with the respective resulting PCR fragments, and chlorampenicol resistant transformants were selected and checked by DNA sequencing to verify the presence of the correct mutation on the genome.

Cells of *Bacillus subtilis* harboring constructs encoding Protease 10 and each of the four variants thereof were used to incubate shakeflasks containing a rich media (PS-1: 100 g/L Sucrose (Danisco cat. no. 109-0429), 40 g/L crust soy, 10 g/L $Na_2HPO_4.12H_2O$ (Merck cat. no. 6579), 0.1 ml/L Pluronic PE 6100 (BASF 102-3098)), and cultivation took place for five days at 30° C. under vigorous shaking.

After cultivation, the supernatants were diluted four times in a 0.2 M $Na_2HPO_4$ buffer, titrated with a 0.1 M citric acid to either pH 4.0 or pH 6.0, and split in two. One half was incubated for four hours at 65° C. at the respective pH, after which it was frozen. The other half was frozen immediately and served as the control.

Prior to measuring the residual protease activity, the samples were diluted ten times in 50 mM CHES-HEPES buffer, pH 8.5. The activity was determined using a modified version of the Protazyme AK assay of Example 1, solubilising one tablet of the substrate in 4 ml CHES-HEPES buffer, pH 8.5, mixing under continuous agitation one ml of this substrate solution with 20 ul of diluted protease sample, which was then incubated at 37° C. The substrate should have the correct temperature prior to adding protease. After 15 minutes the reaction was stopped by adding 100 ul 1 M NaOH and the insoluble substrate was precipitated by centrifugation at 15000 rpm for 3 minutes after which the absorbance at 650 nm was measured. The values should be below OD 3.0, alternatively the protease sample should be diluted more than ten times prior to the activity measurement.

The relative residual activity (%) is calculated by dividing the activity after incubation at 65° C. with the activity of the corresponding control. The results of Table 1 below show that all four variants are of an improved thermostability as compared to Protease 10.

TABLE 1

Residual activity after incubation for four hours at 65° C.

| Protease | % Residual Actitivty pH 6 | % Residual Activity pH 4 |
|---|---|---|
| Protease 10 + N47D | 44 | 68 |
| Protease 10 + T127R | — | 77 |
| Protease 10 + N92K | — | 55 |
| Protease 10 + Q54R | 52 | 67 |
| Protease 10 | 19 | 41 |

Example 3

Protease Variant 22

A protease variant designated "Protease 22" and comprising a number of substitutions in thirteen of the seventeen regions specified in claim 1 was designed. This variant comprises the following substitutions as compared to the mature part of Protease 10 (amino acids 1-188 of SEQ ID NO: 2): T10Y, A25S, R38T, Q42P, T44S, R49K, Q54R, V56I, A62S, T82S, S99A, G118Ns, S120T, S122R, E125Q, T129Y, N130S, M131L, R165S, T166A, F171Y, T176N, V179L, N180S, V184L, and R185T.

The mature part of Protease 22 is amino acids 1-196 of SEQ ID NO: 21. The DNA sequence corresponding to SEQ ID NO: 21 is SEQ ID NO: 20.

The DNA sequence of SEQ ID NO: 20 was constructed and introduced into a *Bacillus* host for expression. The expressed protease was purified and characterized as an alpha-lytic protease (peptidase family 51 E and/or S2A).

The temperature-activity relationship of Protease 22 was measured at pH 9, using the Protazyme AK assay of Example 1, Protease 10 being included for comparative purposes. The results are shown in Table 2 below.

TABLE 2

Temperature profile at pH 9 of Protease 22 and Protease 10

| Temperature | Relative activity at pH 9 | |
|---|---|---|
| (° C.) | Protease 22 | Protease 10 |
| 15 | 0.016 | 0.015 |
| 25 | 0.010 | 0.024 |
| 37 | 0.028 | 0.068 |
| 50 | 0.069 | 0.199 |
| 60 | 0.138 | 0.510 |
| 70 | 0.474 | 1.000 |
| 80 | 1.000 | 0.394 |
| 90 | 0.375 | — |

From these results it appears that Protease 22 has a higher temperature optimum at pH 9 than the Protease 10, viz. around 80° C. as compared to around 70° C.

Differential Scanning calorimetry (DSC) was used to determine temperature stability at pH 7.0 of Protease 22 and Protease 10. The purified proteases were dialysed over night at 4° C. against 10 mM sodium phosphate, 50 mM sodium chloride, pH 7.0 and run on a VP-DSC instrument (Micro Cal) with a constant scan rate of 1.5° C./min from 20 to 100° C. Data-handling was performed using the MicroCal Origin software.

The resulting denaturation or melting temperatures, Tm's, were: For Protease 22: 83.5° C.; for Protease 10: 76.5° C.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A variant of a parent protease, comprising a substitution selected from the group consisting of:
6C; 7P; 8C; 9C; 10E,D; 12E,D; 13E,D,P; 16C; 17C; 18C; 23P; 24K,P,R; 25K,P,R; 27P; 32C; 33C; 37C; 39R,K; 42E,D; 43W; 46D,E; 47D,E; 52C; 55C; 56R,K; 58E,D; 62C; 63C; 67C; 69D,E; 70D,E; 71C; 72K,R; 76C; 81D,E,P; 82D,E,P; 84D,E; 85C; 89C,D,E; 92P,R; 93P; 94C,P; 95E,D; 96E,D,P; 97R,K; 98P; 99R,K; 103C; 105C,P; 106C; 111R,K; 113E,D; 118R,K; 120E,D; 122K; 124R,K; 125P; 127K; 129E,D; 130E,D; 134C; 135P; 136P; 139C; 140E,D; 141C; 144C; 145C; 146C; 147W; 148C; 149C; 150E,D; 151P,E,D; 155C; 156C; 160D,E; 161D,E; 162K,R; 163C; 166D,E; 170C; 172C; 173C; 174P; 175P; 176P; 180R,K; 181R,K; 184P; 187P; and 188R,K
wherein
(a) the variant has protease activity;
(b) each position corresponds to a position of amino acids 1 to 188 of SEQ ID NO: 2; and
(c) the variant has a sequence identity to amino acids 1 to 188 of SEQ ID NO: 2 of at least 90%.

2. The variant of claim 1, which has a sequence identity to amino acids 1 to 188 of SEQ ID NO: 2 of at least 95%.

3. The variant of claim 1, which comprises a substitution selected from the group consisting of 6C; 7P; 8C; 9C; 10E,D; 12E,D; 13E,D,P; 16C; 17C; 18C; 23P; 24K,P,R; 25K,P,R; 27P; 32C; 33C; 37C; 39R,K; and 42E,D.

4. The variant of claim 1, which comprises a substitution selected from the group consisting of 43W; 46D,E; 47D,E; 52C; 55C; 56R,K; 58E,D; 62C; 63C; 67C; 69D,E; 70D,E; 71O; 72K,R; 76C; 81D,E,P; 82D,E,P; 84D,E; and 85C.

5. The variant of claim 1, which comprises 89C,D,E; 92P,R; 93P; 94C,P; 95E,D; 96E,D,P; 97R,K; 98P; 99R,K; 103C; 105C,P; 106C; 111R,K; 113E,D; 118R,K; 120E,D; 122K; 124R,K; and 125P.

6. The variant of claim 1, which comprises a substitution selected from the group consisting of 127K; 129E,D; 130E,D; 134C; 135P; 136P; 139C; 140E,D; 141C; 144C; 145C; 146C; 147W; 148C; and 149C.

7. The variant of claim 1, which comprises a substitution selected from the group consisting of 150E,D; 151P,E,D; 155C; 156C; 160D,E; 161D,E; 162K,R; 163C; 166D,E; 170C; 172C; 173C; 174P; 175P; 176P; 180R,K; 181R,K; 184P; 187P; and 188R,K.

8. An animal feed additive comprising at least one variant of claim 1, and
(a) at least one fat soluble vitamin;
(b) at least one water soluble vitamin; and/or
(c) at least one trace mineral.

9. An animal feed additive comprising at least one variant of claim 2, and
(a) at least one fat soluble vitamin;
(b) at least one water soluble vitamin; and/or
(c) at least one trace mineral.

10. An animal feed additive comprising at least one variant of claim 3, and
(a) at least one fat soluble vitamin;
(b) at least one water soluble vitamin; and/or
(c) at least one trace mineral.

11. An animal feed additive comprising at least one variant of claim 4, and
(a) at least one fat soluble vitamin;
(b) at least one water soluble vitamin; and/or
(c) at least one trace mineral.

12. An animal feed additive comprising at least one variant of claim 5, and
(a) at least one fat soluble vitamin;
(b) at least one water soluble vitamin; and/or
(c) at least one trace mineral.

13. An animal feed additive comprising at least one variant of claim 6, and
(a) at least one fat soluble vitamin;
(b) at least one water soluble vitamin; and/or
(c) at least one trace mineral.

14. An animal feed additive comprising at least one variant of claim 7, and
(a) at least one fat soluble vitamin;
(b) at least one water soluble vitamin; and/or
(c) at least one trace mineral.

15. An animal feed composition having a crude protein content of 50 to 800 g/kg and comprising a variant of claim 1.

16. An animal feed composition having a crude protein content of 50 to 800 g/kg and comprising a variant of claim 2.

17. A method for improving the nutritional value of an animal feed, comprising adding a variant of claim 1 to the feed.

18. A method for improving the nutritional value of an animal feed, comprising adding a variant of claim 2 to the feed.

19. A method for the treatment of proteins, comprising adding a variant of claim 1 to at least one protein or protein source.

20. A method for the treatment of proteins, comprising adding a variant of claim 2 to at least one protein or protein source.

* * * * *

UNITED STATES PATENT AND TRADEMARK OFFICE
CERTIFICATE OF CORRECTION

| | | |
|---|---|---|
| PATENT NO. | : 8,772,011 B2 | Page 1 of 1 |
| APPLICATION NO. | : 13/738490 | |
| DATED | : July 8, 2014 | |
| INVENTOR(S) | : De Maria et al. | |

It is certified that error appears in the above-identified patent and that said Letters Patent is hereby corrected as shown below:

On the Title page, in the first line of the "Foreign Patent Documents" section, delete "DE   2004328" and replace with --DD          2004328--.

In the Claims
In column 79, line 55 (claim 4, line 3), delete "710" and insert --71C--.

Signed and Sealed this
Eleventh Day of November, 2014

Michelle K. Lee
*Deputy Director of the United States Patent and Trademark Office*

SEQUENCE LISTING

<160> NUMBER OF SEQ ID NOS: 21

<210> SEQ ID NO 1
<211> LENGTH: 1596
<212> TYPE: DNA
<213> ORGANISM: Nocardiopsis sp. NRRL 18262
<220> FEATURE:
<221> NAME/KEY: CDS
<222> LOCATION: (318)..(1463)
<220> FEATURE:
<221> NAME/KEY: sig_peptide
<222> LOCATION: (318)..(404)
<220> FEATURE:
<221> NAME/KEY: mat_peptide
<222> LOCATION: (900)..(1463)

<400> SEQUENCE: 1

```
acgtttggta cgggtaccgg tgtccgcatg tggccagaat gcccccttgc gacagggaac    60
ggattcggtc ggtagcgcat cgactccgac aaccgcgagg tggccgttcg cgtcgccacg   120
ttctgcgacc gtcatgcgac ccatcatcgg gtgaccccac cgagctctga atggtccacc   180
gttctgacgg tctttccctc accaaaacgt gcacctatgg ttaggacgtt gtttaccgaa   240
tgtctcggtg aacgacaggg gccggacggt attcggcccc gatccccgt tgatccccc     300 aggagagtag ggacccc atg cga ccc tcc ccc gtt gtc tcc gcc atc  ggt      350
                   Met Arg Pro Ser Pro Val Val Ser Ala Ile  Gly
                              -190                -185 acg gga gcg ctg  gcc ttc ggt ctg gcg  ctg tcc ggt acc ccg  ggt       395
Thr Gly Ala Leu  Ala Phe Gly Leu Ala  Leu Ser Gly Thr Pro  Gly
             -180               -175                -170 gcc ctc gcg gcc  acc gga gcg ctc ccc  cag tca ccc acc ccg  gag       440
Ala Leu Ala Ala  Thr Gly Ala Leu Pro  Gln Ser Pro Thr Pro  Glu
             -165               -160                -155 gcc gac gcg gtc  tcc atg cag gag gcg  ctc cag cgc gac ctc  gac       485
Ala Asp Ala Val  Ser Met Gln Glu Ala  Leu Gln Arg Asp Leu  Asp
             -150               -145                -140 ctg acc tcc gcc  gag gcc gag gag ctg  ctg gcc gcc cag gac  acc       530
Leu Thr Ser Ala  Glu Ala Glu Glu Leu  Leu Ala Ala Gln Asp  Thr
             -135               -130                -125 gcc ttc gag gtc  gac gag gcc gcg gcc  gag gcc gcc ggg gac  gcc       575
Ala Phe Glu Val  Asp Glu Ala Ala Ala  Glu Ala Ala Gly Asp  Ala
             -120               -115                -110 tac ggc ggc tcc  gtc ttc gac acc gag  agc ctg gaa ctg acc gtc ctg    623
Tyr Gly Gly Ser  Val Phe Asp Thr Glu  Ser Leu Glu Leu Thr Val Leu
             -105               -100                -95 gtc acc gat gcc gcc gcg gtc gag gcc gtg gag gcc acc ggc gcc ggg      671
Val Thr Asp Ala Ala Ala Val Glu Ala Val Glu Ala Thr Gly Ala Gly
         -90                -85                 -80 acc gag ctg gtc tcc tac ggc atc gac ggt ctc gac gag atc gtc cag      719
Thr Glu Leu Val Ser Tyr Gly Ile Asp Gly Leu Asp Glu Ile Val Gln
         -75                -70                 -65 gag ctc aac gcc gcc gac gcc gtt ccc ggt gtg gtc ggc tgg tac ccg      767
Glu Leu Asn Ala Ala Asp Ala Val Pro Gly Val Val Gly Trp Tyr Pro
-60                 -55                -50                  -45 gac gtg gcg ggt gac acc gtc gtc ctg gag gtc ctg gag ggt tcc gga      815
Asp Val Ala Gly Asp Thr Val Val Leu Glu Val Leu Glu Gly Ser Gly
             -40                -35                 -30 gcc gac gtc agc ggc ctg ctc gcg gac gcc ggc gtg gac gcc tcg gcc      863
Ala Asp Val Ser Gly Leu Leu Ala Asp Ala Gly Val Asp Ala Ser Ala
             -25                -20                 -15 gtc gag gtg acc acg agc gac cag ccc gag ctc tac gcc gac atc atc      911
Val Glu Val Thr Thr Ser Asp Gln Pro Glu Leu Tyr Ala Asp Ile Ile
```

```
                -10             -5              -1  1
ggt ggt ctg gcc tac acc atg ggc ggc cgc tgt tcg gtc ggc ttc gcg    959
Gly Gly Leu Ala Tyr Thr Met Gly Gly Arg Cys Ser Val Gly Phe Ala
 5              10              15              20 gcc acc aac gcc gcc ggt cag ccc ggg ttc gtc acc gcc ggt cac tgc   1007
Ala Thr Asn Ala Ala Gly Gln Pro Gly Phe Val Thr Ala Gly His Cys
                25              30              35 ggc cgc gtg ggc acc cag gtg acc atc ggc aac ggc agg ggc gtc ttc   1055
Gly Arg Val Gly Thr Gln Val Thr Ile Gly Asn Gly Arg Gly Val Phe
            40              45              50 gag cag tcc gtc ttc ccc ggc aac gac gcg gcc ttc gtc cgc ggt acg   1103
Glu Gln Ser Val Phe Pro Gly Asn Asp Ala Ala Phe Val Arg Gly Thr
        55              60              65 tcc aac ttc acg ctg acc aac ctg gtc agc cgc tac aac acc ggc ggg   1151
Ser Asn Phe Thr Leu Thr Asn Leu Val Ser Arg Tyr Asn Thr Gly Gly
    70              75              80 tac gcc acg gtc gcc ggt cac aac cag gcc ccc atc ggc tcc tcc gtc   1199
Tyr Ala Thr Val Ala Gly His Asn Gln Ala Pro Ile Gly Ser Ser Val
85              90              95              100 tgc cgc tcc ggc tcc acc acc ggt tgg cac tgc ggc acc atc cag gcc   1247
Cys Arg Ser Gly Ser Thr Thr Gly Trp His Cys Gly Thr Ile Gln Ala
            105             110             115 cgc ggc cag tcg gtg agc tac ccc gag ggc acc gtc acc aac atg acc   1295
Arg Gly Gln Ser Val Ser Tyr Pro Glu Gly Thr Val Thr Asn Met Thr
        120             125             130 cgg acc acc gtg tgc gcc gag ccc ggc gac tcc ggc ggc tcc tac atc   1343
Arg Thr Thr Val Cys Ala Glu Pro Gly Asp Ser Gly Gly Ser Tyr Ile
    135             140             145 tcc ggc acc cag gcc cag ggc gtg acc tcc ggc ggc tcc ggc aac tgc   1391
Ser Gly Thr Gln Ala Gln Gly Val Thr Ser Gly Gly Ser Gly Asn Cys
150             155             160 cgc acc ggc ggg acc acc ttc tac cag gag gtc acc ccc atg gtg aac   1439
Arg Thr Gly Gly Thr Thr Phe Tyr Gln Glu Val Thr Pro Met Val Asn
165             170             175             180 tcc tgg ggc gtc cgt ctc cgg acc tgatccccgc ggttccaggc ggaccgacgg   1493
Ser Trp Gly Val Arg Leu Arg Thr
                185 tcgtgacctg agtaccaggc gtccccgccg cttccagcgg cgtccgcacc ggggtgggac   1553 cgggcgtggc cacggcccca cccgtgaccg gaccgcccgg cta                     1596

<210> SEQ ID NO 2
<211> LENGTH: 382
<212> TYPE: PRT
<213> ORGANISM: Nocardiopsis sp. NRRL 18262

<400> SEQUENCE: 2

Met Arg Pro Ser Pro  Val Val Ser Ala Ile  Gly Thr Gly Ala Leu
                -190             -185               -180

Ala Phe Gly Leu Ala  Leu Ser Gly Thr Pro  Gly Ala Leu Ala Ala
                -175             -170               -165

Thr Gly Ala Leu Pro  Gln Ser Pro Thr Pro  Glu Ala Asp Ala Val
                -160             -155               -150

Ser Met Gln Glu Ala  Leu Gln Arg Asp Leu  Asp Leu Thr Ser Ala
                -145             -140               -135

Glu Ala Glu Glu Leu  Leu Ala Ala Gln Asp  Thr Ala Phe Glu Val
                -130             -125               -120

Asp Glu Ala Ala Ala  Glu Ala Ala Gly Asp  Ala Tyr Gly Gly Ser
                -115             -110               -105
```

-continued

```
Val Phe Asp Thr Glu  Ser Leu Glu Leu Thr Val Leu Val Thr Asp Ala
            -100              -95              -90

Ala Ala Val Glu Ala Val Glu Ala Thr Gly Ala Gly Thr Glu Leu Val
        -85              -80              -75

Ser Tyr Gly Ile Asp Gly Leu Asp Glu Ile Val Gln Glu Leu Asn Ala
        -70              -65              -60

Ala Asp Ala Val Pro Gly Val Gly Trp Tyr Pro Asp Val Ala Gly
        -55              -50              -45

Asp Thr Val Val Leu Glu Val Leu Glu Gly Ser Gly Ala Asp Val Ser
-40              -35              -30              -25

Gly Leu Leu Ala Asp Ala Gly Val Asp Ala Ser Ala Val Glu Val Thr
                -20              -15              -10

Thr Ser Asp Gln Pro Glu Leu Tyr Ala Asp Ile Ile Gly Gly Leu Ala
             -5              -1  1               5

Tyr Thr Met Gly Gly Arg Cys Ser Val Gly Phe Ala Ala Thr Asn Ala
            10              15              20

Ala Gly Gln Pro Gly Phe Val Thr Ala Gly His Cys Gly Arg Val Gly
25              30              35              40

Thr Gln Val Thr Ile Gly Asn Gly Arg Gly Val Phe Glu Gln Ser Val
                45              50              55

Phe Pro Gly Asn Asp Ala Ala Phe Val Arg Gly Thr Ser Asn Phe Thr
            60              65              70

Leu Thr Asn Leu Val Ser Arg Tyr Asn Thr Gly Gly Tyr Ala Thr Val
            75              80              85

Ala Gly His Asn Gln Ala Pro Ile Gly Ser Ser Val Cys Arg Ser Gly
            90              95              100

Ser Thr Thr Gly Trp His Cys Gly Thr Ile Gln Ala Arg Gly Gln Ser
105             110             115             120

Val Ser Tyr Pro Glu Gly Thr Val Thr Asn Met Thr Arg Thr Thr Val
                125             130             135

Cys Ala Glu Pro Gly Asp Ser Gly Gly Ser Tyr Ile Ser Gly Thr Gln
            140             145             150

Ala Gln Gly Val Thr Ser Gly Gly Ser Gly Asn Cys Arg Thr Gly Gly
            155             160             165

Thr Thr Phe Tyr Gln Glu Val Thr Pro Met Val Asn Ser Trp Gly Val
            170             175             180

Arg Leu Arg Thr
185
```

<210> SEQ ID NO 3
<211> LENGTH: 1065
<212> TYPE: DNA
<213> ORGANISM: Nocardiopsis dassonvillei subspecies dassonvillei DSM 43235
<220> FEATURE:
<221> NAME/KEY: CDS
<222> LOCATION: (1)..(1062)
<220> FEATURE:
<221> NAME/KEY: mat_peptide
<222> LOCATION: (499)..(1062)

<400> SEQUENCE: 3

```
gct ccg gcc ccc gtc ccc cag acc ccc gtc gcc gac gac agc gcc      45
Ala Pro Ala Pro Val Pro Gln Thr Pro Val Ala Asp Asp Ser Ala
    -165             -160             -155 gcc agc atg acc gag gcg ctc aag cgc gac ctc gac ctc acc tcg      90
Ala Ser Met Thr Glu Ala Leu Lys Arg Asp Leu Asp Leu Thr Ser
```

-continued

```
                    -150              -145              -140
gcc gag gcc gag gag ctt ctc tcg gcg cag gaa gcc gcc atc gag      135
Ala Glu Ala Glu Glu Leu Leu Ser Ala Gln Glu Ala Ala Ile Glu
        -135              -130              -125 acc gac gcc gag gcc acc gag gcc gcg ggc gag gcc tac ggc ggc      180
Thr Asp Ala Glu Ala Thr Glu Ala Ala Gly Glu Ala Tyr Gly Gly
        -120              -115              -110 tca ctg ttc gac acc gag acc ctc gaa ctc acc gtg ctg gtc acc gac  228
Ser Leu Phe Asp Thr Glu Thr Leu Glu Leu Thr Val Leu Val Thr Asp
        -105              -100              -95 gcc tcc gcc gtc gag gcg gtc gag gcc acc gga gcc cag gcc acc gtc  276
Ala Ser Ala Val Glu Ala Val Glu Ala Thr Gly Ala Gln Ala Thr Val
-90              -85               -80               -75 gtc tcc cac ggc acc gag ggc ctg acc gag gtc gtg gag gac ctc aac  324
Val Ser His Gly Thr Glu Gly Leu Thr Glu Val Val Glu Asp Leu Asn
            -70              -65               -60 ggc gcc gag gtt ccc gag agc gtc ctc ggc tgg tac ccg gac gtg gag  372
Gly Ala Glu Val Pro Glu Ser Val Leu Gly Trp Tyr Pro Asp Val Glu
        -55               -50               -45 agc gac acc gtc gtg gtc gag gtg ctg gag ggc tcc gac gcc gac gtc  420
Ser Asp Thr Val Val Val Glu Val Leu Glu Gly Ser Asp Ala Asp Val
            -40              -35               -30 gcc gcc ctg ctc gcc gac gcc ggt gtg gac tcc tcg gtc cgg gtg      468
Ala Ala Leu Leu Ala Asp Ala Gly Val Asp Ser Ser Val Arg Val
        -25              -20               -15 gag gag gcc gag gag gcc ccg cag gtc tac gcc gac atc atc ggc ggc  516
Glu Glu Ala Glu Glu Ala Pro Gln Val Tyr Ala Asp Ile Ile Gly Gly
-10              -5               -1  1                5 ctg gcc tac tac atg ggc ggc cgc tgc tcc gtc ggc ttc gcc gcg acc  564
Leu Ala Tyr Tyr Met Gly Gly Arg Cys Ser Val Gly Phe Ala Ala Thr
                10               15               20 aac agc gcc ggt cag ccc ggt ttc gtc acc gcc ggc cac tgc ggc acc  612
Asn Ser Ala Gly Gln Pro Gly Phe Val Thr Ala Gly His Cys Gly Thr
            25               30               35 gtc ggc acc ggc gtg acc atc ggc aac ggc acc ggc acc ttc cag aac  660
Val Gly Thr Gly Val Thr Ile Gly Asn Gly Thr Gly Thr Phe Gln Asn
        40               45               50 tcg gtc ttc ccc ggc aac gac gcc gcc ttc gtc cgc ggc acc tcc aac  708
Ser Val Phe Pro Gly Asn Asp Ala Ala Phe Val Arg Gly Thr Ser Asn
55               60               65               70 ttc acc ctg acc aac ctg gtc tcg cgc tac aac tcc ggc ggc tac cag  756
Phe Thr Leu Thr Asn Leu Val Ser Arg Tyr Asn Ser Gly Gly Tyr Gln
            75               80               85 tcg gtg acc ggt acc agc cag gcc ccg gcc ggc tcg gcc gtg tgc cgc  804
Ser Val Thr Gly Thr Ser Gln Ala Pro Ala Gly Ser Ala Val Cys Arg
        90               95               100 tcc ggc tcc acc acc ggc tgg cac tgc ggc acc atc cag gcc cgc aac  852
Ser Gly Ser Thr Thr Gly Trp His Cys Gly Thr Ile Gln Ala Arg Asn
        105              110              115 cag acc gtg cgc tac ccg cag ggc acc gtc tac tcg ctc acc cgc acc  900
Gln Thr Val Arg Tyr Pro Gln Gly Thr Val Tyr Ser Leu Thr Arg Thr
        120              125              130 aac gtg tgc gcc gag ccc ggc gac tcc ggc ggt tcg ttc atc tcc ggc  948
Asn Val Cys Ala Glu Pro Gly Asp Ser Gly Gly Ser Phe Ile Ser Gly
135              140              145              150 tcg cag gcc cag ggc gtc acc tcc ggc ggc tcc ggc aac tgc tcc gtc  996
Ser Gln Ala Gln Gly Val Thr Ser Gly Gly Ser Gly Asn Cys Ser Val
            155              160              165 ggc ggc acg acc tac tac cag gag gtc acc ccg atg atc aac tcc tgg  1044
```

```
Gly Gly Thr Thr Tyr Tyr Gln Glu Val Thr Pro Met Ile Asn Ser Trp
            170                 175                 180 ggt gtc agg atc cgg acc taa                                                    1065
Gly Val Arg Ile Arg Thr
        185

<210> SEQ ID NO 4
<211> LENGTH: 354
<212> TYPE: PRT
<213> ORGANISM: Nocardiopsis dassonvillei subspecies dassonvillei DSM
      43235

<400> SEQUENCE: 4

Ala Pro  Ala Pro Val Pro Gln  Thr Pro Val Ala Asp  Asp Ser Ala
    -165             -160                 -155

Ala Ser  Met Thr Glu Ala Leu  Lys Arg Asp Leu Asp  Leu Thr Ser
    -150             -145                 -140

Ala Glu  Ala Glu Glu Leu Leu  Ser Ala Gln Glu Ala  Ala Ile Glu
    -135             -130                 -125

Thr Asp  Ala Glu Ala Thr Glu  Ala Ala Gly Glu Ala  Tyr Gly Gly
    -120             -115                 -110

Ser Leu  Phe Asp Thr Glu Thr  Leu Glu Leu Thr Val  Leu Val Thr Asp
    -105             -100                  -95

Ala Ser Ala Val Glu Ala Val Glu Ala Thr Gly Ala Gln Ala Thr Val
 -90             -85                  -80                  -75

Val Ser His Gly Thr Glu Gly Leu Thr Glu Val Val Glu Asp Leu Asn
                 -70                  -65                  -60

Gly Ala Glu Val Pro Glu Ser Val Leu Gly Trp Tyr Pro Asp Val Glu
                 -55                  -50                  -45

Ser Asp Thr Val Val Glu Val Leu Glu Gly Ser Asp Ala Asp Val
             -40                  -35                  -30

Ala Ala Leu Leu Ala Asp Ala Gly Val Asp Ser Ser Val Arg Val
         -25                  -20                  -15

Glu Glu Ala Glu Glu Ala Pro Gln Val Tyr Ala Asp Ile Ile Gly Gly
 -10              -5                   -1  1                   5

Leu Ala Tyr Tyr Met Gly Gly Arg Cys Ser Val Gly Phe Ala Ala Thr
                 10                  15                   20

Asn Ser Ala Gly Gln Pro Gly Phe Val Thr Ala Gly His Cys Gly Thr
             25                  30                   35

Val Gly Thr Gly Val Thr Ile Gly Asn Gly Thr Gly Thr Phe Gln Asn
     40                   45                   50

Ser Val Phe Pro Gly Asn Asp Ala Ala Phe Val Arg Gly Thr Ser Asn
55                   60                   65                   70

Phe Thr Leu Thr Asn Leu Val Ser Arg Tyr Asn Ser Gly Gly Tyr Gln
                 75                   80                   85

Ser Val Thr Gly Thr Ser Gln Ala Pro Ala Gly Ser Ala Val Cys Arg
             90                   95                  100

Ser Gly Ser Thr Thr Gly Trp His Cys Gly Thr Ile Gln Ala Arg Asn
            105                  110                  115

Gln Thr Val Arg Tyr Pro Gln Gly Thr Val Tyr Ser Leu Thr Arg Thr
        120                  125                  130

Asn Val Cys Ala Glu Pro Gly Asp Ser Gly Ser Phe Ile Ser Gly
135                  140                  145                  150

Ser Gln Ala Gln Gly Val Thr Ser Gly Gly Ser Gly Asn Cys Ser Val
                155                  160                  165
```

```
Gly Gly Thr Thr Tyr Tyr Gln Glu Val Thr Pro Met Ile Asn Ser Trp
            170                 175                 180

Gly Val Arg Ile Arg Thr
        185

<210> SEQ ID NO 5
<211> LENGTH: 1062
<212> TYPE: DNA
<213> ORGANISM: Nocardiopsis prasina DSM 15648
<220> FEATURE:
<221> NAME/KEY: CDS
<222> LOCATION: (1)..(1059)
<220> FEATURE:
<221> NAME/KEY: mat_peptide
<222> LOCATION: (496)..(1059)

<400> SEQUENCE: 5 gcc  acc  gga  ccg  ctc  ccc  cag  tca  ccc  acc  ccg  gag  gcc  gac  gcc         45
Ala  Thr  Gly  Pro  Leu  Pro  Gln  Ser  Pro  Thr  Pro  Glu  Ala  Asp  Ala
-165                -160                -155 gtc  tcc  atg  cag  gag  gcg  ctc  cag  cgc  gac  ctc  ggc  ctg  acc  ccg         90
Val  Ser  Met  Gln  Glu  Ala  Leu  Gln  Arg  Asp  Leu  Gly  Leu  Thr  Pro
-150                -145                -140 ctt  gag  gcc  gat  gaa  ctg  ctg  gcc  gcc  cag  gac  acc  gcc  ttc  gag        135
Leu  Glu  Ala  Asp  Glu  Leu  Leu  Ala  Ala  Gln  Asp  Thr  Ala  Phe  Glu
-135                -130                -125 gtc  gac  gag  gcc  gcg  gcc  gcg  gcc  gcc  ggg  gac  gcc  tac  ggc  ggc        180
Val  Asp  Glu  Ala  Ala  Ala  Ala  Ala  Ala  Gly  Asp  Ala  Tyr  Gly  Gly
-120                -115                -110 tcc  gtc  ttc  gac  acc  gag  acc  ctg  gaa  ctg  acc  gtc  ctg  gtc  acc  gac   228
Ser  Val  Phe  Asp  Thr  Glu  Thr  Leu  Glu  Leu  Thr  Val  Leu  Val  Thr  Asp
-105                -100                -95                 -90 gcc  gcc  tcg  gtc  gag  gct  gtg  gag  gcc  acc  ggc  gcg  ggt  acc  gaa  ctc   276
Ala  Ala  Ser  Val  Glu  Ala  Val  Glu  Ala  Thr  Gly  Ala  Gly  Thr  Glu  Leu
                    -85                 -80                 -75 gtc  tcc  tac  ggc  atc  gag  ggc  ctc  gac  gag  atc  atc  cag  gat  ctc  aac   324
Val  Ser  Tyr  Gly  Ile  Glu  Gly  Leu  Asp  Glu  Ile  Ile  Gln  Asp  Leu  Asn
                    -70                 -65                 -60 gcc  gcc  gac  gcc  gtc  ccc  ggc  gtg  gtc  ggc  tgg  tac  ccg  gac  gtg  gcg   372
Ala  Ala  Asp  Ala  Val  Pro  Gly  Val  Val  Gly  Trp  Tyr  Pro  Asp  Val  Ala
                    -55                 -50                 -45 ggt  gac  acc  gtc  gtc  ctg  gag  gtc  ctg  gag  ggt  tcc  gga  gcc  gac  gtg   420
Gly  Asp  Thr  Val  Val  Leu  Glu  Val  Leu  Glu  Gly  Ser  Gly  Ala  Asp  Val
                    -40                 -35                 -30 agc  ggc  ctg  ctc  gcc  gac  gcc  ggc  gtg  gac  gcc  tcg  gcc  gtc  gag  gtg   468
Ser  Gly  Leu  Leu  Ala  Asp  Ala  Gly  Val  Asp  Ala  Ser  Ala  Val  Glu  Val
-25                 -20                 -15                 -10 acc  agc  agt  gcg  cag  ccc  gag  ctc  tac  gcc  gac  atc  atc  ggc  ggt  ctg   516
Thr  Ser  Ser  Ala  Gln  Pro  Glu  Leu  Tyr  Ala  Asp  Ile  Ile  Gly  Gly  Leu
                    -5                  -1   1              5 gcc  tac  acc  atg  ggc  ggc  cgc  tgt  tcg  gtc  gga  ttc  gcg  gcc  acc  aac   564
Ala  Tyr  Thr  Met  Gly  Gly  Arg  Cys  Ser  Val  Gly  Phe  Ala  Ala  Thr  Asn
                    10                  15                  20 gcc  gcc  ggt  cag  ccc  gga  ttc  gtc  acc  gcc  ggt  cac  tgt  ggc  cgc  gtg   612
Ala  Ala  Gly  Gln  Pro  Gly  Phe  Val  Thr  Ala  Gly  His  Cys  Gly  Arg  Val
                    25                  30                  35 ggc  acc  cag  gtg  agc  atc  ggc  aac  ggc  cag  ggc  gtc  ttc  gag  cag  tcc   660
Gly  Thr  Gln  Val  Ser  Ile  Gly  Asn  Gly  Gln  Gly  Val  Phe  Glu  Gln  Ser
40                  45                  50                  55 atc  ttc  ccg  ggc  aac  gac  gcc  gcc  ttc  gtc  cgc  ggc  acg  tcc  aac  ttc   708
Ile  Phe  Pro  Gly  Asn  Asp  Ala  Ala  Phe  Val  Arg  Gly  Thr  Ser  Asn  Phe
                    60                  65                  70
```

```
acg ctg acc aac ctg gtc agc cgc tac aac acc ggt ggt tac gcc acc    756
Thr Leu Thr Asn Leu Val Ser Arg Tyr Asn Thr Gly Gly Tyr Ala Thr
        75                  80                  85 gtc gcc ggc cac aac cag gcg ccc atc ggc tcc tcc gtc tgc cgc tcc    804
Val Ala Gly His Asn Gln Ala Pro Ile Gly Ser Ser Val Cys Arg Ser
        90                  95                  100 ggc tcc acc acc ggc tgg cac tgc ggc acc atc cag gcc cgc ggc cag    852
Gly Ser Thr Thr Gly Trp His Cys Gly Thr Ile Gln Ala Arg Gly Gln
    105                 110                 115 tcg gtg agc tac ccc gag ggc acc gtc acc aac atg acc cgg acc acc    900
Ser Val Ser Tyr Pro Glu Gly Thr Val Thr Asn Met Thr Arg Thr Thr
120                 125                 130                 135 gtg tgc gcc gag ccc ggc gac tcc ggc ggc tcc tac atc tcc ggc aac    948
Val Cys Ala Glu Pro Gly Asp Ser Gly Gly Ser Tyr Ile Ser Gly Asn
                140                 145                 150 cag gcc cag ggc gtc acc tcc ggc ggc tcc ggc aac tgc cgc acc ggc    996
Gln Ala Gln Gly Val Thr Ser Gly Gly Ser Gly Asn Cys Arg Thr Gly
                155                 160                 165 ggg acc acc ttc tac cag gag gtc acc ccc atg gtg aac tcc tgg ggc   1044
Gly Thr Thr Phe Tyr Gln Glu Val Thr Pro Met Val Asn Ser Trp Gly
                170                 175                 180 gtc cgt ctc cgg acc taa                                            1062
Val Arg Leu Arg Thr
                185

<210> SEQ ID NO 6
<211> LENGTH: 353
<212> TYPE: PRT
<213> ORGANISM: Nocardiopsis prasina DSM 15648

<400> SEQUENCE: 6

Ala  Thr  Gly  Pro  Leu  Pro  Gln  Ser  Pro  Thr  Pro  Glu  Ala  Asp  Ala
-165                -160                -155

Val  Ser  Met  Gln  Glu  Ala  Leu  Gln  Arg  Asp  Leu  Gly  Leu  Thr  Pro
-150                -145                -140

Leu  Glu  Ala  Asp  Glu  Leu  Leu  Ala  Ala  Gln  Asp  Thr  Ala  Phe  Glu
-135                -130                -125

Val  Asp  Glu  Ala  Ala  Ala  Ala  Ala  Ala  Gly  Asp  Ala  Tyr  Gly  Gly
-120                -115                -110

Ser  Val  Phe  Asp  Thr  Glu  Thr  Leu  Glu  Leu  Thr  Val  Leu  Val  Thr  Asp
-105                -100                -95                 -90

Ala  Ala  Ser  Val  Glu  Ala  Val  Glu  Ala  Thr  Gly  Ala  Gly  Thr  Glu  Leu
                -85                 -80                 -75

Val  Ser  Tyr  Gly  Ile  Glu  Gly  Leu  Asp  Glu  Ile  Ile  Gln  Asp  Leu  Asn
                -70                 -65                 -60

Ala  Ala  Asp  Ala  Val  Pro  Gly  Val  Gly  Trp  Tyr  Pro  Asp  Val  Ala
                -55                 -50                 -45

Gly  Asp  Thr  Val  Val  Leu  Glu  Val  Leu  Glu  Gly  Ser  Gly  Ala  Asp  Val
                -40                 -35                 -30

Ser  Gly  Leu  Leu  Ala  Asp  Ala  Gly  Val  Asp  Ala  Ser  Ala  Val  Glu  Val
-25                 -20                 -15                 -10

Thr  Ser  Ser  Ala  Gln  Pro  Glu  Leu  Tyr  Ala  Asp  Ile  Ile  Gly  Gly  Leu
                -5                  -1  1                   5

Ala  Tyr  Thr  Met  Gly  Gly  Arg  Cys  Ser  Val  Gly  Phe  Ala  Ala  Thr  Asn
                10                  15                  20

Ala  Ala  Gly  Gln  Pro  Gly  Phe  Val  Thr  Ala  Gly  His  Cys  Gly  Arg  Val
                25                  30                  35
```

```
Gly Thr Gln Val Ser Ile Gly Asn Gly Gln Gly Val Phe Glu Gln Ser
 40                  45                  50                  55

Ile Phe Pro Gly Asn Asp Ala Ala Phe Val Arg Gly Thr Ser Asn Phe
                 60                  65                  70

Thr Leu Thr Asn Leu Val Ser Arg Tyr Asn Thr Gly Gly Tyr Ala Thr
             75                  80                  85

Val Ala Gly His Asn Gln Ala Pro Ile Gly Ser Ser Val Cys Arg Ser
         90                  95                 100

Gly Ser Thr Thr Gly Trp His Cys Gly Thr Ile Gln Ala Arg Gly Gln
    105                 110                 115

Ser Val Ser Tyr Pro Glu Gly Thr Val Thr Asn Met Thr Arg Thr Thr
120                 125                 130                 135

Val Cys Ala Glu Pro Gly Asp Ser Gly Gly Ser Tyr Ile Ser Gly Asn
                140                 145                 150

Gln Ala Gln Gly Val Thr Ser Gly Gly Ser Gly Asn Cys Arg Thr Gly
            155                 160                 165

Gly Thr Thr Phe Tyr Gln Glu Val Thr Pro Met Val Asn Ser Trp Gly
        170                 175                 180

Val Arg Leu Arg Thr
    185

<210> SEQ ID NO 7
<211> LENGTH: 1062
<212> TYPE: DNA
<213> ORGANISM: Nocardiopsis prasina DSM 15649
<220> FEATURE:
<221> NAME/KEY: CDS
<222> LOCATION: (1)..(1059)
<220> FEATURE:
<221> NAME/KEY: mat_peptide
<222> LOCATION: (496)..(1059)

<400> SEQUENCE: 7 gcc acc gga cca ctc ccc cag tca ccc acc ccg gag gcc gac gcc          45
Ala Thr Gly Pro Leu Pro Gln Ser Pro Thr Pro Glu Ala Asp Ala
-165                -160                -155 gtc tcc atg cag gag gcg ctc cag cgc gac ctc ggc ctg acc ccg          90
Val Ser Met Gln Glu Ala Leu Gln Arg Asp Leu Gly Leu Thr Pro
-150                -145                -140 ctt gag gcc gat gaa ctg ctg gcc gcc cag gac acc gcc ttc gag         135
Leu Glu Ala Asp Glu Leu Leu Ala Ala Gln Asp Thr Ala Phe Glu
-135                -130                -125 gtc gac gag gcc gcg gcc gag gcc gcc ggt gac gcc tac ggc ggc         180
Val Asp Glu Ala Ala Ala Glu Ala Ala Gly Asp Ala Tyr Gly Gly
-120                -115                -110 tcc gtc ttc gac acc gag acc ctg gaa ctg acc gtc ctg gtc acc gac    228
Ser Val Phe Asp Thr Glu Thr Leu Glu Leu Thr Val Leu Val Thr Asp
-105                -100                 -95                 -90 tcc gcc gcg gtc gag gcg gtg gag gcc acc ggc gcc ggg acc gaa ctg    276
Ser Ala Ala Val Glu Ala Val Glu Ala Thr Gly Ala Gly Thr Glu Leu
                 -85                 -80                 -75 gtc tcc tac ggc atc acg ggc ctc gac gag atc gtc gag gag ctc aac    324
Val Ser Tyr Gly Ile Thr Gly Leu Asp Glu Ile Val Glu Glu Leu Asn
             -70                 -65                 -60 gcc gcc gac gcc gtt ccc ggc gtg gtc ggc tgg tac ccg gac gtc gcg    372
Ala Ala Asp Ala Val Pro Gly Val Val Gly Trp Tyr Pro Asp Val Ala
         -55                 -50                 -45 ggt gac acc gtc gtg ctg gag gtc ctg gag ggt tcc ggc gcc gac gtg    420
Gly Asp Thr Val Val Leu Glu Val Leu Glu Gly Ser Gly Ala Asp Val
```

```
                -40             -35             -30
ggc ggc ctg ctc gcc gac gcc ggc gtg gac gcc tcg gcg gtc gag gtg      468
Gly Gly Leu Leu Ala Asp Ala Gly Val Asp Ala Ser Ala Val Glu Val
-25             -20             -15             -10 acc acc acc gag cag ccc gag ctg tac gcc gac atc atc ggc ggt ctg      516
Thr Thr Thr Glu Gln Pro Glu Leu Tyr Ala Asp Ile Ile Gly Gly Leu
            -5              -1  1               5 gcc tac acc atg ggc ggc cgc tgt tcg gtc ggc ttc gcg gcc acc aac      564
Ala Tyr Thr Met Gly Gly Arg Cys Ser Val Gly Phe Ala Ala Thr Asn
        10              15              20 gcc gcc ggt cag ccc ggg ttc gtc acc gcc ggt cac tgt ggc cgc gtg      612
Ala Ala Gly Gln Pro Gly Phe Val Thr Ala Gly His Cys Gly Arg Val
    25              30              35 ggc acc cag gtg acc atc ggc aac ggc cgg ggc gtc ttc gag cag tcc      660
Gly Thr Gln Val Thr Ile Gly Asn Gly Arg Gly Val Phe Glu Gln Ser
40              45              50              55 atc ttc ccg ggc aac gac gcc gcc ttc gtc cgc gga acg tcc aac ttc      708
Ile Phe Pro Gly Asn Asp Ala Ala Phe Val Arg Gly Thr Ser Asn Phe
                60              65              70 acg ctg acc aac ctg gtc agc cgc tac aac acc ggc ggc tac gcc acc      756
Thr Leu Thr Asn Leu Val Ser Arg Tyr Asn Thr Gly Gly Tyr Ala Thr
            75              80              85 gtc gcc ggt cac aac cag gcg ccc atc ggc tcc tcc gtc tgc cgc tcc      804
Val Ala Gly His Asn Gln Ala Pro Ile Gly Ser Ser Val Cys Arg Ser
        90              95              100 ggc tcc acc acc ggt tgg cac tgc ggc acc atc cag gcc cgc ggc cag      852
Gly Ser Thr Thr Gly Trp His Cys Gly Thr Ile Gln Ala Arg Gly Gln
    105             110             115 tcg gtg agc tac ccc gag ggc acc gtc acc aac atg acg cgg acc acc      900
Ser Val Ser Tyr Pro Glu Gly Thr Val Thr Asn Met Thr Arg Thr Thr
120             125             130             135 gtg tgc gcc gag ccc ggc gac tcc ggc ggc tcc tac atc tcc ggc aac      948
Val Cys Ala Glu Pro Gly Asp Ser Gly Gly Ser Tyr Ile Ser Gly Asn
                140             145             150 cag gcc cag ggc gtc acc tcc ggc ggc tcc ggc aac tgc cgc acc ggc      996
Gln Ala Gln Gly Val Thr Ser Gly Gly Ser Gly Asn Cys Arg Thr Gly
            155             160             165 ggg acc acc ttc tac cag gag gtc acc ccc atg gtg aac tcc tgg ggc     1044
Gly Thr Thr Phe Tyr Gln Glu Val Thr Pro Met Val Asn Ser Trp Gly
        170             175             180 gtc cgt ctc cgg acc taa                                             1062
Val Arg Leu Arg Thr
    185
```

<210> SEQ ID NO 8
<211> LENGTH: 353
<212> TYPE: PRT
<213> ORGANISM: Nocardiopsis prasina DSM 15649

<400> SEQUENCE: 8

```
Ala  Thr  Gly  Pro  Leu  Pro  Gln  Ser  Pro  Thr  Pro  Glu  Ala  Asp  Ala
-165                 -160                 -155

Val  Ser  Met  Gln  Glu  Ala  Leu  Gln  Arg  Asp  Leu  Gly  Leu  Thr  Pro
-150                 -145                 -140

Leu  Glu  Ala  Asp  Glu  Leu  Leu  Ala  Ala  Gln  Asp  Thr  Ala  Phe  Glu
-135                 -130                 -125

Val  Asp  Glu  Ala  Ala  Ala  Glu  Ala  Ala  Gly  Asp  Ala  Tyr  Gly  Gly
-120                 -115                 -110

Ser  Val  Phe  Asp  Thr  Glu  Thr  Leu  Glu  Leu  Thr  Val  Leu  Val  Thr  Asp
```

```
                -105               -100               -95                -90

Ser Ala Ala Val Glu Ala Val Glu Ala Thr Gly Ala Gly Thr Glu Leu
                        -85                -80                -75

Val Ser Tyr Gly Ile Thr Gly Leu Asp Glu Ile Val Glu Glu Leu Asn
                        -70                -65                -60

Ala Ala Asp Ala Val Pro Gly Val Gly Trp Tyr Pro Asp Val Ala
                        -55                -50                -45

Gly Asp Thr Val Val Leu Glu Val Leu Glu Gly Ser Gly Ala Asp Val
                        -40                -35                -30

Gly Gly Leu Leu Ala Asp Ala Gly Val Asp Ala Ser Ala Val Glu Val
    -25                 -20                -15                -10

Thr Thr Thr Glu Gln Pro Glu Leu Tyr Ala Asp Ile Ile Gly Gly Leu
                        -5                 -1   1             5

Ala Tyr Thr Met Gly Gly Arg Cys Ser Val Gly Phe Ala Ala Thr Asn
                        10                 15                 20

Ala Ala Gly Gln Pro Gly Phe Val Thr Ala Gly His Cys Gly Arg Val
                        25                 30                 35

Gly Thr Gln Val Thr Ile Gly Asn Gly Arg Gly Val Phe Glu Gln Ser
    40                  45                 50                 55

Ile Phe Pro Gly Asn Asp Ala Ala Phe Val Arg Gly Thr Ser Asn Phe
                        60                 65                 70

Thr Leu Thr Asn Leu Val Ser Arg Tyr Asn Thr Gly Gly Tyr Ala Thr
                        75                 80                 85

Val Ala Gly His Asn Gln Ala Pro Ile Gly Ser Ser Val Cys Arg Ser
                        90                 95                 100

Gly Ser Thr Thr Gly Trp His Cys Gly Thr Ile Gln Ala Arg Gly Gln
                        105                110                115

Ser Val Ser Tyr Pro Glu Gly Thr Val Thr Asn Met Thr Arg Thr Thr
    120                 125                130                135

Val Cys Ala Glu Pro Gly Asp Ser Gly Gly Ser Tyr Ile Ser Gly Asn
                        140                145                150

Gln Ala Gln Gly Val Thr Ser Gly Gly Ser Gly Asn Cys Arg Thr Gly
                        155                160                165

Gly Thr Thr Phe Tyr Gln Glu Val Thr Pro Met Val Asn Ser Trp Gly
                        170                175                180

Val Arg Leu Arg Thr
                185

<210> SEQ ID NO 9
<211> LENGTH: 1068
<212> TYPE: DNA
<213> ORGANISM: Nocardiopsis alba DSM 15647
<220> FEATURE:
<221> NAME/KEY: CDS
<222> LOCATION: (1)..(1065)
<220> FEATURE:
<221> NAME/KEY: mat_peptide
<222> LOCATION: (502)..(1065)

<400> SEQUENCE: 9 gcg acc ggc  ccc ctc ccc cag tcc  ccc acc ccg gat gaa  gcc gag      45
Ala Thr Gly  Pro Leu Pro Gln Ser  Pro Thr Pro Asp Glu  Ala Glu
             -165                 -160                  -155 gcc acc acc  atg gtc gag gcc ctc  cag cgc gac ctc ggc  ctg tcc      90
Ala Thr Thr  Met Val Glu Ala Leu  Gln Arg Asp Leu Gly  Leu Ser
             -150                 -145                  -140 ccc tct cag  gcc gac gag ctc ctc  gag gcg cag gcc gag  tcc ttc     135
```

```
                Pro Ser Gln Ala Asp Glu Leu Leu Glu Ala Gln Ala Glu Ser Phe
                        -135                -130                -125 gag atc gac gag gcc gcc acc gcg gcc gca gcc gac tcc tac ggc         180
Glu Ile Asp Glu Ala Ala Thr Ala Ala Ala Ala Asp Ser Tyr Gly
        -120                -115                -110 ggc tcc atc ttc gac acc gac agc ctc acc ctg acc gtc ctg gtc acc     228
Gly Ser Ile Phe Asp Thr Asp Ser Leu Thr Leu Thr Val Leu Val Thr
            -105                -100                -95 gac gcc tcc gcc gtc gag gcg gtc gag gcc gcc ggc gcc gag gcc aag     276
Asp Ala Ser Ala Val Glu Ala Val Glu Ala Ala Gly Ala Glu Ala Lys
        -90                 -85                 -80 gtg gtc tcg cac ggc atg gag ggc ctg gag gag atc gtc gcc gac ctg     324
Val Val Ser His Gly Met Glu Gly Leu Glu Glu Ile Val Ala Asp Leu
-75                 -70                 -65                 -60 aac gcg gcc gac gct cag ccc ggc gtc gtg ggc tgg tac ccc gac atc     372
Asn Ala Ala Asp Ala Gln Pro Gly Val Val Gly Trp Tyr Pro Asp Ile
                -55                 -50                 -45 cac tcc gac acg gtc gtc ctc gag gtc ctc gag ggc tcc ggt gcc gac     420
His Ser Asp Thr Val Val Leu Glu Val Leu Glu Gly Ser Gly Ala Asp
            -40                 -35                 -30 gtg gac tcc ctg ctc gcc gac gcc ggt gtg gac acc gcc gac gtc aag     468
Val Asp Ser Leu Leu Ala Asp Ala Gly Val Asp Thr Ala Asp Val Lys
        -25                 -20                 -15 gtg gag agc acc acc gag cag ccc gag ctg tac gcc gac atc atc ggc     516
Val Glu Ser Thr Thr Glu Gln Pro Glu Leu Tyr Ala Asp Ile Ile Gly
-10                  -5                 -1  1                  5 ggt ctc gcc tac acc atg ggt ggg cgc tgc tcg gtc ggc ttc gcg gcc     564
Gly Leu Ala Tyr Thr Met Gly Gly Arg Cys Ser Val Gly Phe Ala Ala
                10                  15                  20 acc aac gcc tcc ggc cag ccc ggg ttc gtc acc gcc ggc cac tgc ggc     612
Thr Asn Ala Ser Gly Gln Pro Gly Phe Val Thr Ala Gly His Cys Gly
            25                  30                  35 acc gtc ggc acc ccg gtc agc atc ggc aac ggc cag ggc gtc ttc gag     660
Thr Val Gly Thr Pro Val Ser Ile Gly Asn Gly Gln Gly Val Phe Glu
        40                  45                  50 cgt tcc gtc ttc ccc ggc aac gac tcc gcc ttc gtc cgc ggc acc tcg     708
Arg Ser Val Phe Pro Gly Asn Asp Ser Ala Phe Val Arg Gly Thr Ser
55                  60                  65 aac ttc acc ctg acc aac ctg gtc agc cgc tac aac acc ggt ggt tac     756
Asn Phe Thr Leu Thr Asn Leu Val Ser Arg Tyr Asn Thr Gly Gly Tyr
70                  75                  80                  85 gcg acc gtc tcc ggc tcc tcg cag gcg gcg atc ggc tcg cag atc tgc     804
Ala Thr Val Ser Gly Ser Ser Gln Ala Ala Ile Gly Ser Gln Ile Cys
                90                  95                  100 cgt tcc ggc tcc acc acc ggc tgg cac tgc ggc acc gtc cag gcc cgc     852
Arg Ser Gly Ser Thr Thr Gly Trp His Cys Gly Thr Val Gln Ala Arg
            105                 110                 115 ggc cag acg gtg agc tac ccc cag ggc acc gtg cag aac ctg acc cgc     900
Gly Gln Thr Val Ser Tyr Pro Gln Gly Thr Val Gln Asn Leu Thr Arg
        120                 125                 130 acc aac gtc tgc gcc gag ccc ggt gac tcc ggc ggc tcc ttc atc tcc     948
Thr Asn Val Cys Ala Glu Pro Gly Asp Ser Gly Gly Ser Phe Ile Ser
135                 140                 145 ggc agc cag gcc cag ggc gtc acc tcc ggt ggc tcc ggc aac tgc tcc     996
Gly Ser Gln Ala Gln Gly Val Thr Ser Gly Gly Ser Gly Asn Cys Ser
150                 155                 160                 165 ttc ggt ggc acc acc tac tac cag gag gtc aac ccg atg ctg agc agc    1044
Phe Gly Gly Thr Thr Tyr Tyr Gln Glu Val Asn Pro Met Leu Ser Ser
                170                 175                 180
```

```
tgg ggt ctg acc ctg cgc acc tga                                    1068
Trp Gly Leu Thr Leu Arg Thr
        185
```

<210> SEQ ID NO 10
<211> LENGTH: 355
<212> TYPE: PRT
<213> ORGANISM: Nocardiopsis alba DSM 15647

<400> SEQUENCE: 10

```
Ala Thr Gly Pro Leu Pro Gln Ser Pro Thr Pro Asp Glu Ala Glu
       -165            -160              -155

Ala Thr Thr Met Val Glu Ala Leu Gln Arg Asp Leu Gly Leu Ser
       -150            -145              -140

Pro Ser Gln Ala Asp Glu Leu Leu Glu Ala Gln Ala Glu Ser Phe
       -135            -130              -125

Glu Ile Asp Glu Ala Ala Thr Ala Ala Ala Ala Asp Ser Tyr Gly
       -120            -115              -110

Gly Ser Ile Phe Asp Thr Asp Ser Leu Thr Leu Thr Val Leu Val Thr
       -105            -100               -95

Asp Ala Ser Ala Val Glu Ala Val Glu Ala Ala Gly Ala Glu Ala Lys
    -90             -85              -80

Val Val Ser His Gly Met Glu Gly Leu Glu Glu Ile Val Ala Asp Leu
-75              -70              -65              -60

Asn Ala Ala Asp Ala Gln Pro Gly Val Val Gly Trp Tyr Pro Asp Ile
             -55              -50              -45

His Ser Asp Thr Val Val Leu Glu Val Leu Glu Gly Ser Gly Ala Asp
             -40              -35              -30

Val Asp Ser Leu Leu Ala Asp Ala Gly Val Asp Thr Ala Asp Val Lys
         -25              -20              -15

Val Glu Ser Thr Thr Glu Gln Pro Glu Leu Tyr Ala Asp Ile Ile Gly
        -10              -5               -1   1                5

Gly Leu Ala Tyr Thr Met Gly Gly Arg Cys Ser Val Gly Phe Ala Ala
                      10              15              20

Thr Asn Ala Ser Gly Gln Pro Gly Phe Val Thr Ala Gly His Cys Gly
                 25              30              35

Thr Val Gly Thr Pro Val Ser Ile Gly Asn Gly Gln Gly Val Phe Glu
             40              45              50

Arg Ser Val Phe Pro Gly Asn Asp Ser Ala Phe Val Arg Gly Thr Ser
 55              60              65

Asn Phe Thr Leu Thr Asn Leu Val Ser Arg Tyr Asn Thr Gly Gly Tyr
70              75              80              85

Ala Thr Val Ser Gly Ser Gln Ala Ala Ile Gly Ser Gln Ile Cys
             90              95              100

Arg Ser Gly Ser Thr Thr Gly Trp His Cys Gly Thr Val Gln Ala Arg
             105             110             115

Gly Gln Thr Val Ser Tyr Pro Gln Gly Thr Val Gln Asn Leu Thr Arg
         120             125             130

Thr Asn Val Cys Ala Glu Pro Gly Asp Ser Gly Gly Ser Phe Ile Ser
     135             140             145

Gly Ser Gln Ala Gln Gly Val Thr Ser Gly Gly Ser Gly Asn Cys Ser
150             155             160             165

Phe Gly Gly Thr Thr Tyr Tyr Gln Glu Val Asn Pro Met Leu Ser Ser
             170             175             180

Trp Gly Leu Thr Leu Arg Thr
```

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
ccgattatgg agcggattga acatgcg                                          27

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
gtgaccatcg gcgacggcag gggcgtcttc g                                     31

<210> SEQ ID NO 13
<211> LENGTH: 10172
<212> TYPE: DNA
<213> ORGANISM: Artificial Sequence
<220> FEATURE:
<223> OTHER INFORMATION: Expression Cassette
<220> FEATURE:
<221> NAME/KEY: source
<222> LOCATION: (1)..(3323)
<223> OTHER INFORMATION: Bacillus subtilis genome sequence including
      yfmH-yfmD-yfmC-yfmB-yfmA genes
<220> FEATURE:
<221> NAME/KEY: misc_recomb
<222> LOCATION: (3561)..(4208)
<223> OTHER INFORMATION: Cat gene providing chloramphenicol resistance
<220> FEATURE:
<221> NAME/KEY: promoter
<222> LOCATION: (4523)..(5633)
<223> OTHER INFORMATION: Triple PamyL-scBAN-CryIIIA promoter including
      mRNA stabilizing sequence
<220> FEATURE:
<221> NAME/KEY: sig_peptide
<222> LOCATION: (5658)..(5738)
<220> FEATURE:
<221> NAME/KEY: CDS
<222> LOCATION: (5658)..(6797)
<220> FEATURE:
<221> NAME/KEY: mat_peptide
<222> LOCATION: (6234)..(6797)
<220> FEATURE:
<221> NAME/KEY: source
<222> LOCATION: (6839)..(7540)
<223> OTHER INFORMATION: Part of Bacillus subtilis pectate lyase gene
<220> FEATURE:
<221> NAME/KEY: source
<222> LOCATION: (7541)..(10172)
<223> OTHER INFORMATION: Bacillus subtilis genome DNA inclding yflS-citM
      genes

<400> SEQUENCE: 13
gagtatcgcc agtaagggc gttttttgttt tctggttgtt ttcttcattt caggtttcgc      60
cctttccttg ccaaatataa gaaaaacggc gttccgataa tcgcggtgac aatgccgacc     120
ggtgattcat aaggaaatgc aatccatctg gccagaacat ctgcgtacac cagcaaaatg     180
gcaccgaaca gtgccgaaaa cggaagcacg tattgataat gttctccgat cagcttgcgg     240
acaatatgcg ggacgagcag cccgacaaag ccaatcggcc cggcgacggc tacgaaagcg     300
ccggaaagaa ttaaaataat caaactgatc agaatcctga tgccgttcat attttgtcca     360

```
agccctttg  ctgtttcgtc  tccgagaccg  agaacagaaa  cagaaccgga  aaatacgagg    420
gcaagcccga  tgccaatgac  agaaaaagga  gcgatggtta  tgacgtcctg  ccagttgctg    480
ccgtcgattg  cgcctgtcat  ccagtacaga  acatcctcac  ctgactcatt  taaaataatg    540
atggcctgtg  tcatagagga  gaggaacaag  tgcacggcca  ttcctgacag  cgccagcttg    600
acaggcgtca  ttccgccgga  tgaggcaatc  atatacacaa  tcgcgccgcc  tgctgccgca    660
cccgcaaaag  cgaatataac  agatgaatag  ggcgatgccg  gcagaatgac  gagagaagca    720
acaacaaaaa  gcgatgcacc  cgcattcaca  ccgaaaattt  ggggtgaagc  cagaggattt    780
ctggtcatag  cctgcatcag  cgcccctgct  acagctaggc  tggcgccgac  aaaaacgccg    840
attaatgtgc  ggggaaggcg  aagagtagag  atgatgagct  gttcctttga  accgtcccat    900
acaaaaagat  atttcaatga  atctatgatg  ctgatgtctg  aggctcctac  tgaaagattc    960
agcccaagcc  caaatataaa  aataatcagt  gcaatgataa  acatcatcag  tcttgatgat   1020
gagcgccgtt  tggctgaatg  atacaacagt  ctcacttcct  tactgcgtct  ggttgcaaaa   1080
acgaagaagc  aaggattccc  ctcgcttctc  atttgtccta  tttattatac  actttttaa    1140 gcacatcttt  ggcgcttgtt  tcactagact  tgatgcctct  gaatcttgtc  caagtgtcac   1200
ggtccgcatc  atagacttgt  ccattttca   ccgctttgag  attttttccag  agcgggttcg   1260 ttttccactc  atctacaatg  gttttgcctt  cgttggctga  gatgaacaaa  atatcaggat   1320 cgatttgct   caattgctca  aggctgacct  cttgatagcc  gttatctgac  ttcacagcgt   1380
gtgtaaagcc  tagcatttta  aagatttctc  cgtcatagga  tgatgatgta  tgaagctgga   1440
aggaatccgc  tcttgcaacg  ccgagaacga  tgttgcggtt  ttcatctttc  ggaagttcgg   1500
cttttagatc  gttgatgact  ttttttgtgct  cggcaagctt  ttctttttcct  tcatcttctt   1560 tatttaatgc  tttagcaatg  gtcgtaaagc  tgtcgatcgt  ttcgtcatat  gtcgcttcac   1620 ggcttttttaa  ttcaatcgtc  ggggcgattt  ttttcagctg  tttataaatg  ttttttatggc   1680 gctcagcgtc  agcgatgatt  aaatcaggct  tcaaggaact  gatgacctca  agattgggtt   1740
cgctgcgtgt  gcctacagat  gtgtaatcaa  tggagctgcc  gacaagcttt  ttaatcatat   1800
cttttttgtt  gtcatctgcg  atgcccaccg  gcgtaatgcc  gagattgtga  acggcatcca   1860
agaatgaaag  ctcaagcaca  accacccgct  taggtgtgcc  gcttactgtc  gttttttcctt   1920 cttcgtcatg  gatcactctg  gaatcctag   actcgctttt  gccgcttccg  ttgttattct   1980
ggcttgatga  acagccggat  acaatgaggc  aggcgagcaa  taaaacactc  atgatggcaa   2040
tcaacttgtt  agaataggtg  cgcatgtcat  tcttcctttt  ttcagattta  gtaatgagaa   2100
tcattatcac  atgtaacact  ataatagcat  ggcttatcat  gtcaatattt  ttttagtaaa   2160
gaaagctgcg  ttttactgc   tttctcatga  aagcatcatc  agacacaaat  aagtggtatg   2220
cagcgttacc  gtgtcttcga  gacaaaaacg  catgggcgtt  ggctttagag  gtttcgaaca   2280
tatcagcagt  gacataagga  aggagagtgc  tgagataacc  ggacaatttc  ttttctattt   2340
catctgttag  tgcaaattca  atgtcgccga  tattcatgat  aatcgagaaa  acaaagtcga   2400
tatcgatatg  aaaatgttcc  tcggcaaaaa  ccgcaagctc  gtgaattcct  ggtgaacatc   2460
cggcacgctt  atgaaaatc   tgtttgacta  aatcactcac  aatccaagca  ttgtattgct   2520
gttctggtga  aaagtattgc  attagacata  cctcctgctc  gtacggataa  aggcagcgtt   2580
tcatggtcgt  gtgctccgtg  cagcggcttc  tccttaattt  tgattttttct  gaaaataggt   2640 cccgttccta  tcactttacc  atggacggaa  aacaaatagc  tactaccatt  cctcctgttt   2700
```

```
ttctcttcaa tgttctggaa tctgtttcag gtacagacga tcgggtatga agaaatata    2760 gaaaacatga aggaggaata tcgacatgaa accagttgta aaagagtata caaatgacga    2820
acagctcatg aaagatgtag aggaattgca gaaaatgggt gttgcgaaag aggatgtata    2880
cgtcttagct cacgacgatg acagaacgga acgcctggct gacaacacga acgccaacac    2940
gatcggagcc aaagaaacag gtttcaagca cgcggtggga aatatcttca ataaaaaagg    3000
agacgagctc cgcaataaaa ttcacgaaat cggttttttct gaagatgaag ccgctcaatt    3060
tgaaaaacgc ttagatgaag gaaaagtgct tctctttgtg acagataacg aaaaagtgaa    3120
agcttgggca taaagcaagg aaaaaaccaa aaggccaatg tcggccttttt ggtttttttg    3180 cggtctttgc ggtgggattt tgcagaatgc cgcaatagga tagcggaaca ttttcggttc    3240
tgaatgtccc tcaatttgct attatatttt tgtgataaat tggaataaaa tctcacaaaa    3300
tagaaaatgg gggtacatag tggccatcat ggccagctag catgcacatg ggatctggga    3360
ccaataataa tgactagaga agaaagaatg aagattgttc atgaaattaa ggaacgaata    3420
ttggataaag tggggtattt ttaaaatata tatttatgtt acagtaatat tgacttttaa    3480
aaaaggattg attctaagaa gaaagcagac aagtaagcct cctaaattca ctttagataa    3540
aaatttagga ggcatatcaa atgaacttta ataaaattga tttagacaat tggaagagaa    3600
aagagatatt taatcattat ttgaaccaac aaacgacttt tagtataacc acagaaattg    3660
atattagtgt tttataccga aacataaaac aagaaggata taaattttac cctgcattta    3720
ttttcttagt gacaagggtg ataaactcaa atacagcttt tagaactggt tacaatagcg    3780
acggagagtt aggttattgg gataagttag agccacttta acaattttt gatggtgtat    3840 ctaaaacatt ctctggtatt tggactcctg taaagaatga cttcaaagag ttttatgatt    3900
tatacctttc tgatgtagag aaatataatg gttcggggaa attgtttccc aaaacaccta    3960
tacctgaaaa tgcttttttct ctttctatta ttccatggac ttcatttact gggtttaact    4020
taaatatcaa taataatagt aattaccttc tacccattat tacagcagga aaattcatta    4080
ataaaggtaa ttcaatatat ttaccgctat ctttacaggt acatcattct gtttgtgatg    4140
gttatcatgc aggattgttt atgaactcta ttcaggaatt gtcagatagg cctaatgact    4200 ggctttttata atatgagata tgccgactg tacttttttac agtcggtttt ctaacgatac    4260
attaataggt acgaaaaagc aacttttttt gcgcttaaaa ccagtcatac caataactta    4320
agggtaacta gcctcgccgg aaagagcgaa aatgcctcac atttgtgcca cctaaaaagg    4380
agcgatttac atatgagtta tgcagttgt agaatgcaaa aagtgaaatc agctggacta    4440
aaaggcatgg catgccttcg atagtttatt aatattagtg gagctcagtg agagcgaagc    4500
gaacacttga ttttttaatt ttctatcttt tataggtcat tagagtatac ttatttgtcc    4560
tataaactat ttagcagcat aatagattta ttgaataggt catttaagtt gagcatatta    4620
ggggaggaaa atcttggaga aatatttgaa gaacccgagg atctagatca ggtaccgcaa    4680
cgttcgcaga tgctgctgaa gagattatta aaaagctgaa agcaaaaggc tatcaattgg    4740
taactgtatc tcagcttgaa gaagtgaaga agcagagagg ctattgaata aatgagtaga    4800
aagcgccata tcggcgcttt tcttttggaa gaaaatatag ggaaaatggt acttgttaaa    4860
aattcggaat atttatacaa tatcatatgt atcacattga aggagggggc ctgctgtcca    4920
gactgtccgc tgtgtaaaaa aaggaataa aggggggttg acattatttt actgatatgt    4980
ataatataat ttgtataaga aaatggaggg gccctcgaaa cgtaagatga aaccttagat    5040
aaaagtgctt tttttgttgc aattgaagaa ttattaatgt taagcttaat taaagataat    5100
```

```
atctttgaat tgtaacgccc ctcaaaagta agaactacaa aaaaagaata cgttatatag    5160
aaatatgttt gaaccttctt cagattacaa atatattcgg acggactcta cctcaaatgc    5220
ttatctaact atagaatgac atacaagcac aaccttgaaa atttgaaaat ataactacca    5280
atgaacttgt tcatgtgaat tatcgctgta tttaattttc tcaattcaat atataatatg    5340
ccaatacatt gttacaagta gaaattaaga caccettgat agccttacta tacctaacat    5400
gatgtagtat taaatgaata tgtaaatata tttatgataa gaagcgactt atttataatc    5460
attacatatt tttctattgg aatgattaag attccaatag aatagtgtat aaattattta    5520
tcttgaaagg agggatgcct aaaaacgaag aacattaaaa acatatattt gcaccgtcta    5580
atggatttat gaaaaatcat tttatcagtt tgaaaattat gtattatgga gctctgaaaa    5640
aaaggagagg ataaaga atg aag aaa ccg ttg ggg aaa att gtc gca agc      5690
                    Met Lys Lys Pro Leu Gly Lys Ile Val Ala Ser
                       -190                -185 acc gca cta ctc att tct gtt gct ttt agt tca tcg atc gca tcg           5735
Thr Ala Leu Leu Ile Ser Val Ala Phe Ser Ser Ser Ile Ala Ser
   -180            -175             -170 gct gcc acc gga gcg ctc ccc cag tca ccc acc ccg gag gcc gac           5780
Ala Ala Thr Gly Ala Leu Pro Gln Ser Pro Thr Pro Glu Ala Asp
   -165            -160             -155 gcg gtc tcc atg cag gag gcg ctc cag cgc gac ctc gac ctg acc           5825
Ala Val Ser Met Gln Glu Ala Leu Gln Arg Asp Leu Asp Leu Thr
   -150            -145             -140 tcc gcc gag gcc gag gag ctg ctg gcc gcc cag gac acc gcc ttc           5870
Ser Ala Glu Ala Glu Glu Leu Leu Ala Ala Gln Asp Thr Ala Phe
   -135            -130             -125 gag gtc gac gag gcc gcg gcc gag gcc gcc ggg gac gcc tac ggc           5915
Glu Val Asp Glu Ala Ala Ala Glu Ala Ala Gly Asp Ala Tyr Gly
   -120            -115             -110 ggc tcc gtc ttc gac acc gag agc ctg gaa ctg acc gtc ctg gtc acc      5963
Gly Ser Val Phe Asp Thr Glu Ser Leu Glu Leu Thr Val Leu Val Thr
   -105            -100              -95 gat gcc gcc gcg gtc gag gcc gtg gag gcc acc ggc gcc ggg acc gag      6011
Asp Ala Ala Ala Val Glu Ala Val Glu Ala Thr Gly Ala Gly Thr Glu
-90              -85              -80              -75 ctg gtc tcc tac ggc atc gac ggt ctc gac gag atc gtc cag gag ctc      6059
Leu Val Ser Tyr Gly Ile Asp Gly Leu Asp Glu Ile Val Gln Glu Leu
                 -70              -65              -60 aac gcc gcc gac gcc gtt ccc ggt gtg gtc ggc tgg tac ccg gac gtg     6107
Asn Ala Ala Asp Ala Val Pro Gly Val Val Gly Trp Tyr Pro Asp Val
             -55              -50              -45 gcg ggt gac acc gtc gtc ctg gag gtc ctg gag ggt tcc gga gcc gac     6155
Ala Gly Asp Thr Val Val Leu Glu Val Leu Glu Gly Ser Gly Ala Asp
         -40              -35              -30 gtc agc ggc ctg ctc gcg gac gcc ggc gtg gac gcc tcg gcc gtc gag     6203
Val Ser Gly Leu Leu Ala Asp Ala Gly Val Asp Ala Ser Ala Val Glu
     -25              -20              -15 gtg acc acg agc gac cag ccc gag ctc tac gcc gac atc atc ggt ggt     6251
Val Thr Thr Ser Asp Gln Pro Glu Leu Tyr Ala Asp Ile Ile Gly Gly
-10               -5              -1  1                 5 ctg gcc tac acc atg ggc ggc cgc tgt tcg gtc ggc ttc gcg gcc acc     6299
Leu Ala Tyr Thr Met Gly Gly Arg Cys Ser Val Gly Phe Ala Ala Thr
              10              15              20 aac gcc gcc ggt cag ccc ggg ttc gtc acc gcc ggt cac tgc ggc cgc     6347
Asn Ala Ala Gly Gln Pro Gly Phe Val Thr Ala Gly His Cys Gly Arg
     25              30              35
```

| | | | | | | | | | | | | | | | | |
|---|---|---|---|---|---|---|---|---|---|---|---|---|---|---|---|---|
| gtg | ggc | acc | cag | gtg | acc | atc | ggc | aac | ggc | agg | ggc | gtc | ttc | gag | cag | 6395 |
| Val | Gly | Thr | Gln | Val | Thr | Ile | Gly | Asn | Gly | Arg | Gly | Val | Phe | Glu | Gln | |
| | 40 | | | | 45 | | | | | 50 | | | | | | |

| | | | | | | | | | | | | | | | | |
|---|---|---|---|---|---|---|---|---|---|---|---|---|---|---|---|---|
| tcc | gtc | ttc | ccc | ggc | aac | gac | gcg | gcc | ttc | gtc | cgc | ggt | acg | tcc | aac | 6443 |
| Ser | Val | Phe | Pro | Gly | Asn | Asp | Ala | Ala | Phe | Val | Arg | Gly | Thr | Ser | Asn | |
| 55 | | | | | 60 | | | | | 65 | | | | | 70 | |

| | | | | | | | | | | | | | | | | |
|---|---|---|---|---|---|---|---|---|---|---|---|---|---|---|---|---|
| ttc | acg | ctg | acc | aac | ctg | gtc | agc | cgc | tac | aac | acc | ggc | ggg | tac | gcc | 6491 |
| Phe | Thr | Leu | Thr | Asn | Leu | Val | Ser | Arg | Tyr | Asn | Thr | Gly | Gly | Tyr | Ala | |
| | | | | 75 | | | | | 80 | | | | | 85 | | |

| | | | | | | | | | | | | | | | | |
|---|---|---|---|---|---|---|---|---|---|---|---|---|---|---|---|---|
| acg | gtc | gcc | ggt | cac | aac | cag | gcc | ccc | atc | ggc | tcc | tcc | gtc | tgc | cgc | 6539 |
| Thr | Val | Ala | Gly | His | Asn | Gln | Ala | Pro | Ile | Gly | Ser | Ser | Val | Cys | Arg | |
| | | | 90 | | | | | 95 | | | | | 100 | | | |

| | | | | | | | | | | | | | | | | |
|---|---|---|---|---|---|---|---|---|---|---|---|---|---|---|---|---|
| tcc | ggc | tcc | acc | acc | ggt | tgg | cac | tgc | ggc | acc | atc | cag | gcc | cgc | ggc | 6587 |
| Ser | Gly | Ser | Thr | Thr | Gly | Trp | His | Cys | Gly | Thr | Ile | Gln | Ala | Arg | Gly | |
| | | 105 | | | | | 110 | | | | | 115 | | | | |

| | | | | | | | | | | | | | | | | |
|---|---|---|---|---|---|---|---|---|---|---|---|---|---|---|---|---|
| cag | tcg | gtg | agc | tac | ccc | gag | ggc | acc | gtc | acc | aac | atg | acc | cgg | acc | 6635 |
| Gln | Ser | Val | Ser | Tyr | Pro | Glu | Gly | Thr | Val | Thr | Asn | Met | Thr | Arg | Thr | |
| | 120 | | | | | 125 | | | | | 130 | | | | | |

| | | | | | | | | | | | | | | | | |
|---|---|---|---|---|---|---|---|---|---|---|---|---|---|---|---|---|
| acc | gtg | tgc | gcc | gag | ccc | ggc | gac | tcc | ggc | ggc | tcc | tac | atc | tcc | ggc | 6683 |
| Thr | Val | Cys | Ala | Glu | Pro | Gly | Asp | Ser | Gly | Gly | Ser | Tyr | Ile | Ser | Gly | |
| 135 | | | | | 140 | | | | | 145 | | | | | 150 | |

| | | | | | | | | | | | | | | | | |
|---|---|---|---|---|---|---|---|---|---|---|---|---|---|---|---|---|
| acc | cag | gcc | cag | ggc | gtg | acc | tcc | ggc | ggc | tcc | ggc | aac | tgc | cgc | acc | 6731 |
| Thr | Gln | Ala | Gln | Gly | Val | Thr | Ser | Gly | Gly | Ser | Gly | Asn | Cys | Arg | Thr | |
| | | | | 155 | | | | | 160 | | | | | 165 | | |

| | | | | | | | | | | | | | | | | |
|---|---|---|---|---|---|---|---|---|---|---|---|---|---|---|---|---|
| ggc | ggg | acc | acc | ttc | tac | cag | gag | gtc | acc | ccc | atg | gtg | aac | tcc | tgg | 6779 |
| Gly | Gly | Thr | Thr | Phe | Tyr | Gln | Glu | Val | Thr | Pro | Met | Val | Asn | Ser | Trp | |
| | | | 170 | | | | | 175 | | | | | 180 | | | |

| | | | | | | | |
|---|---|---|---|---|---|---|---|
| ggc | gtc | cgt | ctc | cgg | acc | taatcgcatg ttcaatccgc tccataatcg | 6827 |
| Gly | Val | Arg | Leu | Arg | Thr | | |
| | | 185 | | | | | |

| | |
|---|---|
| gtcgacgcgg cggttcgcgt ccggacagca catcaccgaa atattatgga agaaaatatc | 6887 |
| agcaccatga cggccaaacg gatgcttcca acggtgctaa ctatatcacg atgtcctaca | 6947 |
| actattatca cgatcatgat aaaagctcca ttttcggatc aagtgacagc aaaacctccg | 7007 |
| atgacggcaa attaaaaatt acgctgcatc ataaccgcta taaaaatatt gtccagcgcg | 7067 |
| cgccgagagt ccgcttcggg caagtgcacg tatacaacaa ctattatgaa ggaagcacaa | 7127 |
| gctcttcaag ttatcctttt agctatgcat ggggaatcgg aaagtcatct aaaatctatg | 7187 |
| cccaaaacaa tgtcattgac gtaccgggac tgtcagctgc taaaacgatc agcgtattca | 7247 |
| gcgggggaac ggctttatat gactccggca cgttgctgaa cggcacacag atcaacgcat | 7307 |
| cggctgcaaa cgggctgagc tcttctgtcg gctggacgcc gtctctgcat ggatcgattg | 7367 |
| atgcttctgc taatgtgaaa tcaaatgtta taaatcaagc gggtgcgggt aaattaaatt | 7427 |
| aagaaagtga aaaacacaaa gggtgctaac ctttgtgttt tttaattaat taaaatgttt | 7487 |
| attaacttag ttaaggagta aatggaaaa gggatcgga aaacaagtat ataggaggag | 7547 |
| acctatttat ggcttcagaa aaagacgcag gaaaacagtc agcagtaaag cttgttccat | 7607 |
| tgcttattac tgtcgctgtg ggactaatca tctggtttat cccgctccg tccgacttg | 7667 |
| aacctaaagc ttggcatttg tttgcgattt ttgtcgcaac aattatcggc tttatctcca | 7727 |
| agcccttgcc aatgggtgca attgcaattt ttgcattggc ggttactgca ctaactggaa | 7787 |
| cactatcaat tgaggataca ttaagcggat tcgggaataa gaccatttgg cttatcgtta | 7847 |
| tcgcattctt tatttcccgg ggatttatca aaaccggtct cggtgcgaga atttcgtatg | 7907 |
| tattcgttca gaaattcgga aaaaaaaccc ttggactttc ttattcactg ctattcagtg | 7967 |
| atttaatact ttcacctgct attccaagta atacggcgcg tgcaggaggc attatatttc | 8027 |

```
ctattatcag atcattatcc gaaacattcg gatcaagccc ggcaaatgga acagagagaa    8087
aaatcggtgc attcttatta aaaccggtt ttcaggggaa tctgatcaca tctgctatgt    8147
tcctgacagc gatggcggcg aacccgctga ttgccaagct ggcccatgat gtcgcagggg   8207
tggacttaac atggacaagc tgggcaattg ccgcgattgt accgggactt gtaagcttaa   8267
tcatcacgcc gcttgtgatt tacaaactgt atccgccgga aatcaaagaa acaccggatg   8327
cggcgaaaat cgcaacagaa aaactgaaag aaatgggacc gttcaaaaaa tcggagcttt   8387
ccatggttat cgtgtttctt ttggtgcttg tgctgtggat ttttggcggc agcttcaaca   8447
tcgacgctac cacaaccgca ttgatcggtt tggccgttct cttattatca caagttctga   8507
cttgggatga tatcaagaaa gaacagggcg cttgggatac gctcacttgg tttgcggcgc   8567
ttgtcatgct cgccaacttc ttgaatgaat taggcatggt gtcttggttc agtaatgcca   8627
tgaaatcatc cgtatcaggg ttctcttgga ttgtggcatt catcatttta attgttgtgt   8687
attattactc tcactatttc tttgcaagtg cgacagccca catcagtgcg atgtattcag   8747
cattttggc tgtcgtcgtg gcagcgggcg caccgccgct tttagcagcg ctgagcctcg    8807
cgttcatcag caacctgttc gggtcaacga ctcactacgg ttctggagcg gctccggtct   8867
tcttcggagc aggctacatc ccgcaaggca atggtggtc catcggattt atcctgtcga    8927
ttgttcatat catccgtatgg cttgtgatcg gcggattatg gtggaaagta ctaggaatat   8987
ggtagaaaga aaaaggcaga cgcggtctgc cttttttat tttcactcct tcgtaagaaa     9047
atggatttg aaaaatgaga aaattccctg tgaaaatgg tatgatctag gtagaaagga    9107
cggctggtgc tgtggtgaaa aagcggttcc atttttccct gcaaacaaaa ataatggggc   9167
tgattgcggc tctgctggtc tttgtcattg gtgtgctgac cattacgtta gccgttcagc   9227
atacacaggg agaacggaga caggcagagc agctggcggt tcaaacggcg agaaccattt   9287
cctatatgcc gccggttaaa gagctcattg agagaaaaga cggacatgcg gctcagacgc   9347
aagaggtcat tgaacaaatg aaagaacaga ctggtgcgtt tgccattat gttttgaacg    9407
aaaaaggaga cattcgcagc gcctctggaa aagcggatt aaagaaactg gagcgcagca    9467
gagaaatttt gtttggcggt tcgcatgttt ctgaaacaaa agcggatgga cgaagagtga   9527
tcagagggag cgcgccgatt ataaaagaac agaagggata cagccaagtg atcggcagcg   9587
tgtctgttga ttttctgcaa acggagacag agcaaagcat caaaaagcat ttgagaaatt   9647
tgagtgtgat tgctgtgctt gtactgctgc tcggatttat tggcgccgcc gtgctggcga   9707
aaagcatcag aaaggatacg ctcgggcttg aaccgcatga atcgcggct ctatatcgtg    9767
agaggaacgc aatgctttc gcgattcgag aagggattat tgccaccaat cgtgaaggcg    9827
tcgtcaccat gatgaacgta tcggcggccg agatgctgaa gctgcccgag cctgatcc     9887
atcttcctat agatgacgtc atgccgggag cagggctgat gtctgtgctt gaaaaggag     9947
aaatgctgcc gaaccaggaa gtaagcgtca acgatcaagt gtttattatc aatacgaaag  10007
tgatgaatca aggcgggcag gcgtatggga ttgtcgtcag cttcagggag aaaacagagc  10067
tgaagaagct gatcgacaca ttgacagagg ttcgcaaata ttcagaggat ctcagggcgc  10127
agactcatga attttcaaat aagctttatg cgattttagg gctgc                  10172
```

<210> SEQ ID NO 14
<211> LENGTH: 380
<212> TYPE: PRT
<213> ORGANISM: Artificial Sequence
<220> FEATURE:

<223> OTHER INFORMATION: Synthetic Construct

<400> SEQUENCE: 14

```
Met Lys Lys Pro Leu Gly Lys Ile Val Ala Ser Thr Ala Leu Leu
    -190             -185                 -180

Ile Ser Val Ala Phe Ser Ser Ile Ala Ser Ala Ala Thr Gly
    -175             -170                 -165

Ala Leu Pro Gln Ser Pro Thr Pro Glu Ala Asp Ala Val Ser Met
    -160             -155                 -150

Gln Glu Ala Leu Gln Arg Asp Leu Asp Leu Thr Ser Ala Glu Ala
    -145             -140                 -135

Glu Glu Leu Leu Ala Ala Gln Asp Thr Ala Phe Glu Val Asp Glu
    -130             -125                 -120

Ala Ala Ala Glu Ala Ala Gly Asp Ala Tyr Gly Gly Ser Val Phe
    -115             -110                 -105

Asp Thr Glu Ser Leu Glu Leu Thr Val Leu Val Thr Asp Ala Ala Ala
    -100             -95                  -90

Val Glu Ala Val Glu Ala Thr Gly Ala Gly Thr Glu Leu Val Ser Tyr
    -85              -80                  -75

Gly Ile Asp Gly Leu Asp Glu Ile Val Gln Glu Leu Asn Ala Ala Asp
-70              -65                  -60                   -55

Ala Val Pro Gly Val Gly Trp Tyr Pro Asp Val Ala Gly Asp Thr
                 -50                 -45                   -40

Val Val Leu Glu Val Leu Glu Gly Ser Gly Ala Asp Val Ser Gly Leu
                 -35                 -30                   -25

Leu Ala Asp Ala Gly Val Asp Ala Ser Ala Val Glu Val Thr Thr Ser
                 -20                 -15                   -10

Asp Gln Pro Glu Leu Tyr Ala Asp Ile Ile Gly Gly Leu Ala Tyr Thr
    -5                -1   1              5                    10

Met Gly Gly Arg Cys Ser Val Gly Phe Ala Ala Thr Asn Ala Ala Gly
                 15                  20                    25

Gln Pro Gly Phe Val Thr Ala Gly His Cys Gly Arg Val Gly Thr Gln
                 30                  35                    40

Val Thr Ile Gly Asn Gly Arg Gly Val Phe Glu Gln Ser Val Phe Pro
                 45                  50                    55

Gly Asn Asp Ala Ala Phe Val Arg Gly Thr Ser Asn Phe Thr Leu Thr
    60                   65                  70

Asn Leu Val Ser Arg Tyr Asn Thr Gly Tyr Ala Thr Val Ala Gly
75               80                  85                    90

His Asn Gln Ala Pro Ile Gly Ser Ser Val Cys Arg Ser Gly Ser Thr
                 95                  100                   105

Thr Gly Trp His Cys Gly Thr Ile Gln Ala Arg Gly Gln Ser Val Ser
                 110                 115                   120

Tyr Pro Glu Gly Thr Val Thr Asn Met Thr Arg Thr Thr Val Cys Ala
                 125                 130                   135

Glu Pro Gly Asp Ser Gly Gly Ser Tyr Ile Ser Gly Thr Gln Ala Gln
                 140                 145                   150

Gly Val Thr Ser Gly Gly Ser Gly Asn Cys Arg Thr Gly Gly Thr Thr
155              160                 165                   170

Phe Tyr Gln Glu Val Thr Pro Met Val Asn Ser Trp Gly Val Arg Leu
                 175                 180                   185

Arg Thr
```

<210> SEQ ID NO 15
<211> LENGTH: 35
<212> TYPE: DNA
<213> ORGANISM: Artificial Sequence
<220> FEATURE:
<223> OTHER INFORMATION: Primer

<400> SEQUENCE: 15
ggagctctga aaaaaggag aggataaaga atgaa                         35

<210> SEQ ID NO 16
<211> LENGTH: 29
<212> TYPE: DNA
<213> ORGANISM: Artificial Sequence
<220> FEATURE:
<223> OTHER INFORMATION: Primer

<400> SEQUENCE: 16
gcgttccgat aatcgcggtg acaatgccg                               29

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
ttcatgagtc tgcgccctga gatcctctg                               29

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
taatcgcatg ttcaatccgc tccataatcg                              30

<210> SEQ ID NO 19
<211> LENGTH: 44
<212> TYPE: DNA
<213> ORGANISM: Artificial Sequence
<220> FEATURE:
<223> OTHER INFORMATION: Primer

<400> SEQUENCE: 19
cccaacggtt tcttcattct ttatcctctc cttttttttca gagc             44

<210> SEQ ID NO 20
<211> LENGTH: 1164
<212> TYPE: DNA
<213> ORGANISM: Artificial Sequence
<220> FEATURE:
<223> OTHER INFORMATION: Protease 22
<220> FEATURE:
<221> NAME/KEY: CDS
<222> LOCATION: (1)..(1164)
<220> FEATURE:
<221> NAME/KEY: sig_peptide
<222> LOCATION: (1)..(81)
<220> FEATURE:
<221> NAME/KEY: mat_peptide
<222> LOCATION: (577)..(1164)

<400> SEQUENCE: 20 atg aaa aaa  ccg ctg gga aaa att  gtc gca agc aca gca  ctt ctt    45

```
        Met Lys Lys Pro Leu Gly Lys Ile Val Ala Ser Thr Ala Leu Leu
            -190            -185            -180 att tca gtg gca ttt agc tca tct att gca tca gca gct aca gga           90
Ile Ser Val Ala Phe Ser Ser Ser Ile Ala Ser Ala Ala Thr Gly
        -175            -170            -165 gca tta ccg cag tct ccg aca ccg gaa gca gat gca gtc tca atg          135
Ala Leu Pro Gln Ser Pro Thr Pro Glu Ala Asp Ala Val Ser Met
        -160            -155            -150 caa gaa gca ctg caa aga gat ctt gat ctt aca tca gca gaa gca          180
Gln Glu Ala Leu Gln Arg Asp Leu Asp Leu Thr Ser Ala Glu Ala
        -145            -140            -135 gaa gaa ctt ctt gct gca caa gat aca gca ttt gaa gtg gat gaa          225
Glu Glu Leu Leu Ala Ala Gln Asp Thr Ala Phe Glu Val Asp Glu
        -130            -125            -120 gca gcg gca gaa gca gca gga gat gca tat ggc ggc tca gtt ttt          270
Ala Ala Ala Glu Ala Ala Gly Asp Ala Tyr Gly Gly Ser Val Phe
        -115            -110            -105 gat aca gaa tca ctt gaa ctt aca gtt ctt gtt aca gat gca gca gca      318
Asp Thr Glu Ser Leu Glu Leu Thr Val Leu Val Thr Asp Ala Ala Ala
        -100             -95             -90 gtt gaa gca gtt gaa gca aca gga gca gga aca gta ctt gtt tca tat      366
Val Glu Ala Val Glu Ala Thr Gly Ala Gly Thr Val Leu Val Ser Tyr
         -85             -80             -75 gga att gat ggc ctt gat gaa att gtt caa gaa ctg aat gca gct gat      414
Gly Ile Asp Gly Leu Asp Glu Ile Val Gln Glu Leu Asn Ala Ala Asp
-70              -65             -60             -55 gct gtt ccg ggc gtt gtt ggc tgg tat ccg gat gtt gct gga gat aca      462
Ala Val Pro Gly Val Val Gly Trp Tyr Pro Asp Val Ala Gly Asp Thr
             -50             -45             -40 gtt gtc ctt gaa gtt ctt gaa gga tca ggc gca gat gtt tca ggc ctg      510
Val Val Leu Glu Val Leu Glu Gly Ser Gly Ala Asp Val Ser Gly Leu
         -35             -30             -25 ctg gca gac gca gga gtc gat gca tca gca gtt gaa gtt aca aca tca      558
Leu Ala Asp Ala Gly Val Asp Ala Ser Ala Val Glu Val Thr Thr Ser
         -20             -15             -10 gat caa ccg gaa ctt tat gca gat att att ggc ggc ctg gca tat tat      606
Asp Gln Pro Glu Leu Tyr Ala Asp Ile Ile Gly Gly Leu Ala Tyr Tyr
          -5              -1 1              5              10 atg ggc ggc aga tgc agc gtt ggc ttt gca gca aca aat gca tca ggc      654
Met Gly Gly Arg Cys Ser Val Gly Phe Ala Ala Thr Asn Ala Ser Gly
              15              20              25 caa ccg ggc ttt gtt aca gca ggc cat tgc ggc aca gtt ggc aca cca      702
Gln Pro Gly Phe Val Thr Ala Gly His Cys Gly Thr Val Gly Thr Pro
          30              35              40 gtt tca att ggc aat ggc aaa ggc gtt ttt gaa cga agc att ttt ccg      750
Val Ser Ile Gly Asn Gly Lys Gly Val Phe Glu Arg Ser Ile Phe Pro
          45              50              55 ggc aat gat tca gca ttt gtt aga ggc aca tca aat ttt aca ctt aca      798
Gly Asn Asp Ser Ala Phe Val Arg Gly Thr Ser Asn Phe Thr Leu Thr
      60              65              70 aat ctg gtt tca aga tat aat tca ggc ggc tat gca aca gtt gca ggc      846
Asn Leu Val Ser Arg Tyr Asn Ser Gly Gly Tyr Ala Thr Val Ala Gly
75              80              85              90 cat aat caa gca ccg att ggc tca gca gtt tgc aga tca ggc tca aca      894
His Asn Gln Ala Pro Ile Gly Ser Ala Val Cys Arg Ser Gly Ser Thr
              95             100             105 aca ggc tgg cat tgc ggc aca att caa gca aga aat caa aca gtt agg      942
Thr Gly Trp His Cys Gly Thr Ile Gln Ala Arg Asn Gln Thr Val Arg
          110             115             120
```

```
tat ccg caa ggc aca gtt tat agt ctg aca aga aca aca gtt tgt gca      990
Tyr Pro Gln Gly Thr Val Tyr Ser Leu Thr Arg Thr Thr Val Cys Ala
        125                 130                 135 gaa ccg ggc gat tca ggc ggc tca tat att agc ggc act caa gca caa     1038
Glu Pro Gly Asp Ser Gly Gly Ser Tyr Ile Ser Gly Thr Gln Ala Gln
140                 145                 150 ggc gtt aca tca ggc ggc tca ggc aat tgc agt gct ggc ggc aca aca     1086
Gly Val Thr Ser Gly Gly Ser Gly Asn Cys Ser Ala Gly Gly Thr Thr
155                 160                 165                 170 tat tac caa gaa gtt aat ccg atg ctt agt tca tgg ggc ctt aca ctt     1134
Tyr Tyr Gln Glu Val Asn Pro Met Leu Ser Ser Trp Gly Leu Thr Leu
            175                 180                 185 aga aca caa tcg cat gtt caa tcc gct cca                             1164
Arg Thr Gln Ser His Val Gln Ser Ala Pro
        190                 195

<210> SEQ ID NO 21
<211> LENGTH: 388
<212> TYPE: PRT
<213> ORGANISM: Artificial Sequence
<220> FEATURE:
<223> OTHER INFORMATION: Synthetic Construct

<400> SEQUENCE: 21

Met Lys Lys  Pro Leu Gly Lys Ile  Val Ala Ser Thr Ala  Leu Leu
       -190              -185                -180

Ile Ser Val  Ala Phe Ser Ser Ser  Ile Ala Ser Ala Ala  Thr Gly
       -175              -170                -165

Ala Leu Pro  Gln Ser Pro Thr Pro  Glu Ala Asp Ala Val  Ser Met
       -160              -155                -150

Gln Glu Ala  Leu Gln Arg Asp Leu  Asp Leu Thr Ser Ala  Glu Ala
       -145              -140                -135

Glu Glu Leu  Leu Ala Ala Gln Asp  Thr Ala Phe Glu Val  Asp Glu
       -130              -125                -120

Ala Ala Ala  Glu Ala Ala Gly Asp  Ala Tyr Gly Gly Ser  Val Phe
       -115              -110                -105

Asp Thr Glu  Ser Leu Glu Leu Thr  Val Leu Val Thr Asp  Ala Ala Ala
       -100              -95                 -90

Val Glu Ala  Val Glu Ala Thr Gly  Ala Gly Thr Val Leu  Val Ser Tyr
       -85               -80                 -75

Gly Ile Asp Gly Leu Asp Glu Ile Val Gln Glu Leu Asn Ala Ala Asp
-70                 -65                 -60                 -55

Ala Val Pro  Gly Val Val Gly Trp  Tyr Pro Asp Val Ala  Gly Asp Thr
                  -50                 -45                 -40

Val Val Leu  Glu Val Leu Glu Gly  Ser Gly Ala Asp Val  Ser Gly Leu
            -35                 -30                 -25

Leu Ala Asp  Ala Gly Val Asp Ala  Ser Ala Val Glu Val  Thr Thr Ser
       -20               -15                 -10

Asp Gln Pro  Glu Leu Tyr Ala Asp  Ile Ile Gly Gly Leu  Ala Tyr Tyr
       -5                -1  1                 5                 10

Met Gly Gly  Arg Cys Ser Val Gly  Phe Ala Ala Thr Asn  Ala Ser Gly
                  15                  20                  25

Gln Pro Gly  Phe Val Thr Ala Gly  His Cys Gly Thr Val  Gly Thr Pro
                  30                  35                  40

Val Ser Ile  Gly Asn Gly Lys Gly  Val Phe Glu Arg Ser  Ile Phe Pro
                  45                  50                  55

Gly Asn Asp Ser Ala Phe Val Arg Gly Thr Ser Asn Phe Thr Leu Thr
```

```
                60                    65                     70
Asn Leu Val Ser Arg Tyr Asn Ser Gly Gly Tyr Ala Thr Val Ala Gly
 75                  80                  85                   90

His Asn Gln Ala Pro Ile Gly Ser Ala Val Cys Arg Ser Gly Ser Thr
             95                     100                 105

Thr Gly Trp His Cys Gly Thr Ile Gln Ala Arg Asn Gln Thr Val Arg
                110                 115                 120

Tyr Pro Gln Gly Thr Val Tyr Ser Leu Thr Arg Thr Val Cys Ala
         125                 130                 135

Glu Pro Gly Asp Ser Gly Gly Ser Tyr Ile Ser Gly Thr Gln Ala Gln
         140                 145                 150

Gly Val Thr Ser Gly Gly Ser Gly Asn Cys Ser Ala Gly Gly Thr Thr
155                 160                 165                 170

Tyr Tyr Gln Glu Val Asn Pro Met Leu Ser Ser Trp Gly Leu Thr Leu
                175                 180                 185

Arg Thr Gln Ser His Val Gln Ser Ala Pro
            190                 195
```